United States Patent
Shin et al.

(10) Patent No.: US 11,678,573 B2
(45) Date of Patent: Jun. 13, 2023

(54) ORGANIC COMPOUND, ORGANIC LIGHT-EMITTING DIODE AND ORGANIC LIGHT-EMITTING DEVICE CONTAINING THE COMPOUND

(71) Applicant: LG Display Co., Ltd., Seoul (KR)

(72) Inventors: In-Ae Shin, Paju-si (KR); Suk-Young Bae, Paju-si (KR); Joong-Hwan Yang, Paju-si (KR); Jun-Yun Kim, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 529 days.

(21) Appl. No.: 16/590,882

(22) Filed: Oct. 2, 2019

(65) Prior Publication Data

US 2020/0119284 A1 Apr. 16, 2020

(30) Foreign Application Priority Data

Oct. 10, 2018 (KR) .......................... 10-2018-0120461

(51) Int. Cl.
 *C07D 401/14* (2006.01)
 *H10K 85/60* (2023.01)
 (Continued)

(52) U.S. Cl.
 CPC ......... *H10K 85/654* (2023.02); *C07D 401/14* (2013.01); *C09K 11/02* (2013.01);
 (Continued)

(58) Field of Classification Search
 CPC ............ H01L 51/0067; H01L 51/0072; H01L 27/3244; H01L 51/5004; H01L 51/5016;
 (Continued)

(56) References Cited

U.S. PATENT DOCUMENTS

2010/0084647 A1* 4/2010 Kondakova ......... H01L 51/0067
 257/E51.026
2014/0183467 A1* 7/2014 Choi .................... C07F 15/0093
 546/10

(Continued)

FOREIGN PATENT DOCUMENTS

CN 102503937 A * 6/2012
CN 106810569 A 6/2017

(Continued)

OTHER PUBLICATIONS

C. Bizzarri "Triplet emitters versus TADF emitters in OLEDs: A comparative study" Polyhedron 140 (2018) 51-66 (Year: 2018).*

(Continued)

*Primary Examiner* — Michael Y Sun
(74) *Attorney, Agent, or Firm* — Morgan, Lewis & Bockius LLP

(57) ABSTRACT

An organic compound having a fused heteroaromatic moiety as an electron donor and a tri-pyrimidine moiety sharing an arylene group as an electron acceptor bonded to the fused heteroaromatic moiety, an organic light-emitting diode and an organic light-emitting device including the organic compound are disclosed, where the organic compound leads to enhanced luminous efficiency and lower driving voltages.

34 Claims, 8 Drawing Sheets

(51) Int. Cl.
*C09K 11/02* (2006.01)
*C09K 11/06* (2006.01)
*H10K 50/11* (2023.01)
*H10K 50/18* (2023.01)
*H10K 59/12* (2023.01)
*H10K 101/10* (2023.01)
*H10K 101/30* (2023.01)
*H10K 101/40* (2023.01)

(52) U.S. Cl.
CPC .......... *C09K 11/06* (2013.01); *H10K 85/6572* (2023.02); *C09K 2211/1007* (2013.01); *C09K 2211/1018* (2013.01); *H10K 50/11* (2023.02); *H10K 50/18* (2023.02); *H10K 59/12* (2023.02); *H10K 2101/10* (2023.02); *H10K 2101/30* (2023.02); *H10K 2101/40* (2023.02)

(58) Field of Classification Search
CPC .......... H01L 51/5096; H01L 2251/552; H01L 51/5012; H01L 51/0071; H01L 51/5024; H01L 51/504; C07D 401/14; C07D 403/14; C07D 405/14; C07D 409/14; C07D 413/14; C07D 417/14; C09K 11/02; C09K 11/06; C09K 2211/1007; C09K 2211/1018; C09K 2211/1029; C09K 2211/1033; C09K 2211/1037; C09K 2211/1044

See application file for complete search history.

(56) References Cited

U.S. PATENT DOCUMENTS

| | | | |
|---|---|---|---|
| 2014/0306213 A1* | 10/2014 | Sato | H01L 51/5072 257/40 |
| 2014/0374728 A1* | 12/2014 | Adamovich | H05B 33/10 257/40 |
| 2015/0034923 A1* | 2/2015 | Kim | H01L 27/3209 257/40 |
| 2015/0280160 A1* | 10/2015 | Lee | H01L 27/3211 257/40 |
| 2018/0099968 A1 | 4/2018 | Zhengchuan et al. | |
| 2018/0170914 A1* | 6/2018 | Miyata | C07D 251/24 |

FOREIGN PATENT DOCUMENTS

| | | | | |
|---|---|---|---|---|
| CN | 107868090 A | | 4/2018 | |
| CN | 106316924 B | * | 1/2020 | .......... C07D 209/82 |
| JP | 2001313179 A | * | 11/2001 | |
| WO | 2011071255 A1 | | 6/2011 | |

OTHER PUBLICATIONS

Dongcheng Chen "Nitrogen heterocycle-containing materials for highly efficient phosphorescent OLEDs with low operating voltage" J. Mater. Chem. C, 2014, 2,9565 (Year: 2014).*

Extended European Search Report issued in corresponding European Patent Application No. 19196693 dated Jan. 21, 2020.

Shao-Yu et al., Virtual Screening of Hole Transport, Electron Transport, and Host Layers for Effective OLED Design, J. Chem. Information and Modeling 58: 2440-2449 (2018).

Office Action issued in corresponding Chinese Patent Application No. 201910911681 dated May 9, 2022.

* cited by examiner

ORGANIC COMPOUND, ORGANIC LIGHT-EMITTING DIODE AND ORGANIC LIGHT-EMITTING DEVICE CONTAINING THE COMPOUND

CROSS-REFERENCE TO RELATED APPLICATIONS

This application claims the priority benefit under 35 U.S.C. § 119(a) of Korean Patent Application No. 10-2018-0120461, filed in the Republic of Korea on Oct. 10, 2018, which is incorporated herein by reference in its entirety.

BACKGROUND

Technical Field

The present disclosure relates to an organic compound, and more specifically, to an organic compound enhancing luminous efficiency and color purity, an organic light-emitting diode and an organic light-emitting device including the compound.

Description of the Related Art

As display devices become larger, there exists a need for a flat display device with a lower spacing occupation. Among the flat display devices, a display device using an organic light-emitting diode (OLED) has come into the spotlight.

In the OLED, when electrical charges are injected into an emission layer between an electron injection electrode (i.e., cathode) and a hole injection electrode (i.e., anode), electrical charges are combined to be paired, and then emit light as the combined electrical charges disappear.

The OLED can be formed even on a flexible transparent substrate such as a plastic substrate. In addition, the OLED can be driven at a lower voltage of 10 V or less. Moreover, the OLED has relatively lower power consumption for driving compared to plasma display panels and inorganic electroluminescent devices, and color purity thereof is very high. Further, since the OLED can display various colors such as green, blue, red and the like, the OLED display device has attracted attention as a next-generation display device that can replace a liquid crystal display device (LCD).

BRIEF SUMMARY

Accordingly, the present disclosure is directed to an organic compound, an organic light-emitting diode and an organic light-emitting device including the organic compound that substantially obviate one or more of the problems due to the limitations and disadvantages of the related art.

An object of the present disclosure is to provide an organic compound, an organic light-emitting diode and an organic light-emitting device that can enhance luminous efficiency and implement efficient luminescence at a lower driving voltage.

Another object of the present disclosure is to provide an organic light-emitting diode and an organic light-emitting device each of which has high color purity.

Additional features and advantages of the disclosure will be set forth in the description which follows, and in part will be apparent from the description, or may be learned by practice of the disclosure. The objectives and other advantages of the disclosure will be realized and attained by the structures particularly pointed out in the written description and claims herein as well as the appended drawings.

According to an aspect, the present disclosure provides an organic compound having a fused heteroaromatic moiety as an electron donor and a tri-pyrimidine moiety as an electron acceptor bonded to the fused heteroaromatic moiety. The organic compound is represented by the following Chemical Formula 1:

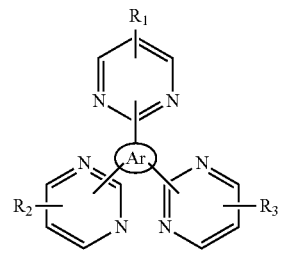

Chemical Formula 1 wherein each of $R_1$ to $R_3$ is independently the following Chemical Formula 2 or the following Chemical Formula 3; and Ar is a $C_5$-$C_{30}$ arylene group,

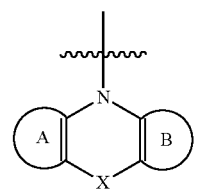

Chemical Formula 2

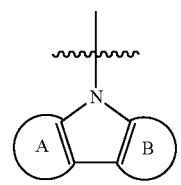

Chemical Formula 3 wherein each of A and B is independently a unsubstituted or substituted $C_5$-$C_{30}$ aromatic group or a unsubstituted or substituted $C_4$-$C_{30}$ heteroaromatic group fused with a center ring; X in Chemical Formula 2 is $CR_4R_5$, $NR_6$, O or S, wherein each of $R_4$ and $R_5$ is independently hydrogen, a $C_1$-$C_{20}$ alkyl group, a $C_1$-$C_{20}$ alkoxy group, a $C_1$-$C_{20}$ alkylamino group, a $C_5$-$C_{30}$ aryl group, a $C_4$-$C_{30}$ heteroaryl group, a $C_5$-$C_{30}$ aryloxyl group, a $C_4$-$C_{30}$ a heteroaryloxyl group, a $C_5$-$C_{30}$ arylamino group or a $C_4$-$C_{30}$ heteroaryl amino group, or $R_4$ and $R_5$ form a $C_5$-$C_{30}$ spiro aromatic ring or a $C_4$-$C_{30}$ heteroaromatic ring; $R_6$ is hydrogen, a $C_1$-$C_{20}$ alkyl group, a $C_1$-$C_{20}$ alkoxy group, a $C_1$-$C_{20}$ alkylamino group, a $C_5$-$C_{30}$ aryl group, a $C_4$-$C_{30}$ heteroaryl group, a $C_5$-$C_{30}$ aryloxyl group, a $C_4$-$C_{30}$ heteroaryloxyl group, a $C_5$-$C_{30}$ arylamino group or a $C_4$-$C_{30}$ heteroaryl amino group.

According to another aspect, the present disclosure provides an organic light-emitting diode (OLED) that comprises the organic compound in an emitting material layer.

The organic light-emitting diode may comprise: a first electrode; a second electrode facing the first electrode; and an emitting material layer between the first and second electrodes, wherein the emitting material layer comprises the organic compound.

In one or more embodiments, the emitting material layer further includes a first host, wherein the organic compound is used as a first dopant.

In one or more embodiments, an energy bandgap between a Highest Occupied Molecular Orbital energy level of the first host and a Highest Occupied Molecular Orbital energy level of the first dopant or an energy bandgap between a Lowest Unoccupied Molecular Orbital energy level of the first host and a Lowest Unoccupied Molecular Orbital energy level of the first dopant is equal to or less than about 0.5 eV.

In one or more embodiments, each of an excited state singlet energy level and an excited state triplet energy level of the first host is higher than an excited state singlet energy level and an excited state triplet energy level of the first dopant, respectively.

In one or more embodiments, an energy bandgap between an excited state single energy level and an excited state triplet energy level of the first dopant is equal to or less than about 0.3 eV.

In one or more embodiments, the emitting material layer further comprises a second dopant.

In one or more embodiments, an excited state triplet energy level of the first dopant is lower than an excited state triplet energy level of the first host and an excited state singlet energy level of the first dopant is higher than an excited state singlet energy level of the second dopant.

In one or more embodiments, the emitting material layer includes a first emitting material layer between the first and second electrode and a second emitting material layer between the first electrode and the first emitting material layer or between the first emitting material layer and the second electrode.

In one or more embodiments, the first emitting material layer includes a first host and a first dopant, wherein the first dopant comprises the organic compound.

In one or more embodiments, the second emitting material layer includes a second host and a second dopant.

In one or more embodiments, an excited state singlet energy level of the first dopant is higher than an excited state singlet energy level of the second dopant.

In one or more embodiments, each of an excited state singlet energy level and an excited state triplet energy level of the first host is higher than an excited state singlet energy level and an excited state triplet energy level of the first dopant, respectively, and an excited state singlet energy level of the second host is higher than an excited state singlet energy level of the second dopant.

In one or more embodiments, the second emitting material layer is disposed between the first electrode and the first emitting material layer, and further comprising an electron blocking layer disposed between the first electrode and the second emitting material layer.

In one or more embodiments, the second host is formed as the same material as the electron blocking layer.

In one or more embodiments, the second emitting material layer is disposed between the first emitting material layer and the second electrode, and further comprising a hole blocking layer between the second emitting material layer and the second electrode.

In one or more embodiments, the second host is formed as the same material as the hole blocking layer.

In one or more embodiments, the emitting material layer further comprises a third emitting material layer disposed oppositely to the second emitting material layer with respect to the first emitting material layer.

In one or more embodiments, the first emitting material layer comprises a first host and a first dopant, wherein the first dopant comprises the organic compound.

In one or more embodiments, the second emitting material layer comprise a second host and a second dopant and the third emitting material layer comprises a third host and a third dopant.

In one or more embodiments, an excited state singlet energy level of the first dopant is higher than excited state singlet energy levels of the second and third dopants.

In one or more embodiments, each of an excited state singlet energy level and an excited state triplet energy level of the first host is higher than an excited state singlet energy level and an excited state triplet energy level of the first dopant, respectively, an excited state singlet energy level of the second host is higher than an excited state singlet energy level of the second dopant, and an excited state singlet energy level of the third host is higher than an excited state singlet energy level of the third dopant.

In one or more embodiments, the second emitting material layer is disposed between the first electrode and the first emitting material layer and the third emitting material layer is disposed between the first emitting material layer and the second electrode, and further comprising an electron blocking layer disposed between the first electrode and the second emitting material layer.

In one or more embodiments, the second host is formed as the same material as the electron blocking layer.

In one or more embodiments, the second emitting material layer is disposed between the first electrode and the first emitting material layer and the third emitting material layer is disposed between the first emitting material layer and the second electrode, and further comprising a hole blocking layer disposed between the second electrode and the third emitting material layer.

In one or more embodiments, the third host is formed as the same material as the hole blocking layer.

In one or more embodiments, the organic light-emitting diode further comprises an electron blocking layer disposed between the first electrode and the second emitting material layer.

In one or more embodiments, the second host is formed as the same material as the electron blocking layer.

According to still another aspect, the present disclosure provides an organic light-emitting device that comprises a substrate and the OLED disposed over the substrate, as described above.

In one or more embodiments, the organic light-emitting device is an organic light-emitting display device.

It is to be understood that both the foregoing general description and the following detailed description are only examples and are intended to provide further explanation of the disclosure as claimed.

BRIEF DESCRIPTION OF THE DRAWINGS

The accompanying drawings, which are included to provide a further understanding of the disclosure, illustrate implementations of the disclosure and together with the description serve to explain the principles of various embodiments of the disclosure.

DETAILED DESCRIPTION

Figure 1:
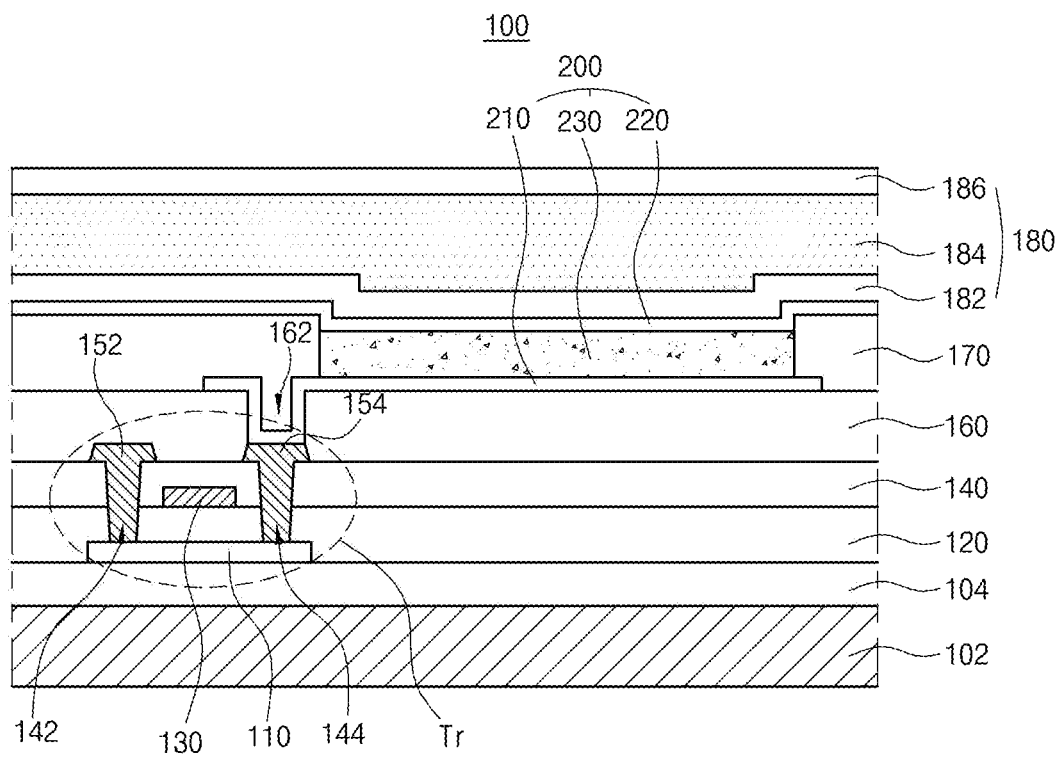
FIG. 1 is a schematic cross-sectional view illustrating an organic light-emitting display device of the present disclosure.

Reference will now be made in detail to various aspects of the disclosure, examples of which are illustrated in the accompanying drawings.

Organic Compound

An organic compound of the present disclosure has a fused heteroaromatic moiety, which can act as an electron donor, and a moiety including three pyrimidines, i.e., a tri-pyrimidine moiety, which can as an electron acceptor and each of which is bonded together via an arylene group, bonded to the fused heteroaromatic moiety. The organic compound of the present disclosure may be represented by the following Chemical Formula 1:

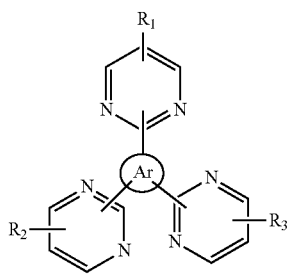

Chemical Formula 1

In Chemical Formula 1, each of $R_1$ to $R_3$ has independently the following Chemical Formula 2 or the following Chemical Formula 3. Ar is a $C_5$-$C_{30}$ arylene group.

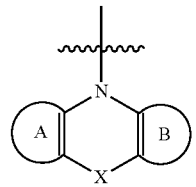

Chemical Formula 2

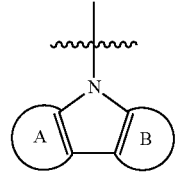

Chemical Formula 3

In Chemical Formulae 2 and 3, each of A and B is independently a unsubstituted or substituted $C_5$-$C_{30}$ aromatic group or $C_4$-$C_{30}$ heteroaromatic group fused with a center ring.

In Chemical Formula 2, X is $CR_4R_5$, $NR_6$, O or S, wherein each of $R_4$ and $R_5$ is independently hydrogen, a $C_1$-$C_{20}$ alkyl group, a $C_1$-$C_{20}$ alkoxy group, a $C_1$-$C_{20}$ alkylamino group, a $C_5$-$C_{30}$ aryl group, a $C_4$-$C_{30}$ heteroaryl group, a $C_5$-$C_{30}$ aryloxyl group, a $C_4$-$C_{30}$ heteroaryloxyl group, a $C_5$-$C_{30}$ aryl-amino group or a $C_4$-$C_{30}$ heteroaryl amino group, or $R_4$ and $R_5$ form a $C_5$-$C_{30}$ spiro aromatic ring or a $C_4$-$C_{30}$ spiro heteroaromatic ring; $R_6$ is hydrogen, a $C_1$-$C_{20}$ alkyl group, a $C_1$-$C_{20}$ alkoxy group, a $C_1$-$C_{20}$ alkylamino group, a $C_5$-$C_{30}$ aryl group, a $C_4$-$C_{30}$ heteroaryl group, a $C_5$-$C_{30}$ aryloxyl group, a $C_4$-$C_{30}$ heteroaryloxyl group, a $C_5$-$C_{30}$ arylamino group or a $C_4$-$C_{30}$ heteroaryl amino group.

As used herein, the term "unsubstituted" means that a hydrogen atom is bonded, and in this case a hydrogen atom comprises protium, deuterium and tritium.

As used herein, the term "hetero" as used in "heteroaromatic ring", "heteroaromatic group", "heteroalicyclic ring", "heterocyclic alkyl group", "heteroaryl group", "heteroaralkyl group", "heteroaryloxyl group", "heteroaryl amino group", "heteroarylene group", "heteroaralkylene group", "heteroaryloxylene group", and the like means that at least one carbon atom, for example 1 to 5 carbon atoms, forming such aromatic or alicyclic rings, are substituted with at least one hetero atom selected from the group consisting of N, O, S and combinations thereof.

In one embodiment, the $C_5$-$C_{30}$ aromatic group of $R_4$ to $R_6$ defined in the Chemical Formula 2 may comprise, but is not limited to, a unsubstituted or substituted $C_5$-$C_{30}$ aryl group, a unsubstituted or substituted $C_5$-$C_{30}$ aralkyl group, a unsubstituted or substituted $C_5$-$C_{30}$ aryloxyl group and/or a unsubstituted or substituted $C_5$-$C_{30}$ arylamino group. For example, the $C_5$-$C_{30}$ aryl group of $R_4$ to $R_6$ in Chemical Formula 2 may comprise, but is not limited to, a non-fused or fused aryl group such as phenyl, biphenyl, terphenyl, naphthyl, anthracenyl, indenyl, indacenyl, phenalenyl, phenanthrenyl, benzo-phenanthrenyl, dibenzo-phenathrenyl, azulenyl, pyreneyl, fluoranthenyl, chrysenyl, tetraphenyl, tetracenyl, pleiadenyl, pycenyl, pentaphenyl, pentacenyl, fluorenyl, indeno-indenyl, indeno-fluorenyl and/or spiro-fluorenyl (where $R_4$ and $R_5$ form a $C_4$-$C_{30}$ spiro aromatic or heteroaromatic ring), each of which may be unsubstituted or substituted.

In another embodiment, the $C_4$-$C_{30}$ heteroaromatic group of $R_4$ to $R_6$ may comprise, but is not limited to, a $C_4$-$C_{30}$ heteroaromatic group unsubstituted or substituted with at least one of a $C_1$-$C_{10}$ alkyl group and a $C_4$-$C_{30}$ aromatic or heteroaromatic group. For example, the $C_4$-$C_{30}$ heteroaromatic group of $R_4$ to $R_6$ may be selected from, but is not limited to, the group consisting of a $C_4$-$C_{30}$ heteroaryl group, a $C_4$-$C_{30}$ heteroaralkyl group, a $C_4$-$C_{30}$ heteroaryloxyl group and a $C_4$-$C_{30}$ heteroaryl amino group. In this case, each of the heteroaryl group, the heteroaralkyl group, the heteroaryloxyl group and the heteroaryl amino group may be independently unsubstituted or substituted with at least one of a $C_1$-$C_{10}$ alkyl group and a $C_4$-$C_{30}$ aromatic or heteroaromatic group.

For example, the $C_4$-$C_{30}$ heteroaromatic group of $R_4$ to $R_6$ may comprise, but is not limited to, a unfused or fused heteroaryl group such as furanyl, thiophenyl, pyrrolyl, pyridyl, pyridinyl, pyrimidyl, pyrimidinyl, pyrazinyl, pyridazinyl, triazinyl, tetrazinyl, imidazolyl, pyrazolyl, indolyl, carbazolyl, benzocarbazolyl, dibenzocarbazolyl, indolocarbazolyl, indenocarbazolyl, benzofurannocarbazolyl, benzothienocarbazolyl, quinolinyl, iso-quinolinyl, phthalazinly, quinoxalinyl, cinnolinyl, quinazolinyl, benzoquinolinyl, beznoiso-quinolinyl, benzoquinoxalinyl, benzoquinazolinyl, acridinyl, phenanthrolyl, pyranyl, oxazinyl, oxazolyl, iso-oxazolyl, oxadiazolyl, triazolyl, dioxinyl, benzofuranyl, dibenzofuranyl, thiopyranyl, thiazinyl, benzothiophenyl, dibenzothiophenyl, thiazolyl, iso-thiazolyl, xanthenyl, spiro-xanthenyl, acridinyl, dihydro-acridinyl substituted with at least one $C_1$-$C_{10}$ alkyl group, spiro-acridinyl, phenazinyl, spiro-phenazinyl, thiophenzinyl, spiro-thiophenazinyl, phenoxazinyl, thisphenzinyl, and the like.

In addition, each of "A" and "B" in Chemical Formulae 2 and 3 may comprise independently a $C_5$-$C_{30}$ aromatic ring or a $C_4$-$C_{30}$ heteroaromatic ring fused with the 6-membered or the 5-membered heteroaromatic ring in the center. In one exemplary embodiment, each of "A" and "B" in Chemical Formulae 2 and 3 may include 1 to 3, preferably 1 or 2 fused aromatic or heteroaromatic rings. When the number of the aromatic or heteroaromatic rings forming respectively "A" and "B" is more than four, the entire organic compound may have such long conjugated structures that its energy band gap may be significantly lowered. For example, each of "A" and "B" in Chemical Formulae 2 and 3 may include, but is not limited to, aromatic rings such as a benzene ring, a naphthyl ring, a biphenyl ring, an anthracene ring, an indene ring, an indacene ring, a phenalene ring, a phenathrene ring, an azulene ring or a fluorene ring, respectively, fused with the 5-membered or 6-membered heteroaromatic ring in the center.

In another embodiment, each of the "A" and "B" in Chemical Formulae 2 and 3 may comprise, but is not limited to, heteroaromatic rings such as a furane ring, a thiophenyl ring, a pyridine ring, a pyrimidine ring, a pyrazine ring, a pyridazine ring, a triazine ring, an imidazole ring, a pyrazole ring, an indole ring, a carbazole ring, a quinoline ring, an isoquinoline ring, a phthalazine ring, a quinoxaline ring, a cinnoline ring, a quinazoline ring, a benzoquinoline ring, a beznoiso-quinoline ring, a benzoquinoxaline ring, an acridine ring, a phenanthrole ring, a phenazine ring, a phenoxazine ring, a phenothiazole ring, a pyrazine ring, an oxazine ring, an oxazole ring, an iso-oxazole ring, an oxadiazole ring, a triazole ring, a dioxine ring, a benzofurane ring, a dibenzofurane ring, a thiopyrane ring, a thiazine ring, a thiophenyl ring, a beznothiophenyl ring or a dibenzothiophenyl ring, respectively, fused with the 5-membered or 6-membered heteroaromatic ring in the center.

In an exemplary embodiment, "Ar" linking together the tri-pyrimidine moiety in Chemical Formula 1 may be selected from the group, but is not limited to, consisting of phenylene, biphenylene, terphenylene, tetraphenylene, indenylene, naphthylene, azulenylene, indacenylene, acenaphthylene, fluorenylene, spiro-fluorenylene, phenalenylene, phenanthrenylene, anthracenylene, fluoranthrenylene, triphenylenylene, pyrenylene, chrysenylene, naphthacenylene, picenylene, perylenylene, pentaphenylene and hexacenylene.

The organic compound represented by Chemical Formulae 1 to 3 has a fused heteroaromatic moiety including at least one nitrogen atom as an electron donor and a tri-pyrimidine moiety as an electron acceptor bonded to the fused heteroaromatic moiety. The organic compound has an increased dihedral angle between the electron donor and the electron acceptor as a sterical hindrance between the electron donor and the electron acceptor increase. Owing to the formation of conjugation structure between those moieties, the organic compound can divide into a Highest Occupied Molecular Orbital (HOMO) state and a Lowest Unoccupied Molecular Orbital (LUMO) state with ease. In addition, since the organic compound has increased dipole moments within the molecule owing to a dipole formation between the electron donor and the electron acceptor, it is possible to enhance luminous efficiency of a light-emitting diode using the organic compound.

Further, the organic compound has a limited conformational structure owing to the fused heteroaromatic moiety having a large sterical hindrance. Therefore, the organic compound enables the OLED to lower energy loss and to improve color purity having luminescence spectra of particular ranges since the conformational structure of the organic compound is not changed by emitting light. Moreover, it is possible to drive the OLED at a lower voltage so that the OLED may decrease its consumption power, and to decrease loads such as Joule's heat applied into the OLED so that the OLED may have an increased luminous life span, in the case of using the compound in the OLED.

In one exemplary embodiment, when the number of the aromatic or heteroaromatic rings forming "Ar", which bonds together the tri-pyrimidine moiety, becomes larger, the entire organic compound may have such long conjugated structures that its energy bandgap may be significantly lowered. As an example, "Ar" in Chemical Formula 1 may comprise 1 to 3, preferably 1 or 2, aromatic or heteroaromatic rings. In addition, "Ar" may comprise a 5-membered, 6-membered or 7-membered, preferably a 6-membered, aromatic or heteroaromatic ring with regard to injection or transportation of holes and/or electrons. For example, "Ar" may comprise, but is not limited to, phenylene, anthracenylene or biphenylene.

In one exemplary embodiment, the organic compound represented by Chemical Formulae 1 to 3 may have the following structure of Chemical Formula 4:

Chemical Formula 4

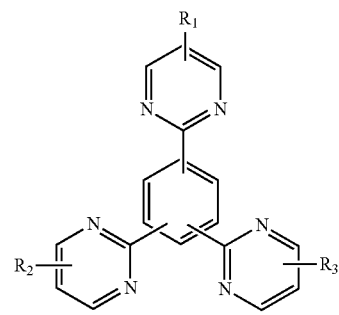

In Chemical Formula 4, each of $R_1$ to $R_3$ is independently the same as defined in Chemical Formula 1.

In one embodiment, the center phenylene linker "Ar" defined in Chemical Formula 4 may be linked to a carbon atom between two nitrogen atoms in each of the pyrimidine ring. In this case, the organic compound has an increased sterical hindrance between the fused heteroaromatic moiety, i.e., $R_1$ to $R_3$ as an electron donor and the tri-pyrimidine moiety as an electron acceptor, as the electron donor is linked to the electron acceptor with planar conformation. Therefore, the organic compound can be divided into a HOMO state and a LUMO state and can have decreased energy bandgap between the triplet state energy level and the singlet state energy level. As an example, the organic compound represented by Chemical Formula 4 may have the following structure of Chemical Formula 5:

Chemical Formula 5

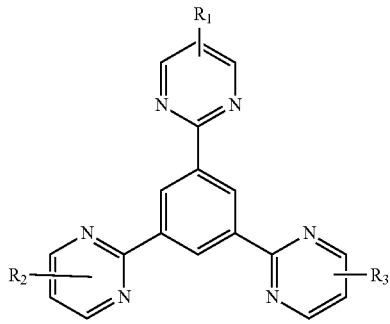

In Chemical Formula 5, each of $R_1$ to $R_3$ is independently the same as defined in Chemical Formula 1

In another exemplary embodiment, the fused heteroaromatic moiety defined in Chemical Formula 2 may include an acridine moiety. As an example, the fused heteroaromatic moiety in Chemical Formula 2 including the acridine moiety may have the following structure of Chemical Formula 6:

Chemical Formula 6

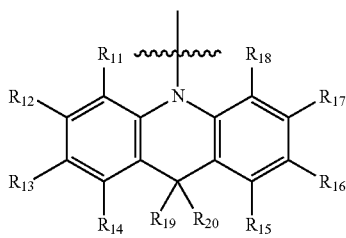

In Chemical Formula 6, each of $R_{11}$ to $R_{18}$ is independently hydrogen, silyl group, $C_1$-$C_{20}$ alkyl group, $C_1$-$C_{20}$ alkoxy group, $C_1$-$C_{20}$ alkylamino group, $C_5$-$C_{30}$ aryl group, $C_4$-$C_{30}$ heteroaryl group, $C_5$-$C_{30}$ aryloxyl group, $C_4$-$C_{30}$ heteroaryloxyl group, $C_5$-$C_{30}$ arylamino group or $C_4$-$C_{30}$ heteroaryl amino group, or two adjacent groups among $R_{11}$ to $R_{18}$ form $C_4$-$C_{30}$ fused aromatic or heteroaromatic ring unsubstituted or substituted with $C_4$-$C_{30}$ aromatic or heteroaromatic group. Each of $R_{19}$ and $R_{20}$ is independently hydrogen, $C_1$-$C_{20}$ alkyl group, $C_1$-$C_{20}$ alkoxy group, $C_1$-$C_{20}$ alkylamino group, $C_5$-$C_{30}$ aryl group, $C_4$-$C_{30}$ heteroaryl group, $C_5$-$C_{30}$ aryloxyl group, $C_4$-$C_{30}$ heteroaryloxyl group, $C_5$-$C_{30}$ arylamino group or $C_4$-$C_{30}$ heteroaryl amino group, or $R_{19}$ and $R_{20}$ form a $C_4$-$C_{30}$ spiro aromatic or heteroaromatic ring.

Each of the aryl or heteroaryl group of $R_{11}$ to $R_{20}$ in Chemical Formula 6 may be the same as each of the aryl or heteroaryl group of each of $R_4$ to $R_6$ in Chemical Formula 2, as described above. As an example, each of $R_{11}$ to $R_{20}$ may comprise independently hydrogen (including protium, deuterium and tritium); linear or branched $C_1$-$C_{10}$ alkyl (e.g., methyl, ethyl, propyl, iso-propyl, butyl and/or iso-butyl); $C_5$-$C_{30}$ aryl (e.g., phenyl, biphenyl and/or naphthyl) unsubstituted or substituted with linear or branched $C_1$-$C_{10}$ alkyl group, $C_5$-$C_{30}$ aryl group and/or $C_4$-$C_{30}$ heteroaryl group; and $C_4$-$C_{30}$ heteroaryl (e.g., carbazolyl, acridinyl, phenazinly, phenoxazinyl and/or phenothiazinyl) unsubstituted or substituted with linear or branched $C_1$-$C_{10}$ alkyl group, $C_5$-$C_{30}$ aryl group and/or $C_4$-$C_{30}$ heteroaryl group. In one exemplary embodiment, $R_{19}$ and $R_{20}$ may form a spiro aromatic ring such as spiro-fluorene structure.

In an alternative embodiment, in case adjacent two groups among $R_{11}$ to $R_{18}$ forms a fused aromatic ring, the fused aromatic ring may comprise, but is not limited to, a phenyl ring, a naphthalene ring, an indene ring, a pyridine ring, a pyrimidine ring, a indole ring, and the like, each of which may be unsubstituted or substituted with at least one of linear or branched $C_1$-$C_{20}$ alkyl group, preferably a linear or branched $C_1$-$C_{10}$ alkyl group, $C_5$-$C_{30}$ aryl group, preferably $C_5$-$C_{20}$ aryl group (e.g., phenyl group and/or naphthyl group), $C_4$-$C_{30}$ heteroaryl group, preferably $C_4$-$C_{20}$ heteroaryl group (e.g., pyridyl group, pyrimidyl group and/or carbazolyl group) and combinations thereof. Particularly, the organic compound having the acridine moiety of Chemical Formula 6 may include any one having following structures of Chemical Formula 7:

Chemical Formula 7

Compound 1-1

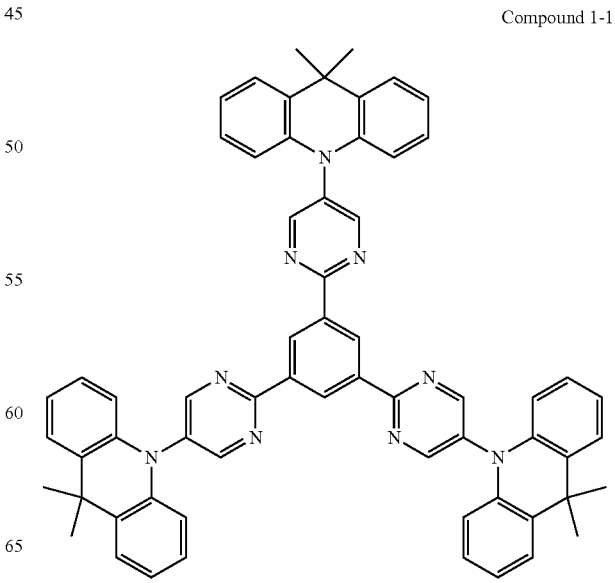

Compound 1-2
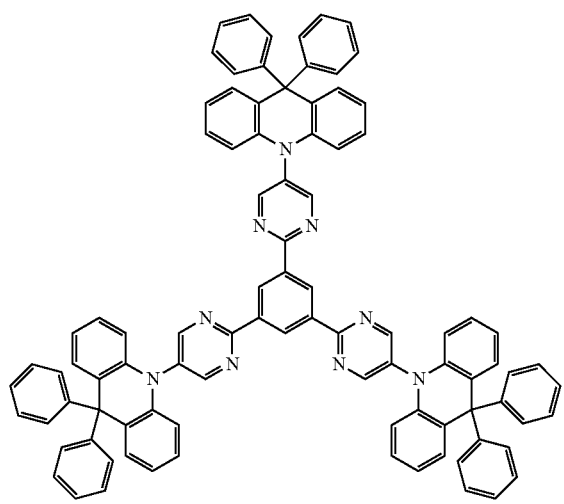
Compound 1-3
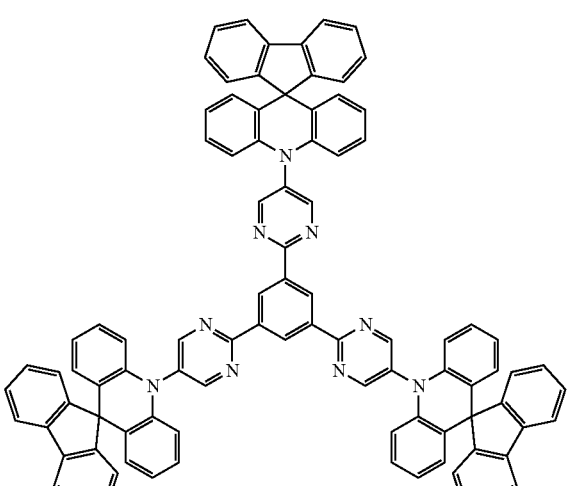
Compound 1-4
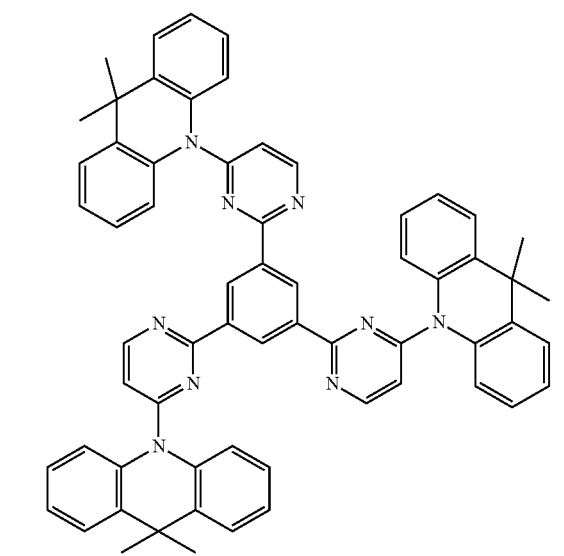
Compound 1-5
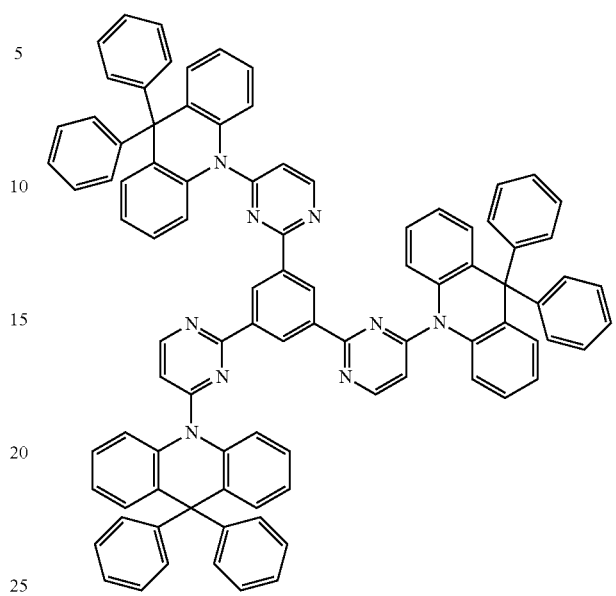
Compound 1-6
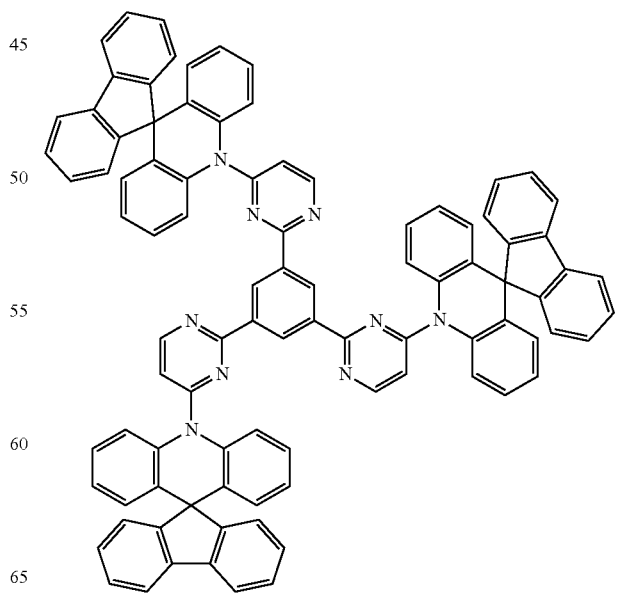

Compound 1-7
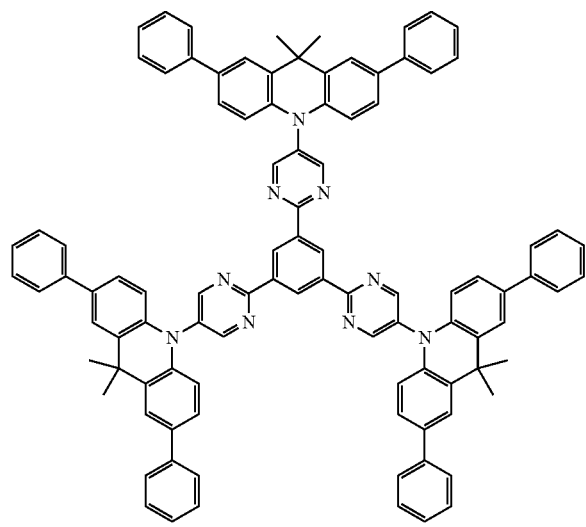
Compound 1-9
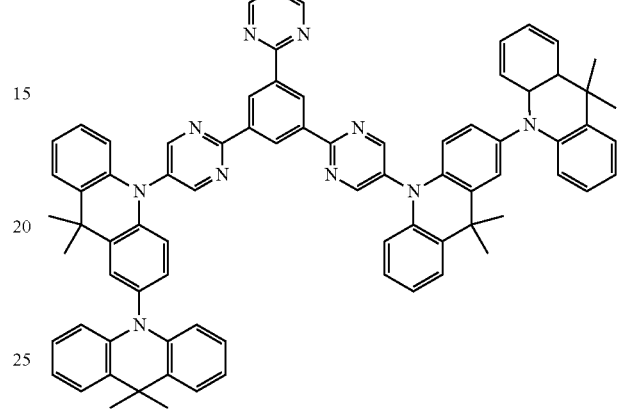
Compound 1-8
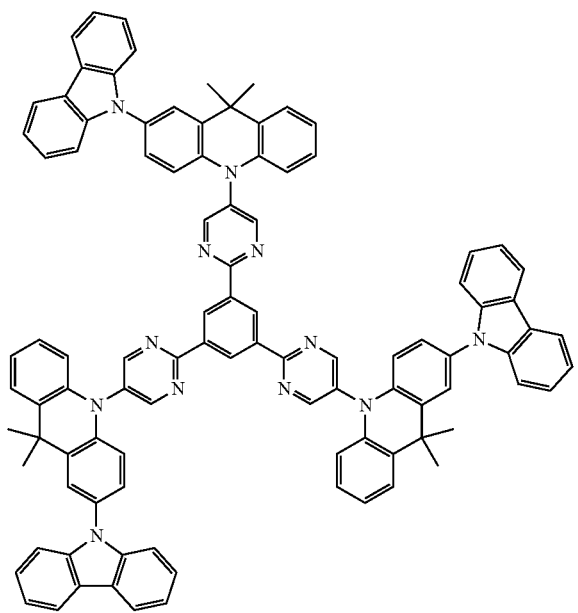
Compound 1-10
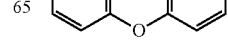

Compound 1-11
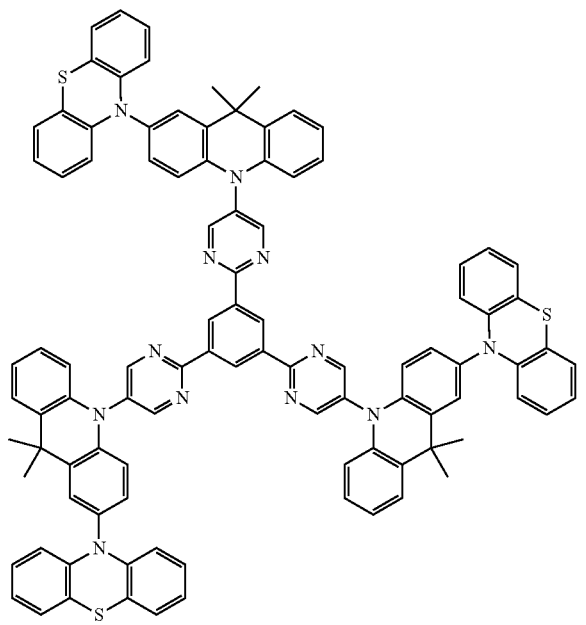
Compound 1-12
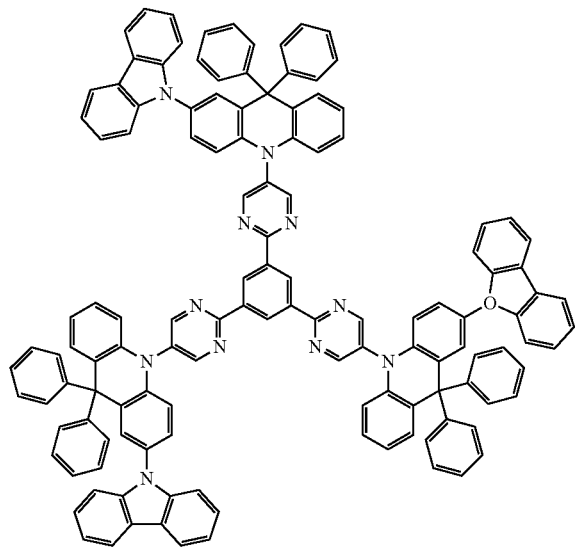
Compound 1-13
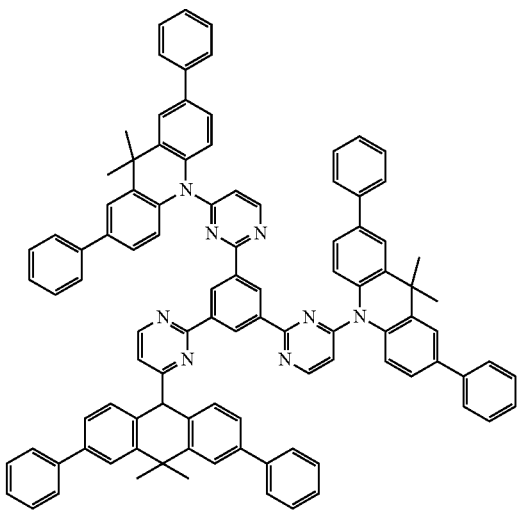
Compound 1-14
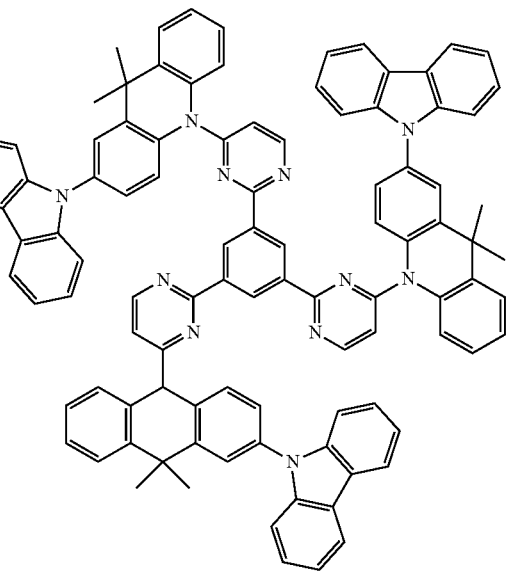

Compound 1-15

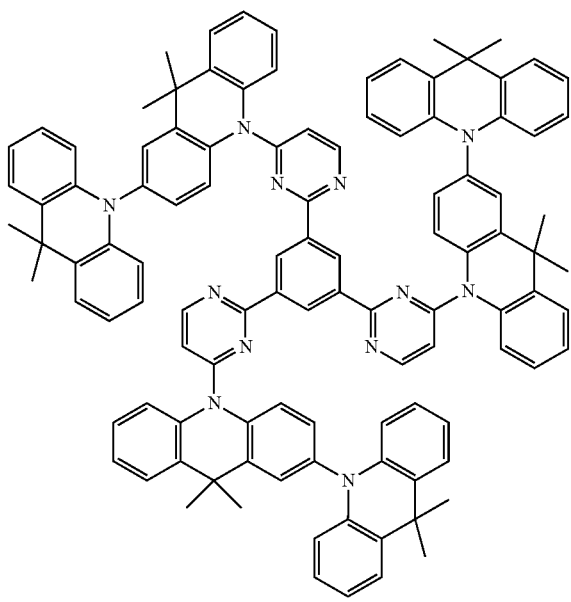

Compound 1-16

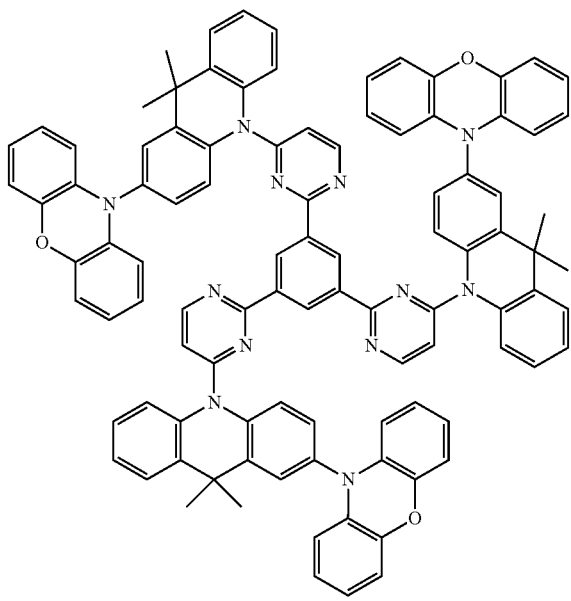

Compound 1-17

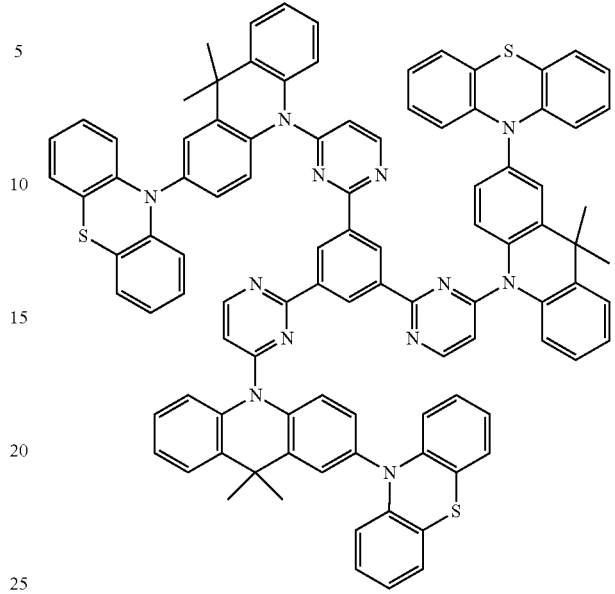

In another exemplary embodiment, the fused heteroaromatic moiety defined in Chemical Formula 2 may include a phenazine moiety, a phenoxazine moiety or a phenothiazine moiety. As an example, the fused heteroaromatic moiety in Chemical Formula 2 including the phenazine, phenoxazine or phenothiazine moiety may have the following structure of Chemical Formula 8:

Chemical Formula 8

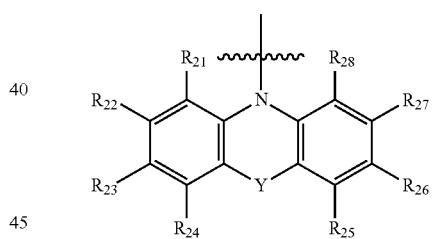

In Chemical Formula 8, each of $R_{21}$ to $R_{28}$ is independently hydrogen, silyl group, $C_1$-$C_{20}$ alkyl group, $C_1$-$C_{20}$ alkoxy group, $C_1$-$C_{20}$ alkylamino group, $C_5$-$C_{30}$ aryl group, $C_4$-$C_{30}$ heteroaryl group, $C_5$-$C_{30}$ aryloxyl group, $C_4$-$C_{30}$ heteroaryloxyl group, $C_5$-$C_{30}$ arylamino group or $C_4$-$C_{30}$ heteroaryl amino group, or two adjacent groups among $R_{21}$ to $R_{28}$ form $C_4$-$C_{30}$ fused aromatic or heteroaromatic ring unsubstituted or substituted with $C_4$-$C_{30}$ aromatic or heteroaromatic group.

Y is $NR_{29}$, O or S, wherein $R_{29}$ is hydrogen, silyl group, $C_1$-$C_{20}$ alkyl group, $C_1$-$C_{20}$ alkoxy group, $C_1$-$C_{20}$ alkylamino group, $C_5$-$C_{30}$ aryl group, $C_4$-$C_{30}$ heteroaryl group, $C_5$-$C_{30}$ aryloxyl group, $C_4$-$C_{30}$ heteroaryloxyl group, $C_5$-$C_{30}$ arylamino group or $C_4$-$C_{30}$ heteroarylamino group.

Each of the aryl or heteroaryl group of $R_{21}$ to $R_{29}$ in Chemical Formula 8 may be the same as each of the aryl or heteroaryl group $R_4$ to $R_6$ in Chemical Formula 2, as described above. As an example, each of $R_{21}$ to $R_{29}$ may comprise independently hydrogen (including protium, deuterium and tritium); linear or branched $C_1$-$C_{10}$ alkyl (e.g., methyl, ethyl, propyl, iso-propyl, butyl and/or iso-butyl); $C_5$-$C_{30}$ aryl (e.g. phenyl, biphenyl and/or naphthyl) unsubstituted or substituted with linear or branched $C_1$-$C_{10}$ alkyl group, $C_5$-$C_{30}$ aryl group and/or $C_4$-$C_{30}$ heteroaryl group; and $C_4$-$C_{30}$ heteroaryl (e.g., carbazolyl, acridinyl, phenazinly, phenoxazinyl and/or phenothiazinyl) unsubstituted or substituted with linear or branched $C_1$-$C_{10}$ alkyl group, $C_5$-$C_{30}$ aryl group and/or $C_4$-$C_{30}$ heteroaryl group.

In an alternative embodiment, the fused aromatic or heteroaromatic ring formed by two adjacent groups among $R_{21}$ to $R_{28}$ in Chemical Formula 8 may be the same as the fussed aromatic or heteroaromatic ring formed by the two adjacent groups among $R_{11}$ to $R_{18}$ in Chemical Formula 6. Particularly, the organic compound having the phenazine, phenoxazine or phenothizine moiety of Chemical Formula 8 may include any one having the following structures of Chemical Formula 9:

Chemical Formula 9

Compound 2-1

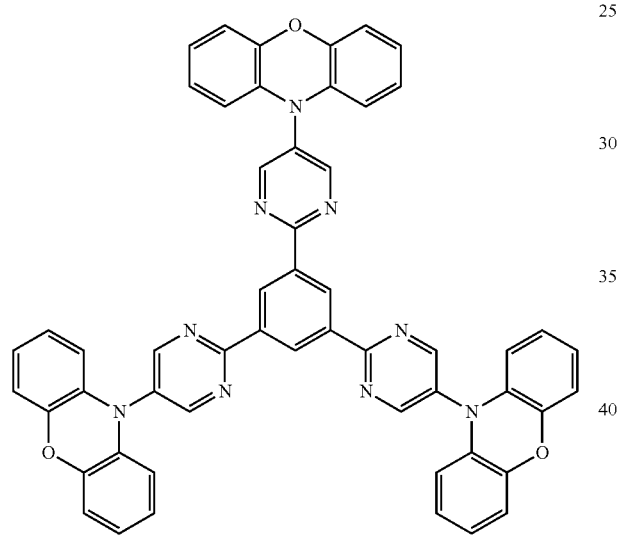

Compound 2-2

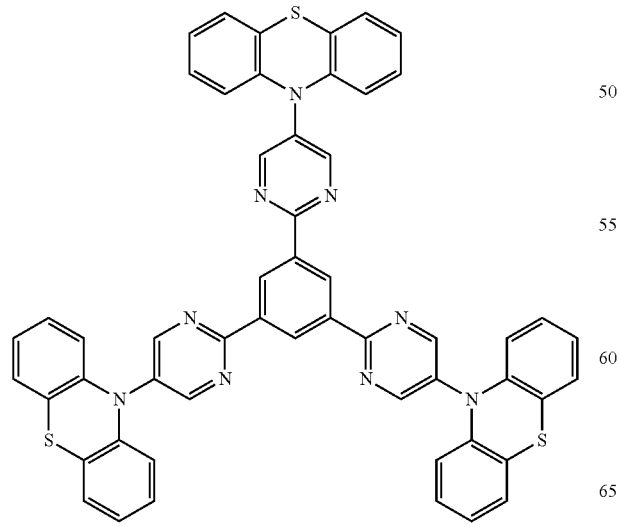

Compound 2-3

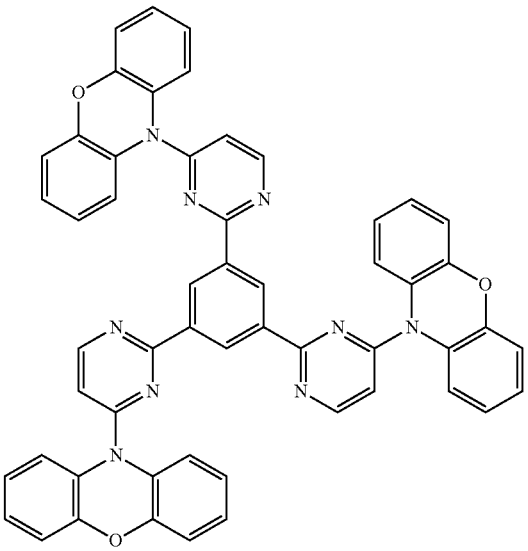

Compound 2-4

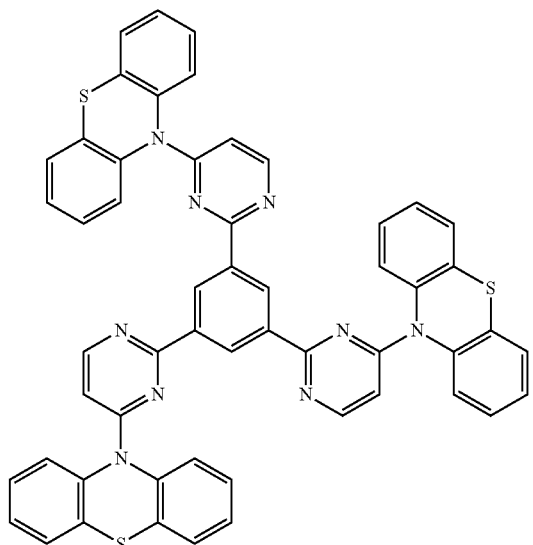

Compound 2-5
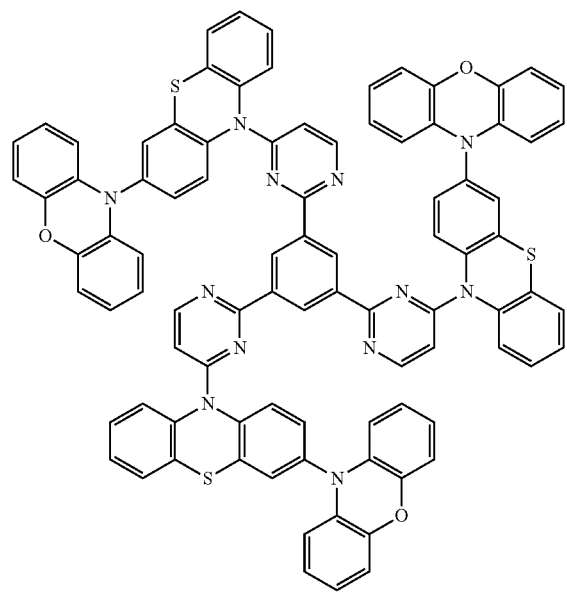
Compound 2-7
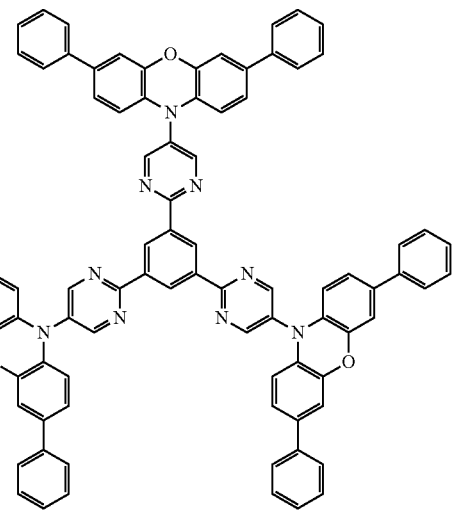
Compound 2-6
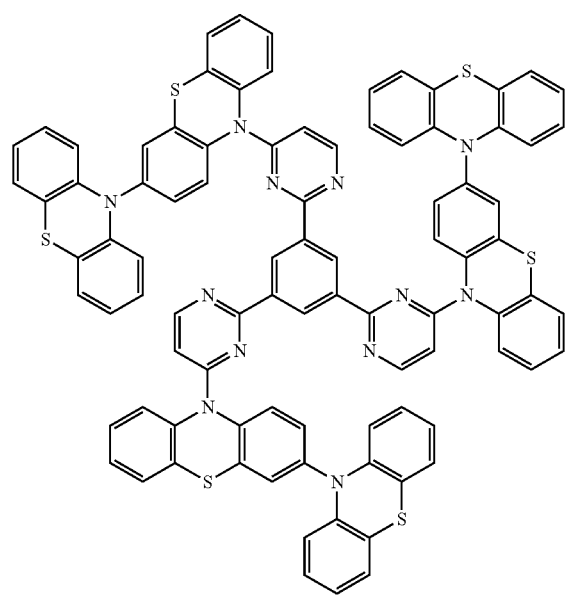
Compound 2-8
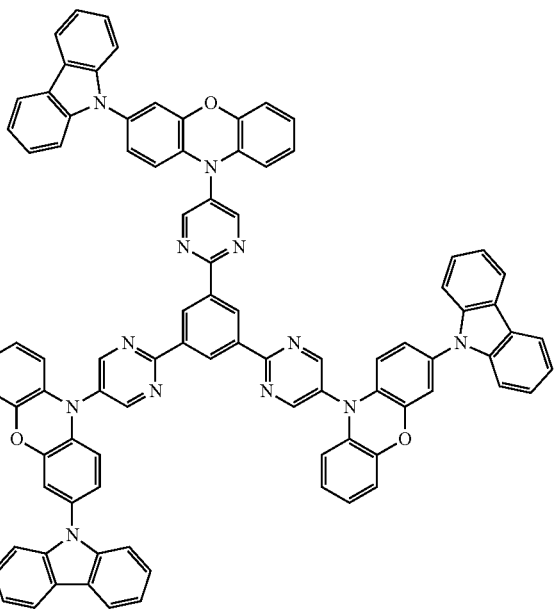

Compound 2-9
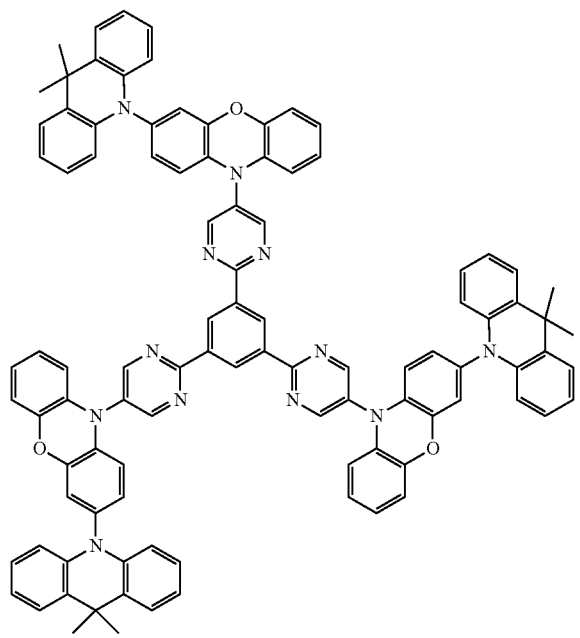
Compound 2-10
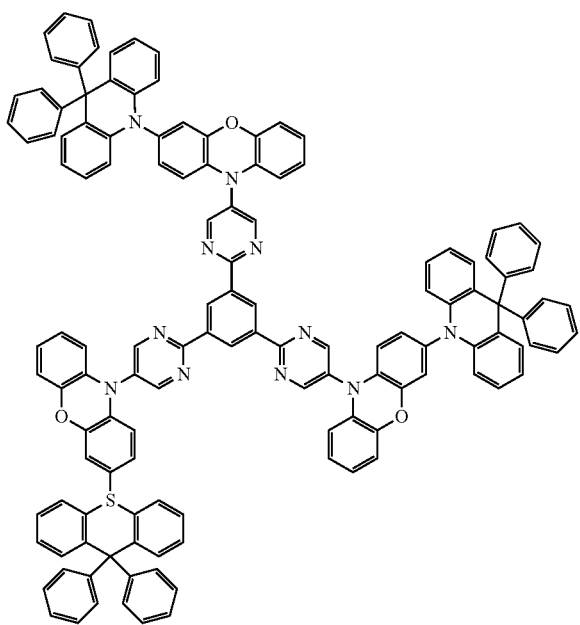
Compound 2-11
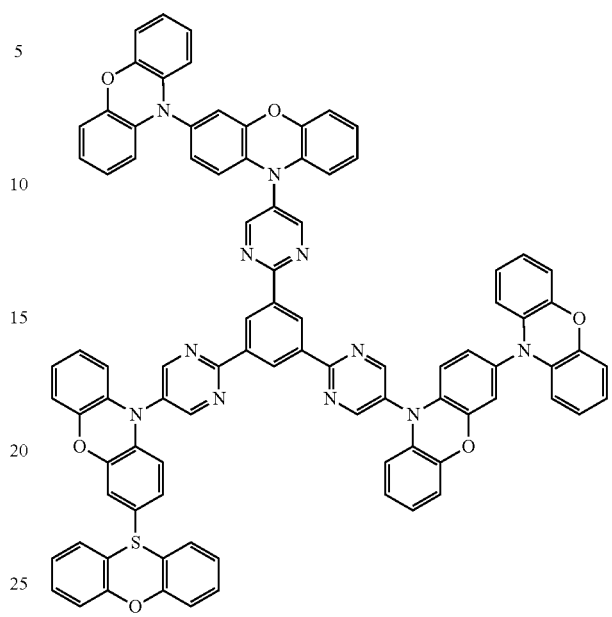
Compound 2-12
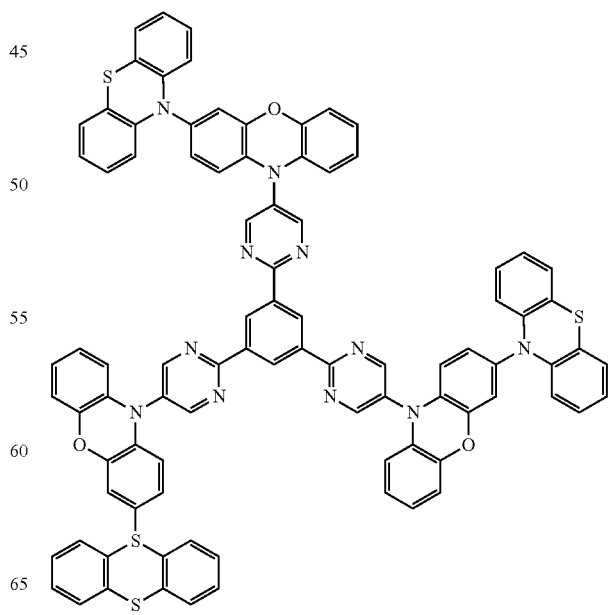

Compound 2-13
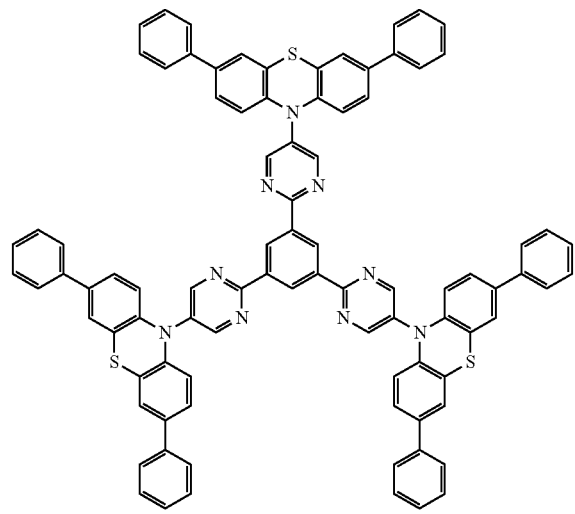
Compound 2-14
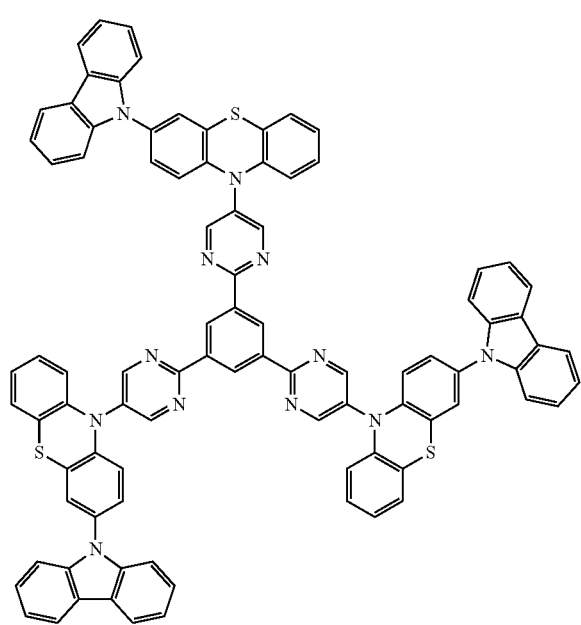
Compound 2-15
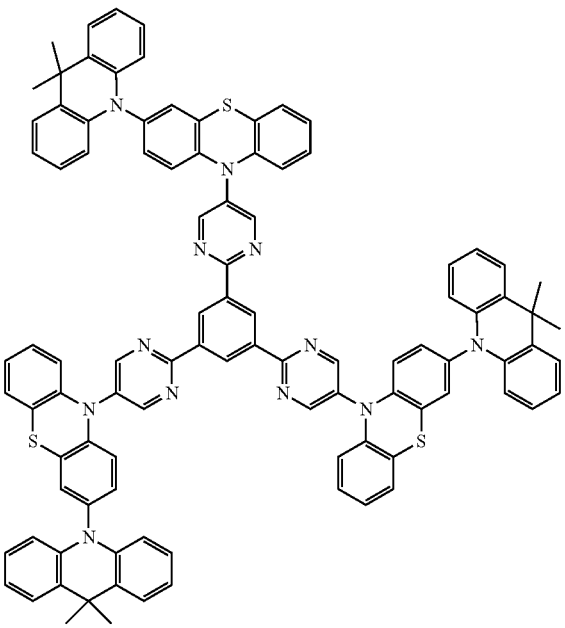
Compound 2-16
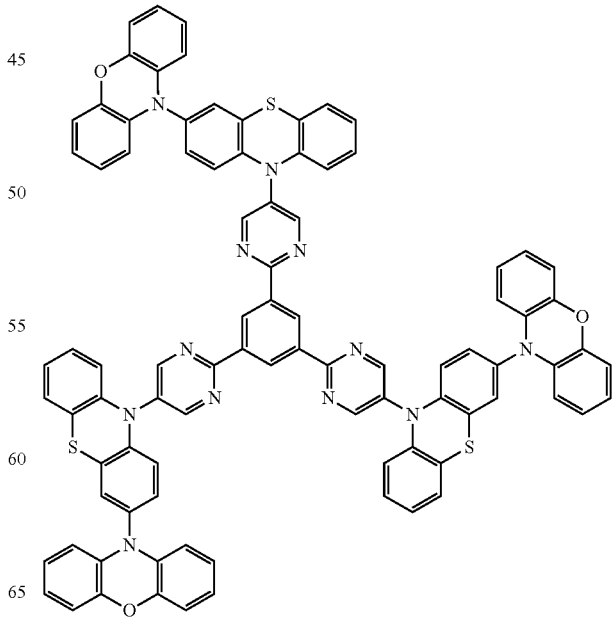

Compound 2-17
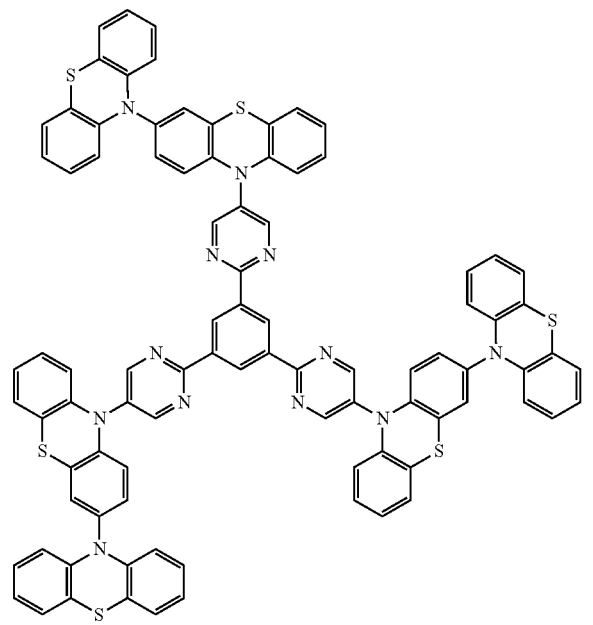
Compound 2-18
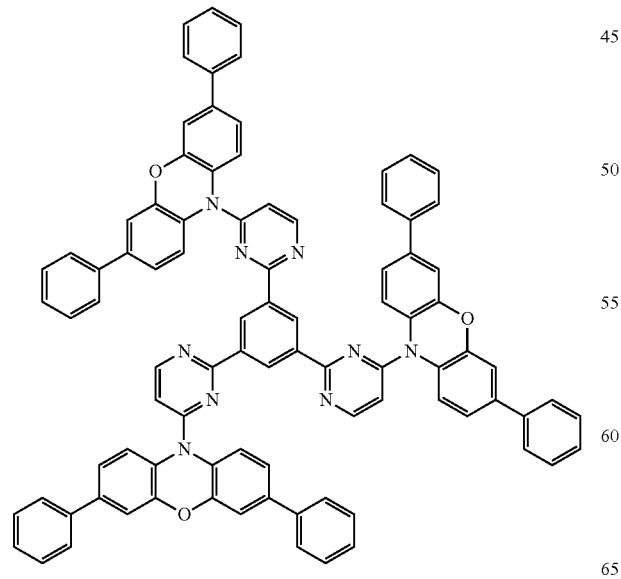
Compound 2-19
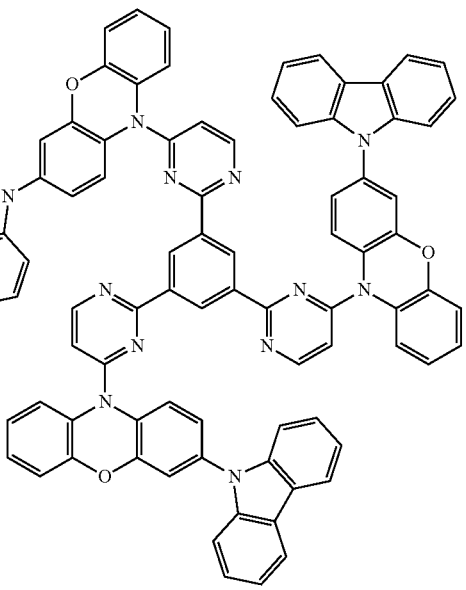
Compound 2-20
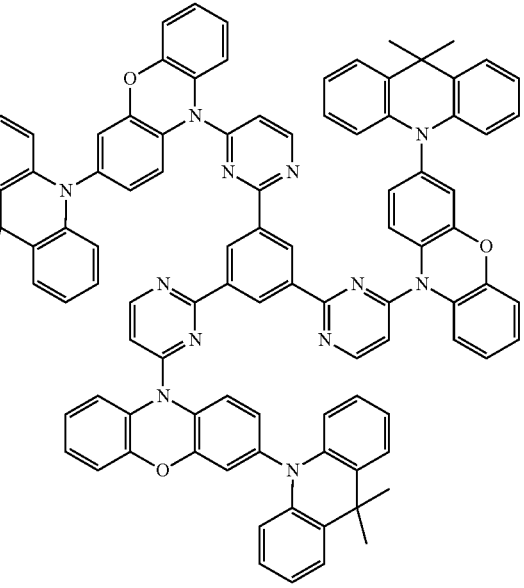

Compound 2-21
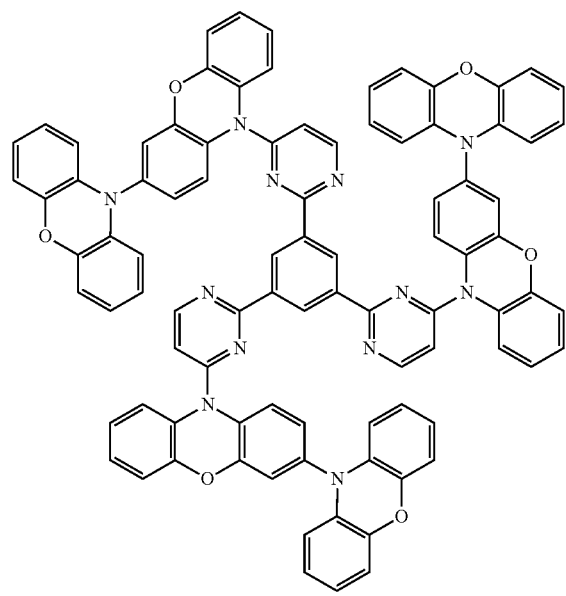
Compound 2-22
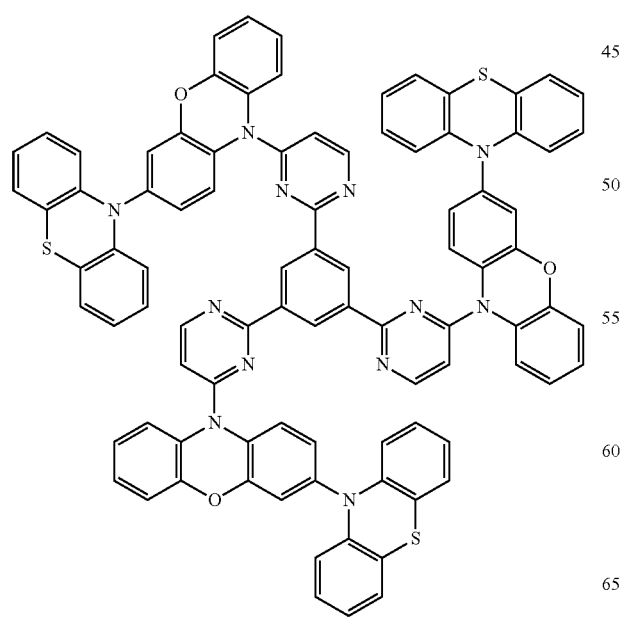
Compound 2-23
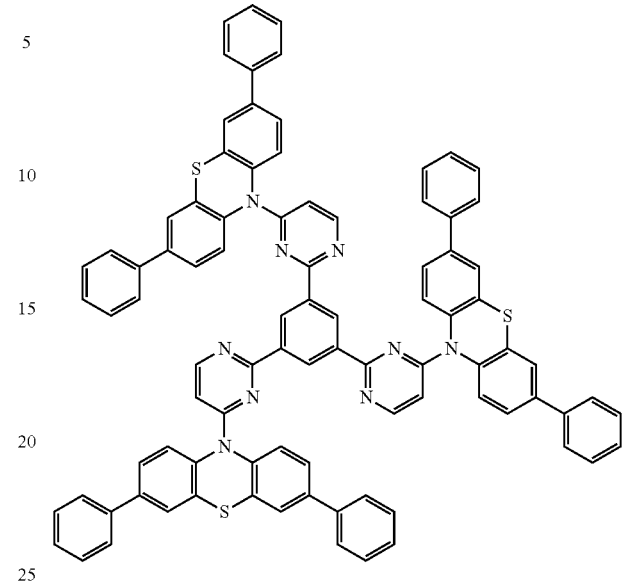
Compound 2-24
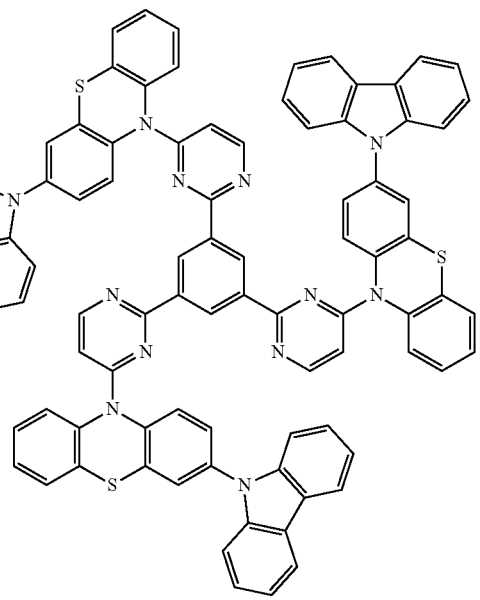

-continued

Compound 2-25

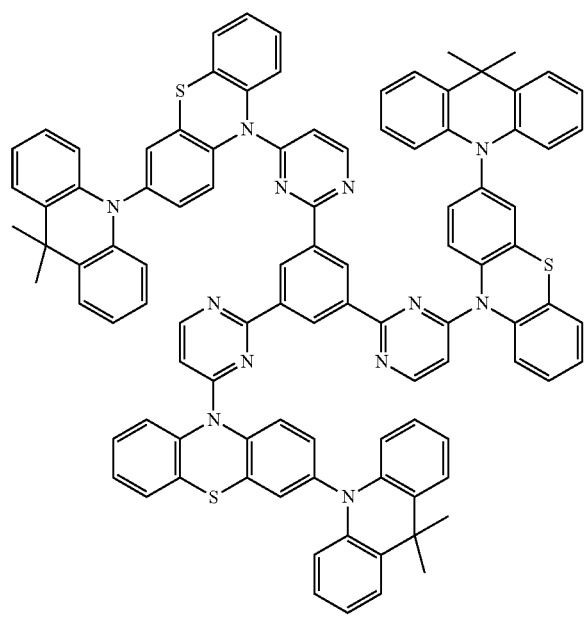

In still another exemplary embodiment, the fused heteroaromatic moiety defined in Chemical Formula 3 may include a carbazole moiety. As an example, the fused heteroaromatic moiety in Chemical Formula 3 including the carbazole moiety may have the following structure of Chemical Formula 10:

Chemical Formula 10

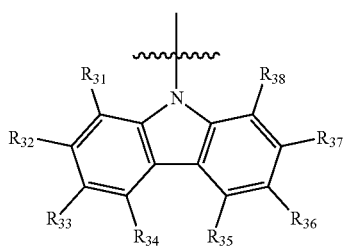

In Chemical Formula 10, each of $R_{31}$ to $R_{38}$ is independently hydrogen, silyl group, $C_1$-$C_{20}$ alkyl group, $C_1$-$C_{20}$ alkoxy group, $C_1$-$C_{20}$ alkylamino group, $C_5$-$C_{30}$ aryl group, $C_4$-$C_{30}$ heteroaryl group, $C_5$-$C_{30}$ aryloxyl group, $C_4$-$C_{30}$ heteroaryloxyl group, $C_5$-$C_{30}$ arylamino group or $C_4$-$C_{30}$ heteroaryl amino group, or two adjacent groups among $R_{31}$ to $R_{38}$ form $C_4$-$C_{30}$ fused aromatic or heteroaromatic ring unsubstituted or substituted with $C_4$-$C_{30}$ aromatic or heteroaromatic group.

Each of the aryl or heteroaryl group of $R_{31}$ to $R_{38}$ in Chemical Formula 10 may be the same as each of the aryl or heteroaryl group of $R_4$ to $R_6$ in Chemical Formula 2, as described above. As an example, each of $R_{31}$ to $R_{38}$ may comprise independently hydrogen (including protium, deuterium and tritium); linear or branched $C_1$-$C_{10}$ alkyl (e.g., methyl, ethyl, propyl, iso-propyl, butyl and/or iso-butyl); $C_5$-$C_{30}$ aryl (e.g., phenyl, biphenyl and/or naphthyl) unsubstituted or substituted with linear or branched $C_1$-$C_{10}$ alkyl group, $C_5$-$C_{30}$ aryl group and/or $C_4$-$C_{30}$ heteroaryl group; and $C_4$-$C_{30}$ heteroaryl (e.g., carbazolyl, acridinyl, phenazinly, phenoxazinyl and/or phenothiazinyl) unsubstituted or substituted with linear or branched $C_1$-$C_{10}$ alkyl group, $C_5$-$C_{30}$ aryl group and/or $C_4$-$C_{30}$ heteroaryl group.

In an alternative embodiment, the fused aromatic or heteroaromatic ring formed by two adjacent groups among $R_{31}$ to $R_{38}$ in Chemical Formula 10 may be the same as the fussed aromatic or heteroaromatic ring formed by the two adjacent groups among $R_{11}$ to $R_{18}$ in Chemical Formula 6. Particularly, the organic compound including the carbazole moiety of Chemical Formula 10 may include any one having the following structure of Chemical Formula 11:

Chemical Formula 11

Compound 3-1

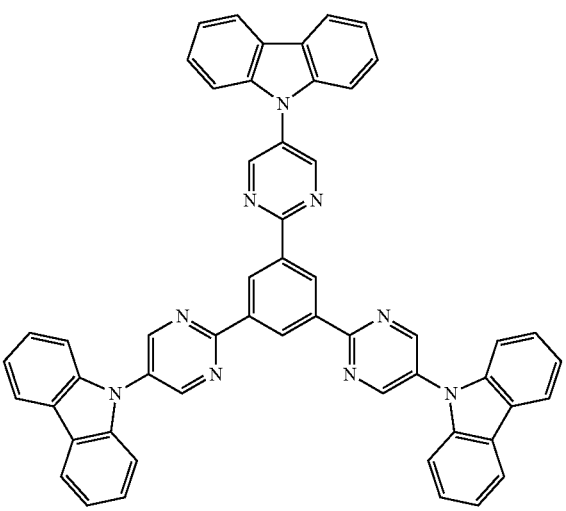

Compound 3-2

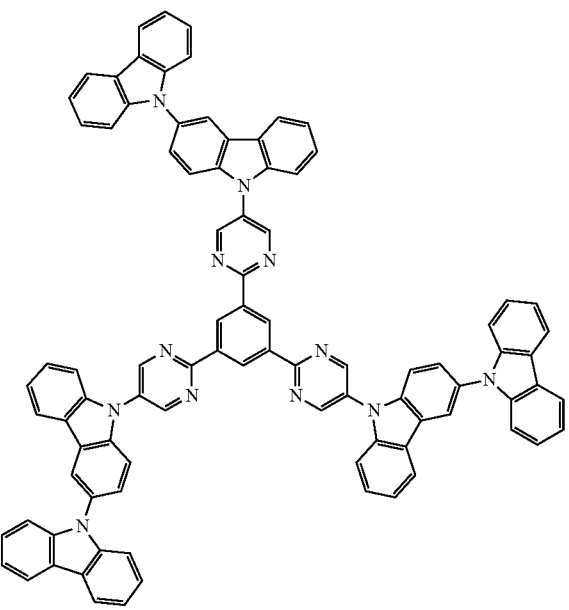

Compound 3-3
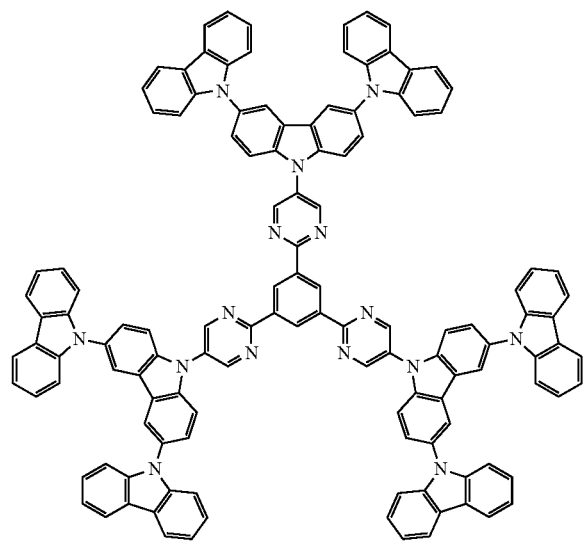
Compound 3-4
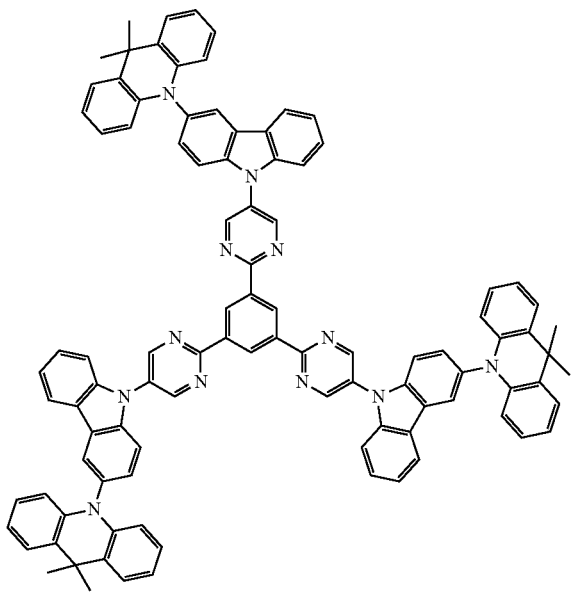
Compound 3-5
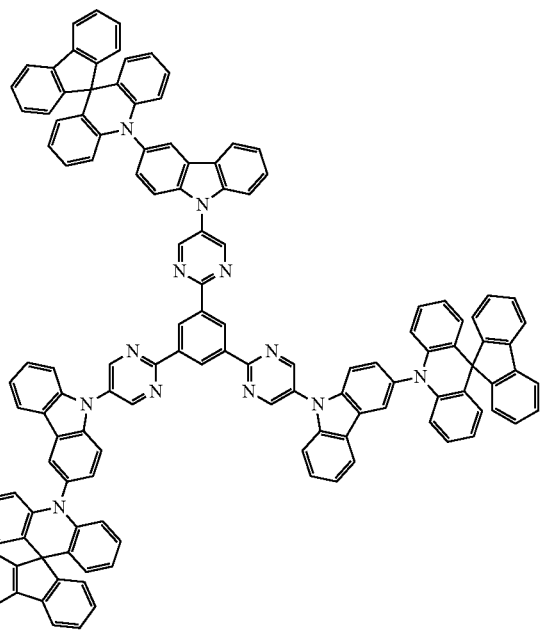
Compound 3-6
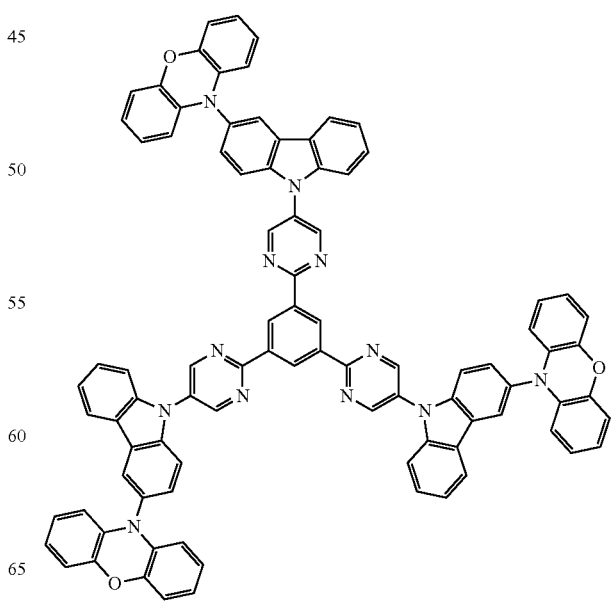

Compound 3-7
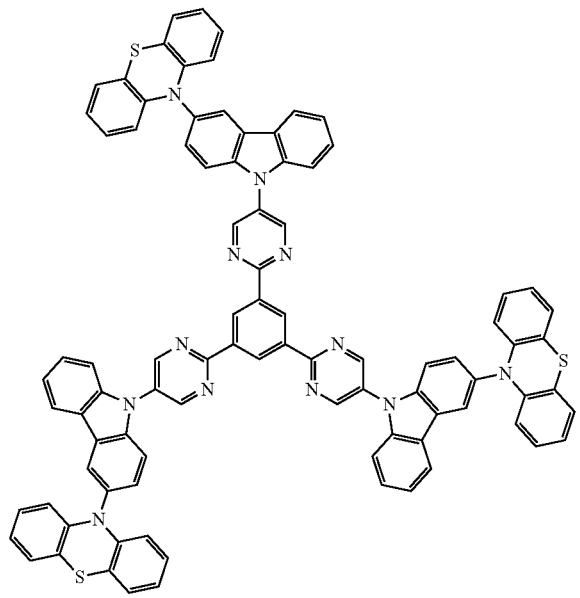
Compound 3-8
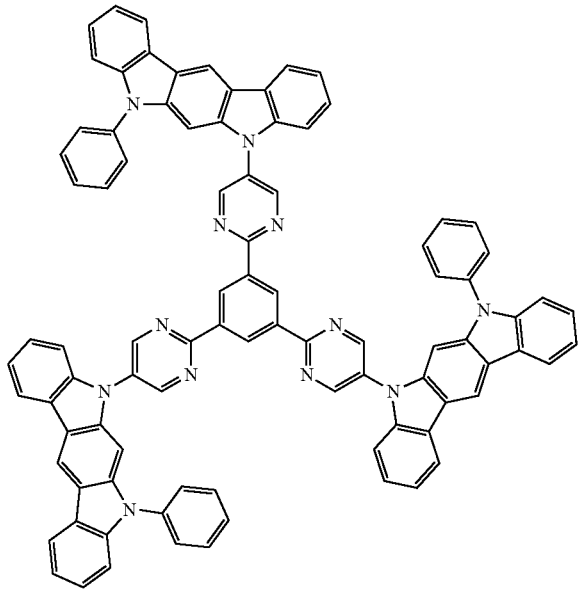
Compound 3-9
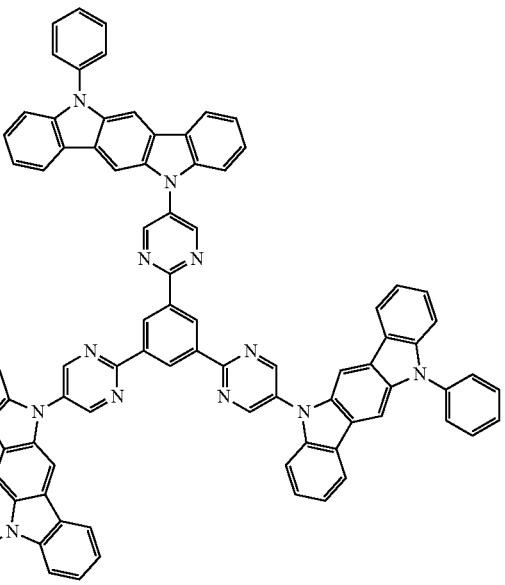
Compound 3-10
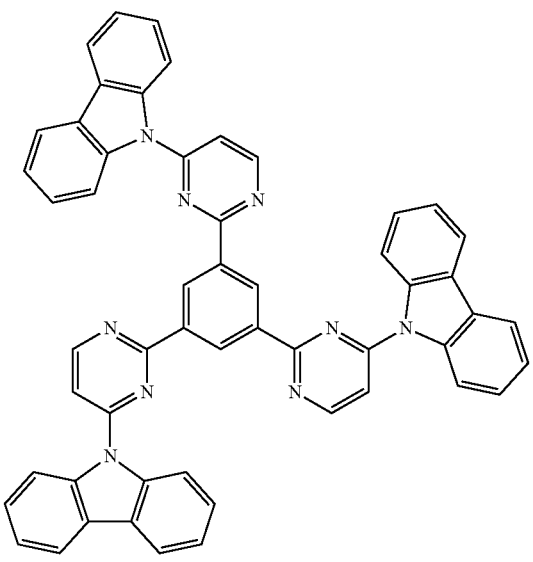

Compound 3-11
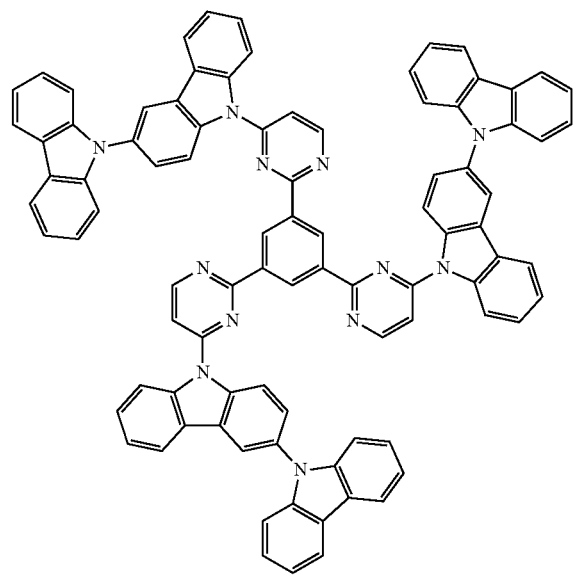
Compound 3-12
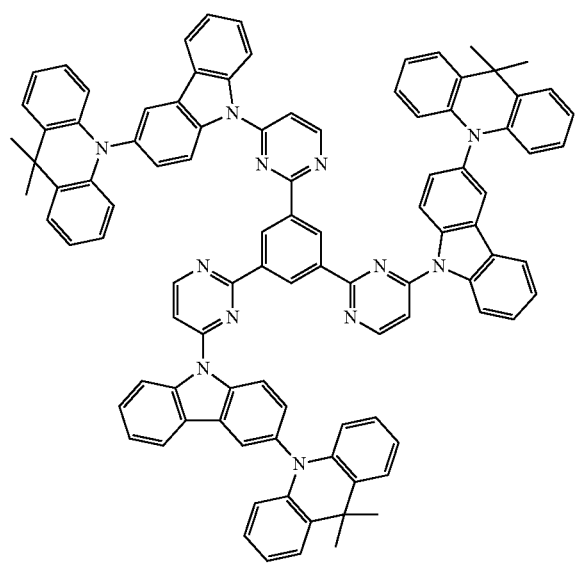
Compound 3-13
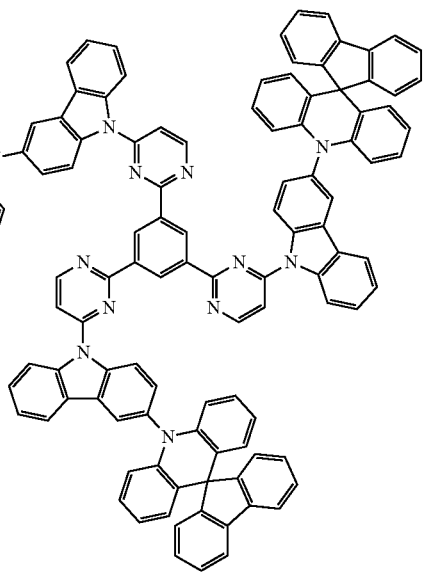
Compound 3-14
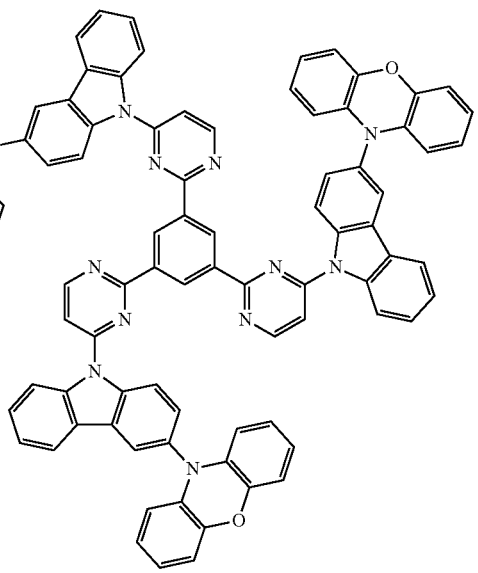

Compound 3-15
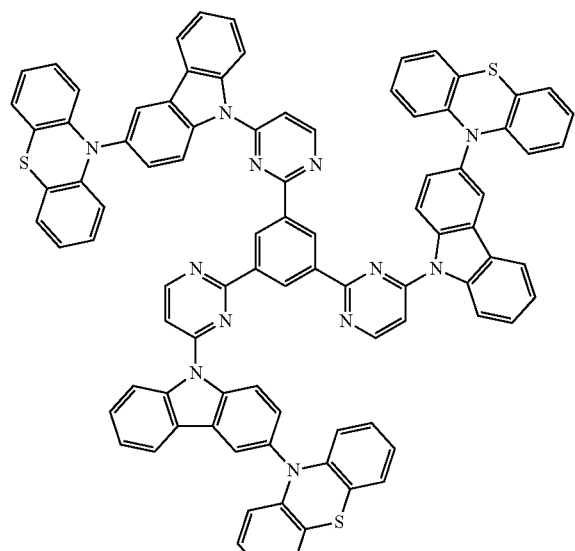
Compound 3-16
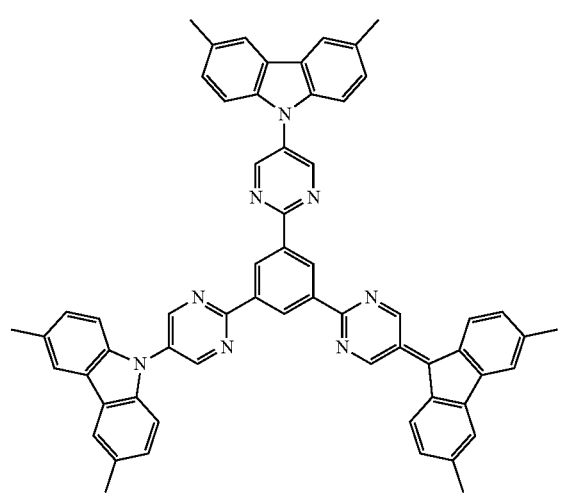
Compound 3-17
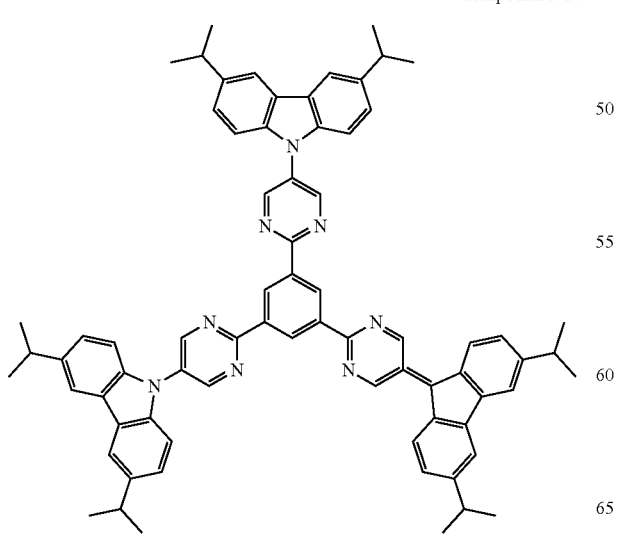
Compound 3-18
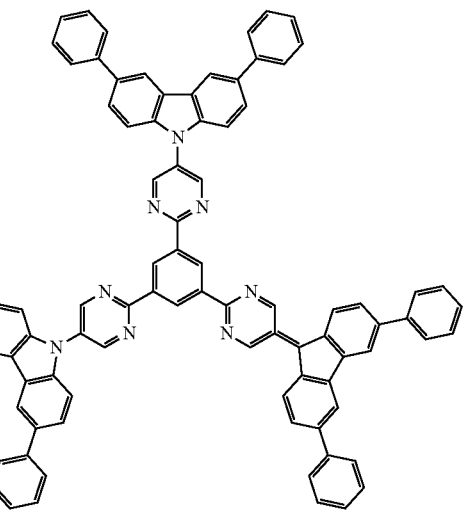
Compound 3-19
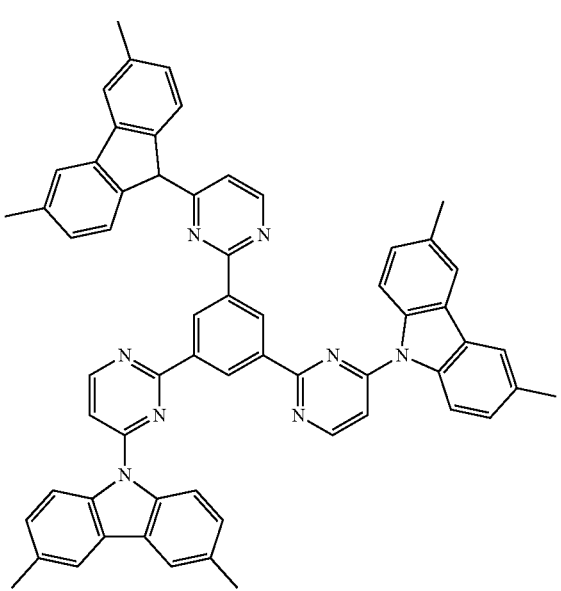

-continued

Compound 3-20

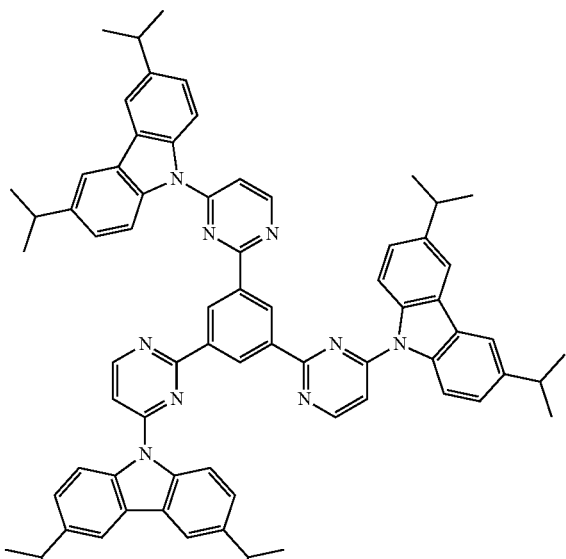

Compound 3-21

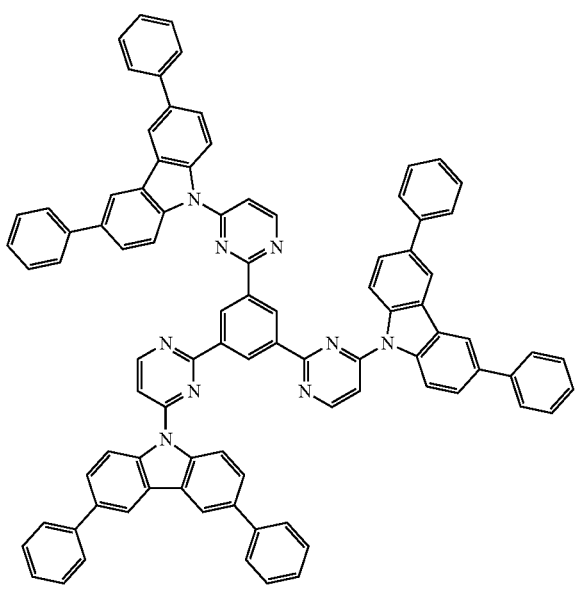

[Organic Light-Emitting Diode and Device]

The organic compound represented by the Chemical Formulae 1 to 11 has delayed fluorescence property since it shares both the electron donor and the electron acceptor within one molecule. The organic compound may be applied to an emitting material layer of an organic light-emitting diode (OLED) so as to enhance luminous efficiencies and lower driving voltage of the OLED. The organic light-emitting diode of the present disclosure may be applied to an organic light-emitting device such as an organic light-emitting display device and an organic light-emitting illumination device. An organic light-emitting display device having the organic light-emitting diode of the present disclosure will be explained. FIG. 1 is a schematic cross-sectional view illustrating an organic light-emitting display device of the present disclosure.

As illustrated in FIG. 1, the organic light-emitting display device 100 comprises a substrate 102, a thin-film transistor Tr on the substrate 102, and an organic light-emitting diode 200 connected to the thin film transistor Tr. The thin film transistor comprises a semiconductor layer 110, a gate electrode 130, a source electrode 152 and a drain electrode 154.

The substrate 102 may include, but is not limited to, glass, thin flexible material and/or polymer plastics. For example, the flexible material may be selected from the group, but is not limited to, polyimide (PI), polyethersulfone (PES), polyethylenenaphthalate (PEN), polyethylene terephthalate (PET), polycarbonate (PC) and combination thereof. The thin film transistor Tr and the substrate 102, over which the organic light-emitting diode 200 is arranged, form an array substrate.

A buffer layer 104 may be disposed over the substrate 102, and the thin film transistor Tr is disposed over the buffer layer 104. The buffer layer 104 may be omitted.

A semiconductor layer 110 is disposed over the buffer layer 104. In one exemplary embodiment, the semiconductor layer 110 may include, but is not limited to, oxide semiconductor materials. In this case, a light-shied pattern (not shown) may be disposed under the semiconductor layer 110, and the light-shield pattern (not shown) can prevent light from being incident toward the semiconductor layer 110, and thereby, preventing the semiconductor layer 110 from being deteriorated by the light. Alternatively, the semiconductor layer 110 may comprise polycrystalline silicon. In this case, opposite edges of the semiconductor layer 110 may be doped with impurities.

A gate insulating layer 120 formed of an insulating material is disposed on the semiconductor layer 110. The gate insulating layer 120 may include, but is not limited to, an inorganic insulating material such as silicon oxide ($SiO_x$) or silicon nitride ($SiN_x$).

A gate electrode 130 made of a conductive material such as a metal is disposed over the gate insulating layer 120 so as to correspond to a center of the semiconductor layer 110. While the gate insulating layer 120 is disposed over a whole area of the substrate 102 in FIG. 1, the gate insulating layer 120 may be patterned identically as the gate electrode 130.

An interlayer insulating layer 140 formed of an insulating material is disposed on the gate electrode 130 with covering over an entire surface of the substrate 102. The interlayer insulating layer 140 may include an inorganic insulating material such as silicon oxide ($SiO_x$) or silicon nitride ($SiN_x$), or an organic insulating material such as benzocyclobutene or photo-acryl.

The interlayer insulating layer 140 has first and second semiconductor layer contact holes 142 and 144 that expose both sides of the semiconductor layer 110. The first and second semiconductor layer contact holes 142 and 144 are disposed over opposite sides of the gate electrode 130 with spacing apart from the gate electrode 130. The first and second semiconductor layer contact holes 142 and 144 are formed within the gate insulating layer 120 in FIG. 1. Alternatively, the first and second semiconductor layer contact holes 142 and 144 are formed only within the interlayer insulating layer 140 when the gate insulating layer 120 is patterned identically as the gate electrode 130.

A source electrode 152 and a drain electrode 154, which are formed of a conductive material such as a metal, are disposed on the interlayer insulating layer 140. The source electrode 152 and the drain electrode 154 are spaced apart from each other with respect to the gate electrode 130, and contact both sides of the semiconductor layer 110 through the first and second semiconductor layer contact holes 142 and 144, respectively.

The semiconductor layer 110, the gate electrode 130, the source electrode 152 and the drain electrode 154 constitute the thin film transistor Tr, which acts as a driving element. The thin film transistor Tr in FIG. 1 has a coplanar structure in which the gate electrode 130, the source electrode 152 and the drain electrode 154 are disposed over the semiconductor layer 110. Alternatively, the thin film transistor Tr may have an inverted staggered structure in which a gate electrode is disposed under a semiconductor layer and a source and drain electrodes are disposed over the semiconductor layer. In this case, the semiconductor layer may comprise amorphous silicon.

Although not shown in FIG. 1, a gate line and a data line, which cross each other to define a pixel region, and a switching element, which is connected to the gate line and the data line, is may be further formed in the pixel region. The switching element is connected to the thin film transistor Tr, which is a driving element. In addition, a power line is spaced apart in parallel from the gate line or the data line, and the thin film transistor Tr may further include a storage capacitor configured to constantly keep a voltage of the gate electrode for one frame.

In addition, the organic light-emitting display device 100 may include a color filter (not shown) for absorbing a part of light emitted from the organic light-emitting diode 200. For example, the color filter (not shown) may absorb a light of specific wavelength such as red (R), green (G) or blue (B). In this case, the organic light-emitting display device 100 can implement full-color through the color filter (not shown).

For example, when the organic light-emitting display device 100 is a bottom-emission type, the color filter (not shown) may be disposed on the interlayer insulating layer 140 with corresponding to the organic light-emitting diode 200. Alternatively, when the organic light-emitting display device 100 is a top-emission type, the color filter (not shown) may be disposed over the organic light-emitting diode 200, that is, a second electrode 220.

A passivation layer 160 is disposed on the source and drain electrodes 152 and 154 over the whole substrate 102. The passivation layer 160 has a flat top surface and a drain contact hole 162 that exposes the drain electrode 154 of the thin film transistor Tr. While the drain contact hole 162 is disposed on the second semiconductor layer contact hole 144, it may be spaced apart from the second semiconductor layer contact hole 144.

The organic light-emitting diode 200 includes a first electrode 210 that is disposed on the passivation layer 160 and connected to the drain electrode 154 of the thin film transistor Tr. The organic light-emitting diode 200 further includes an emission layer 230 and a second electrode 220 each of which is disposed sequentially on the first electrode 210.

The first electrode 210 is disposed in each pixel region. The first electrode 210 may be an anode and include a conductive material having relatively high work function value. For example, the first electrode 210 may include, but is not limited to, a transparent conductive material such as indium tin oxide (ITO), indium zinc oxide (IZO), indium tin zinc oxide (ITZO), SnO, ZnO, indium cerium oxide (ICO), aluminum doped zinc oxide (AZO), and the like.

In one exemplary embodiment, when the organic light-emitting display device 100 is a top-emission type, a reflective electrode or a reflective layer (not shown) may be disposed under the first electrode 210. For example, the reflective electrode or the reflective layer (not shown) may include, but is not limited to, aluminum-palladium-copper (APC) alloy.

In addition, a bank layer 170 is disposed on the passivation layer 160 in order to cover edges of the first electrode 210. The bank layer 170 exposes a center of the first electrode 210.

An emission layer 230 is disposed on the first electrode 210. In one exemplary embodiment, the emission layer 230 may have a mono-layered structure of an emitting material layer. Alternatively, the emission layer 230 may have a multiple-layered structure of a hole injection layer, a hole transport layer, an electron blocking layer, an emitting material layer, a hole blocking layer, an electron transport layer and/or an electron injection layer (See, FIGS. 2, 5, 7 and 9). The emission layer 230 includes the organic compound represented by any one of Chemical Formulae 1 to 11. For example, the organic compound represented by any one of Chemical Formulae 1 to 11 may be used as a dopant of the emission layer 230, and the emission layer 230 may include a host and, optionally other dopants.

The second electrode 220 is disposed over the substrate 102 above which the emission layer 230 is disposed. The second electrode 220 may be disposed over a whole display area, and may include a conductive material with a relatively low work function value compared to the first electrode 210, and may be a cathode. For example, the second electrode 220 may include, but is not limited to, aluminum (Al), magnesium (Mg), calcium (Ca), silver (Ag), alloy thereof or combination thereof such as aluminum-magnesium alloy (Al—Mg).

In addition, an encapsulation film 180 may be disposed over the second electrode 220 in order to prevent outer moisture from penetrating into the organic light-emitting diode 200. The encapsulation film may have, but is not limited to, a laminated structure of a first inorganic insulating film 182, an organic insulating film 184 and a second inorganic insulating film 186.

The emission layer 230 of the organic light-emitting diode 200 may include the organic compound represented by any one of Chemical Formulae 1 to 11 as a dopant, as described above. Such organic compound shows delayed fluorescence properties because it includes an electron donor as well as an electron acceptor within its molecular structure. It is possible to enhance luminous efficiency of the organic light-emitting diode 200 and to implement long luminous life spans as well as low driving voltage, i.e. decreased consumption powers in the diode 200, by applying the organic compound into the emission layer 230.

Figure 2:
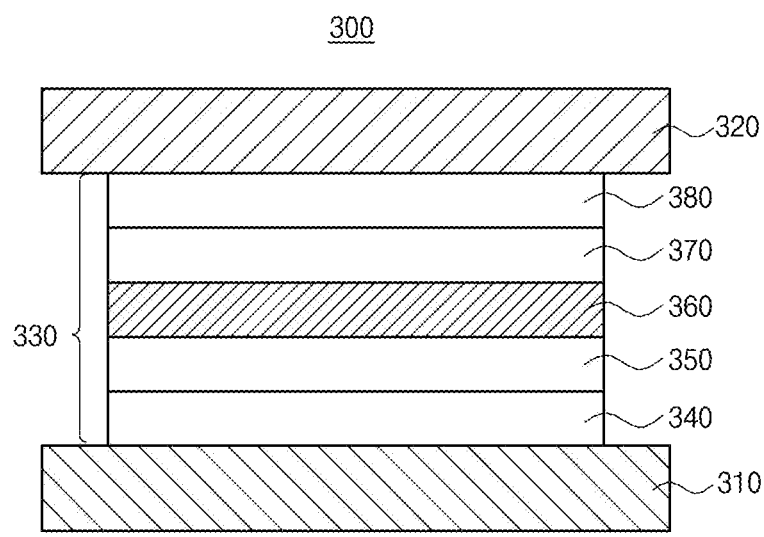
FIG. 2 is a schematic cross-sectional view illustrating an organic light-emitting diode in accordance with an exemplary embodiment of the present disclosure.

FIG. 2 is a schematic cross-sectional view illustrating an organic light-emitting diode having an organic compound as a fluorescent dopant in a single EML in accordance with an exemplary embodiment of the present disclosure.

As illustrated in FIG. 2, the organic light-emitting diode (OLED) 300 in accordance with an exemplary embodiment of the present disclosure includes first and second electrodes 310 and 320 facing each other, an emission layer 330 disposed between the first and second electrodes 310 and 320. In one exemplary embodiment, the emission layer 330 include a hole injection layer (HIL) 340, a hole transport layer (HTL) 350, an emitting material layer (EML) 360, an electron transport layer (ETL) 370 and an electron injection layer (EIL) 380 each of which is laminated sequentially from the first electrode 310.

The first electrode 310 may be an anode that provides a hole into the EML 360. As described above, the first electrode 310 may include a conductive material having a relatively high work function value, for example, a transparent conductive oxide (TCO). In an exemplary embodiment, the first electrode 310 may include, but is not limited to, ITO, IZO, ITZO, SnO, ZnO, ICO, AZO, and the like.

The second electrode 320 may be a cathode that provides an electron into the EML 360. As described above, the second electrode 320 may include a conductive material having a relatively low work function values, i.e., a highly reflective material such as Al, Mg, Ca, Ag, alloy thereof, combination thereof, and the like.

The HIL 340 is disposed between the first electrode 310 and the HTL 350 and improves an interface property between the inorganic first electrode 310 and the organic HTL 350. In one exemplary embodiment, the HIL 340 may include, but is not limited to, 4,4'4"-Tris(3-methylphenylamino)triphenylamine (MTDATA), 4,4',4"-Tris(N,N-diphenyl-amino)triphenylamine (NATA), 4,4',4"-Tris(N-(naphthalene-1-yl)-N-phenyl-amino)triphenylamine (1T-NATA), 4,4',4"-Tris(N-(naphthalene-2-yl)-N-phenyl-amino) triphenylamine (2T-NATA), Copper phthalocyanine (CuPc), Tris(4-carbazoyl-9-yl-phenyl)amine (TCTA), N,N'-Diphenyl-N,N'-bis(1-naphthyl)-1,1'-biphenyl-4,4"-diamine (NPB; NPD), 1,4,5,8,9,11-Hexaazatriphenylenehexacarbonitrile (Dipyrazino[2,3-f:2'3'-h]quinoxaline-2,3,6,7,10,11-hexacarbonitrile; HAT-CN), 1,3,5-tris[4-(diphenylamino)phenyl] benzene (TDAPB), poly(3,4-ethylenedioxythiphene)polystyrene sulfonate (PEDOT/PSS) and/or N-(biphenyl-4-yl)-9,9-dimethyl-N-(4-(9-phenyl-9H-carbazol-3-yl)phenyl)-9H-fluoren-2-amine. The HIL 340 may be omitted in compliance with a structure of the OLED 300.

The HTL 350 is disposed adjacently to the EML 360 between the first electrode 310 and the EML 360. In one exemplary embodiment, the HTL 350 may include, but is not limited to, N,N'-Diphenyl-N,N'-bis(3-methylphenyl)-1, 1'-biphenyl-4,4'-diamine (TPD), NPB, 4,4'-bis(N-carbazolyl)-1,1'-biphenyl (CBP), Poly[N,N'-bis(4-butylphenyl)-N,N'-bis(phenyl)-benzidine] (Poly-TPD), Poly[(9,9-dioctylfluorenyl-2,7-diyl)-co-(4,4'-(N-(4-sec-butylphenyl) diphenylamine))] (TFB), Di-[4-(N,N-di-p-tolyl-amino)-phenyl]cyclohexane (TAPC), N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

In one exemplary embodiment, each of the HIL 340 and the HTL 350 may be laminated with a thickness of, but is not limited to, about 5 nm to about 200 nm, preferably about 5 nm to about 100 nm.

The EML 360 may include a host and a dopant in which substantial luminescence is performed. In this exemplary embodiment, the EML 360 may include a host (a first host) and a dopant (first dopant). The organic compound represented by any one of Chemical Formulae 1 to 11 having delayed fluorescence properties may be used as the dopant (first dopant or T dopant) in the EML 360. As an example, the EML 360 may emit green (G) light.

The ETL 370 and the EIL 380 are laminated sequentially between the EML 360 and the second electrode 320. The ETL 370 includes a material having high electron mobility so as to provide electrons stably with the EML 360 by fast electron transportation.

In one exemplary embodiment, the ETL 370 may include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like.

Particularly, the ETL 370 may include, but is not limited to, tris-(8-hydroxyquinoline aluminum ($Alq_3$), 2-biphenyl-4-yl-5-(4-t-butylphenyl)-1,3,4-oxadiazole (PBD), spiro-PBD, lithium quinolate (Liq), 1,3,5-Tris(N-phenylbenzimidazol-2-yl)benzene (TPBi), Bis(2-methyl-8-quinolinolato-N1,O8)-(1,1'-biphenyl-4-olato)aluminum (BAlq), 4,7-diphenyl-1,10-phenanthroline (Bphen), 2,9-Bis (naphthalene-2-yl)4,7-diphenyl-1,10-phenanthroline (NBphen), 2,9-Dimethyl-4,7-diphenyl-1,10-phenathroline (BCP), 3-(4-Biphenyl)-4-phenyl-5-tert-butylphenyl-1,2,4-triazole (TAZ), 4-(Naphthalen-1-yl)-3,5-diphenyl-4H-1,2,4-triazole (NTAZ), 1,3,5-Tri(p-pyrid-3-yl-phenyl)benzene (TpPyPB), 2,4,6-Tris(3'-(pyridin-3-yl)biphenyl-3-yl) 1,3,5-triazine (TmPPPyTz), Poly[9,9-bis(3'-(N,N-dimethyl)-N-ethylammonium)-propyl)-2,7-fluorene]-alt-2,7-(9,9-dioctylfluorene)](PFNBr) and/or tris(phenylquinoxaline) (TPQ).

The EIL 380 is disposed between the second electrode 320 and the ETL 370, and can improve physical properties of the second electrode 320 and therefore, can enhance the life span of the OLED 300. In one exemplary embodiment, the EIL 380 may include, but is not limited to, an alkali halide such as LiF, CsF, NaF, $BaF_2$ and the like, and/or an organic metal compound such as lithium benzoate, sodium stearate, and the like.

As an example, each of the ETL 370 and the EIL 380 may be laminated with a thickness of, but is not limited to, about 10 nm to about 200 nm, preferably about 10 nm to 100 nm.

The organic light-emitting diode 300 may further comprise at least one exciton blocking layer (not shown). As an example, the OLED 300 of the exemplary embodiment may include an electron blocking layer (EBL, not shown) between the HTL 350 and the EML 360 and/or a hole blocking layer (HBL, not shown) between the EML 360 and the ETL 370.

As described above, the EML 360 in the OLED 300 includes the host and the organic compound represented by any one of Chemical Formulae 1 to 11 and having delayed fluorescence properties as the first dopant. The first dopant having delayed fluorescence properties in the EML 360 allows the OLED 300 to enhance its luminous efficiencies and to lower its driving voltage.

An Organic Light Emitting Diode (OLED) emits light as holes injected from the anode and electrons injected from the cathode are combined to form excitons in an EML and then unstable excited state excitons return to a stable ground state. The external quantum efficiency (EQE; $\eta_{ext}$) of the luminous material applied into the EML can be calculated by the following Equation (1):

$$\eta_{ext} = \eta_{S/T} \times \Gamma \times \Phi \times \eta_{out\text{-}coupling} \qquad (1)$$

In Equation (1), "$\eta_{S/T}$" is exciton generation efficiency (singlet/triplet ratio); "Γ" is a charge balance factor; "Φ" is radiative quantum efficiency; "$\eta_{out\text{-}coupling}$" is out-coupling efficiency.

"$\eta_{S/T}$" is a transformation ratio from exciton to light and has maximum value of 0.25 in case of fluorescent materials. Theoretically, when electrons meet holes to form exciton, a singlet exciton of a paired spin and a triplet exciton of an unpaired spin are produced by a ratio of 1:3 by spin arrangements. Only the singlet exciton among the excitons can only be involved in emission process in case of the fluorescent materials.

Charge balance factor "Γ" is a balance between holes and electrons both of which form excitons and generally has a value of "1" assuming 1:1 matching of 100%. "Φ" is a value related with luminous efficiency of actual luminous materials and depends upon photoluminescence of dopant in a host-dopant system.

"$\eta_{out\text{-}coupling}$" is a ratio of light extracted outwardly among the emitted light in a luminous materials. When isotropic luminous material is thermally deposited to form a thin film, each of luminous molecules does not have specific orientation, but exists with random states. The out-coupling efficiency in such random orientation is generally assumed "0.2". Accordingly, when combining 4 parameters of Equation (1) above, the OLED may exhibit 5% luminous efficiency by maximum in case of using the prior art fluorescent material.

In contrast, phosphorescent materials use different luminous mechanism of converting both singlet excitons and triplet exciton into light. The phosphorescent materials convert singlet excitons into triplet excitons through intersystem crossing (ISC). Therefore, it is possible to enhance luminous efficiency in case of applying the phosphorescent materials that use both the singlet excitons and the triplet excitons during the luminous process compared to the fluorescent materials.

In case of using metal complexes having a heavy metal such as Ir, Pt, and the like as the phosphorescent materials, it is possible to convert triplet state to singlet state through strong spin-orbital bonds by the heavy metal. However, the prior art phosphorescent materials do not have enough color purity for the display device and exhibit very short luminous life span, and therefore, they have not been used in commercial display devices.

In order to overcome the problems caused by conventional fluorescent or phosphorescent material, a delayed fluorescent material has been developed. Typical delayed fluorescent material uses thermally activated delayed fluorescence. The delayed fluorescent material enables intramolecular charge transfer and uses both the singlet energy and triplet energy during luminescent process. As such, the delayed fluorescent material has enhanced luminous efficiency owing to utilizing the triplet energy as well as the singlet energy as the phosphorescent material.

The delayed fluorescence may be divided into thermally activated delayed fluorescence (TATF) and field activated delayed fluorescence (FADF). The delayed florescent material is activated by heat or electrical field and implement excellent luminescence above the maximum luminous efficiency exhibited by the conventional fluorescent materials.

Luminous mechanism of delayed fluorescent material will be explained with referring to FIG. 3, which is a schematic diagram illustrating luminous mechanism of the delayed fluorescent material in an EML in accordance with an exemplary embodiment of the present disclosure. The delayed fluorescent material typically has both an electron donor moiety and an electron acceptor moiety so that it can be converted into an intramolecular charge transfer (ICT) state. In case of using the delayed fluorescent material that can be converted into ICT state as the dopant, both excitons of the singlet energy level $S_1$ and excitons of the triplet energy level $T_1$ are moved to Intermediate energy level state, i.e. ICT state, and then the excitons in ICT state is transferred to a ground state ($S_0$; $S_1 \rightarrow ICT \leftarrow T_1$). Since both the excitons of singlet energy level $S_1$ and the excitons of triplet energy level $T_1$ in the delayed fluorescent material is involved in the luminescence process, the delayed fluorescent material can improve internal quantum efficiency and luminous efficiency of the diode.

Since the Highest Occupied Molecular Orbital (HOMO) state and the Lowest Unoccupied Molecular orbital (LUMO) state are widely distributed over the whole molecule in the conventional fluorescent materials, it is not possible to inter-convert between the singlet energy level and the triplet energy level in the conventional fluorescent materials (selection rule). In contrast, since the delayed fluorescent material, which can be converted to ICT state, has little orbital overlaps between HOMO and LUMO, there is little interaction between the HOMO state molecular orbital and the LUMO state molecular orbital within the delayed fluorescent material. As a result, changing spin states of electrons does not have an influence on other electrons, and a new charge transfer band (CT band) that does not follow the selection rule is formed in the delayed fluorescent material.

In other words, since the delayed fluorescent material has the electron acceptor moiety spacing apart from the electron donor moiety within the molecule, it exists as a polarized state having a large dipole moment within the molecule. As the interaction between HOMO molecular orbital and LUMO molecular orbital becomes little with the polarized state of the dipole moment, both the triplet energy level excitons and the singlet energy level excitons can be converted to ICT state. Accordingly, both the excitons of triplet energy level $T_1$ as well as the excitons of singlet energy level $S_1$ can be involved in the emission process.

In case of driving the OLED including the delayed fluorescent material, 25% excitons of singlet energy level $S_1$ and 75% excitons of triplet energy level $T_1$ are converted to ICT state by heat or electrical field, and then the converted excitons transfer to the ground state $S_0$ with luminescence. Therefore, the delayed fluorescent material may have 100% internal quantum efficiency in theory.

The delayed fluorescent material must has an energy level bandgap $\Delta E_{ST}^{TD}$ equal to or less than about 0.3 eV, for example, from about 0.05 to about 0.3 eV, between the singlet energy level $S_1$ and the triplet energy level $T_1$ so that exciton energy in both the singlet energy level and the triplet energy level can be transferred to the ICT state. The material having little energy level bandgap between the singlet energy level $S_1$ and the triplet energy level $T_1$ can exhibit common fluorescence with Inter system Crossing (ISC) in which the excitons of singlet energy level $S_1$ can be transferred to the excitons of triplet energy level $T_1$, as well as delayed fluorescence with Reverser Inter System Crossing (RISC) in which the excitons of triplet energy level $T_1$ can be transferred upwardly to the excitons of singlet energy level $S_1$ and then the exciton of singlet energy level $S_1$ transferred from the triplet energy level $T_1$ can be transferred to the ground state $S_0$.

Since the delayed fluorescent material can exhibit 100% internal quantum efficiency in theory, it can implement as high luminous efficiency as the prior art phosphorescent material including a heavy metal. The host for implementing the delayed fluorescence must induce the triplet excitons of the dopant to be involved in the luminescence process without quenching. Accordingly, the exciton energy levels between the host and the delayed fluorescent material should be adjusted.

Figure 4:
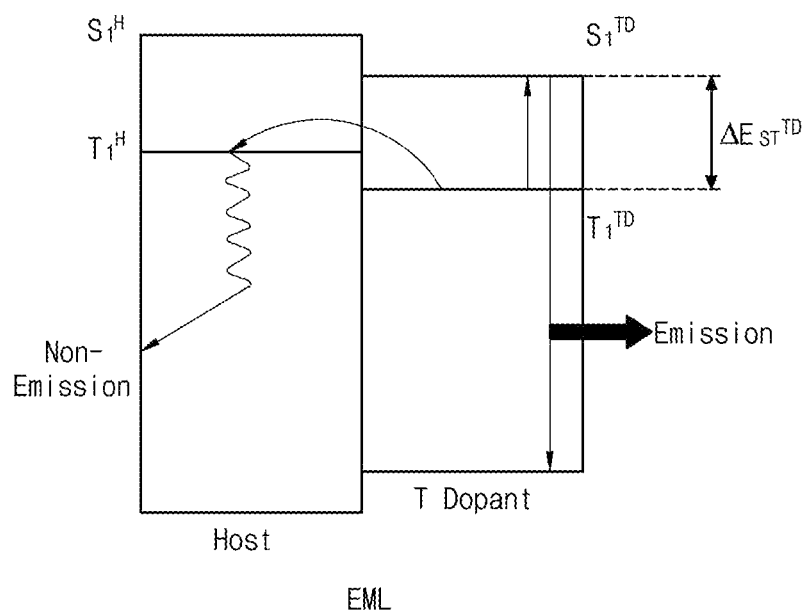
FIG. 4 is a schematic diagram illustrating the luminous mechanism by the energy level bandgap between a host and an organic compound as a delayed fluorescent dopant in an EML in accordance with an exemplary embodiment of the present disclosure.

FIG. 4 is a schematic diagram illustrating luminous mechanism by energy level bandgap between a host and the organic compound having delayed fluorescence properties in a single-layered EML in accordance with an exemplary embodiment of the present disclosure. As illustrated in FIG. 4, each of an excited state singlet energy level $S_1^H$ and an excited state triplet energy level $T_1^H$ of the host is respectively higher than each of an excited state singlet energy level $S_1^{TD}$ and an excited state triplet energy level $T_1^{TD}$ of the first dopant (T dopant), respectively, which is the organic compound represented any one of Chemical Formulae 1 to 11 and having the delayed fluorescence properties, in the EML 360. As an example, the excited stated triplet energy level $T_1^H$ of the host is higher than the excited state triplet energy level $T_1^{TD}$ of the first dopant by at least of about 0.2 eV.

When the excited state triplet energy level $T_1^H$ and the exited state singlet energy level $S_1^H$ of the host is not higher enough than the excited state triplet energy level $T_1^{TD}$ and the excited state singlet energy level $S_1^{TD}$ of the first dopant, the excitons of the triplet state $T_1^{TD}$ of the first dopant may be transferred to the excited state triplet energy level $T_1^H$ of the host. Accordingly, the excitons of the triplet state $T_1^{TD}$ of the first dopant cannot be involved in the luminescence process because the triplet excitons transferred to the host is quenched without luminescence. As an example, the first host may have, but is not limited to, the excited state singlet energy level $S_1^H$ equal to or more than about 2.8 eV and the excited state triplet energy level $T_1^H$ equal to or more than about 2.6 eV.

Figure 3:
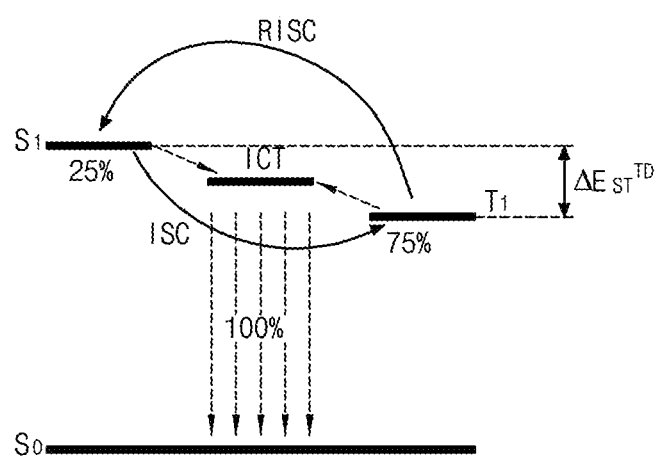
FIG. 3 is a schematic diagram illustrating the luminous mechanism of the delayed fluorescent material in EML in accordance with an exemplary embodiment of the present disclosure.

The first dopant, which may be the organic compound represented by any one of Chemical Formulae 1 to 11 and having the delayed fluorescence properties, may have the energy bandgap ($\Delta_{ES}^{TD}$) between the singlet energy level $S_1^{TD}$ and the triplet energy level $T_1^{TD}$ of at most 0.3 eV, for example between about 0.05 eV and about 0.3 eV (See, FIG. 3).

In addition, it is necessary to adjust properly Highest Occupied Molecular Orbital (HOMO) energy levels and Lowest Unoccupied Molecular Orbital (LUMO) energy levels of the host and the delayed fluorescent dopant. For example, it may be preferable that an energy level bandgap ($|HOMO^H-HOMO^{TD}|$) between a Highest Occupied Molecular Orbital energy level ($HOMO^H$) of the host and a Highest Occupied Molecular Orbital energy level ($HOMO^{TD}$) of the delayed fluorescent dopant, or an energy level bandgap ($|LUMO^H-LUMO^{TD}|$) between a Lowest Unoccupied Molecular Orbital energy level ($LUMO^H$) of the host and a Lowest Unoccupied Molecular Orbital energy level ($LUMO^{TD}$) of the first dopant may be equal to or less than about 0.5 eV, for example, between about 0.1 eV to about 0.5 eV. In this case, the charges can be moved efficiently from the host to the delayed fluorescent dopant and thereby enhancing an ultimate luminous efficiency.

In addition, the energy level bandgap ($Eg^H$) between the HOMO energy level ($HOMO^H$) and the LUMO energy level ($LUMO^H$) in the host may be larger than the energy level bandgap ($Eg^{TD}$) between the HOMO energy level ($HOMO^{TD}$) and the LUMO energy level ($LUMO^{TD}$) of the first dopant. As an example, the HOMO energy level ($HOMO^H$) of the host is deeper (lower) than the HOMO energy level ($HOMO^{TD}$) of the first dopant, and the LUMO energy level ($LUMO^H$) of the host is higher (shallower) than the LUMO energy level ($LUMO^{TD}$).

In one exemplary embodiment, the organic compound, which is represented by any one of Chemical Formulae 1 to 11 and can be used as the first dopant having the delayed fluorescence properties, may have a HOMO energy level ($HOMO^{TD}$) between about −4.5 eV and about −5.9 eV, preferably between about −5.0 eV and about −5.7 eV, a LUMO energy level ($LUMO^{TD}$) between about −2.0 eV and about −3.5 eV, preferably between about −2.2 eV and about −2.9 eV, and an energy bandgap ($Eg^{TD}$) between about 2.3 eV and about 3.0 eV, preferably between about 2.4 eV and about 2.8 eV. In contrast, the host may have a HOMO energy level ($HOMO^H$) between about −5.0 eV and about −6.5 eV, preferably between about −5.5 eV and about −6.2 eV, a LUMO energy level ($LUMO^H$) between about −1.5 eV and about −3.0 eV, preferably between about −1.5 eV and about −2.5 eV, and an energy bandgap ($Eg^H$) between about 3.0 eV and about 4.0 eV, preferably between about 3.0 eV and about 3.5 eV.

In one exemplary embodiment, the host in the EML 360 may include, but is not limited to, 9-(3-(9H-carbazol-9-yl)phenyl)-9H-carbazole-3-carbonitrile (mCP-CN), CBP, 3,3'-bis(N-carbazolyl)-1,1'-biphenyl (mCBP), 1,3-Bis(carbazol-9-yl)benzene (mCP), Oxybis(2,1-phenylene))bis(diphenylphosphine oxide (DPEPO), 2,8-Bis(diphenylphosphoryl)dibenzothiophene (PPT), 1,3,5-Tri[(3-pyridyl)-phen-3-yl]benzene (TmPyPB), 2,6-Di(9H-carbazol-9-yl)pyridine (PYD-2Cz), 2,8-di(9H-carbazol-9-yl)dibenzothiophene (DCzDBT), 3',5'-Di(carbazol-9-yl)-[1,1'-bipheyl]-3,5-dicarbonitrile (DCzTPA), 4'-(9H-carbazol-9-yl)biphenyl-3,5-dicarbonitrile (pCzB-2CN), 3'-(9H-carbazol-9-yl)biphenyl-3,5-dicarbonitrile (mCzB-2CN), Diphenyl-4-triphenylsilylphenyl-phosphine oxide (TPSO1), 9-(9-phenyl-9H-carbazol-6-yl)-9H-carbazole (CCP), 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole 9-(6-(9H-carbazol-9-yl)pyridin-3-yl)-9H-3,9'-bicarbazole and/or 4-(3-triphenylen-2-yl)phenyl)dibenzo[b,d]thiophene.

In case the EML 360 includes the host and the first dopant, the weight ratio of the host may be equal to or more than the weight ratio of the first dopant. As an example, the first dopant may comprise between about 1 to about 50% by weight, preferably between about 10 to about 40% by weight, more preferably between about 20 to about 40% by weight, in the EML 360.

In accordance with the first embodiment, the OLED 300 includes the EML 360 having only one dopant having delayed fluorescence properties. Unlike that embodiment, an EML may have multiple dopants each of which has different luminescence properties.

Figure 5:
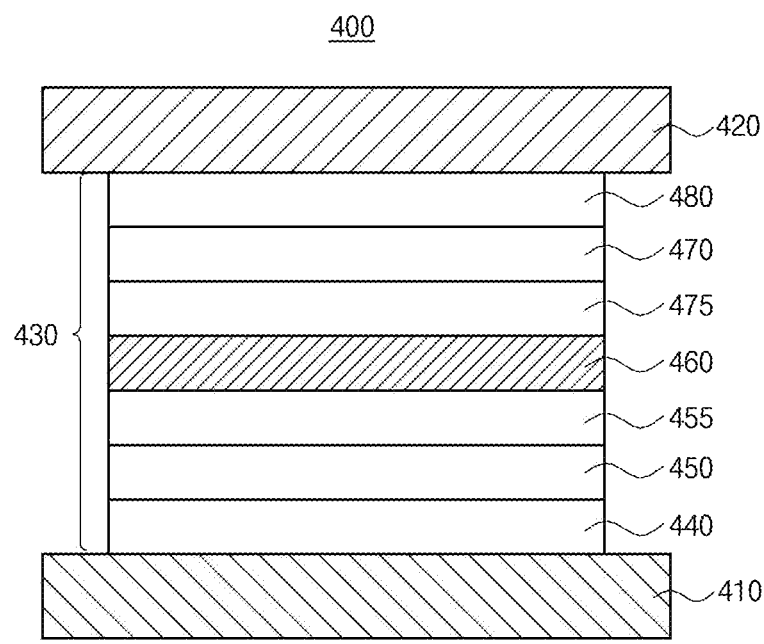
FIG. 5 is a schematic cross-sectional view illustrating an organic light-emitting diode in accordance with another exemplary embodiment of the present disclosure.
Figure 6:
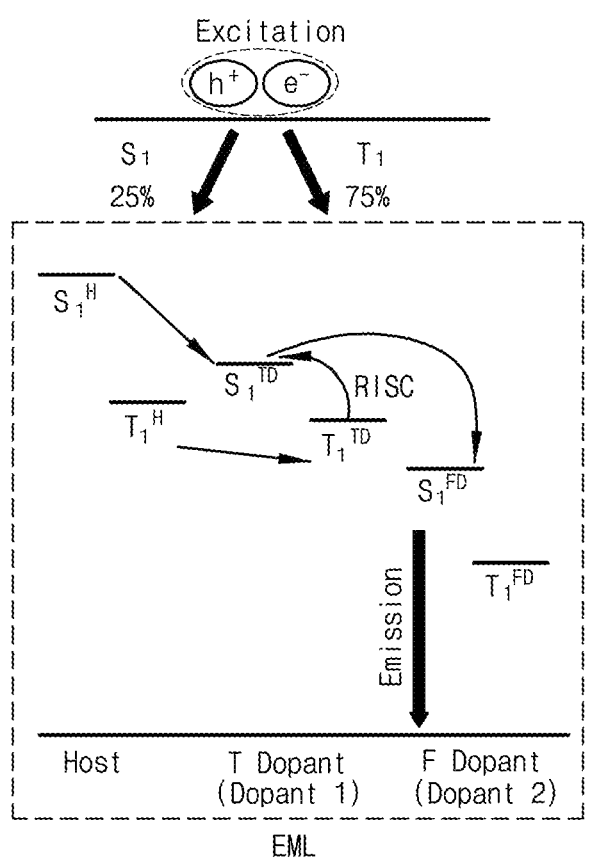
FIG. 6 is a schematic diagram illustrating the luminous mechanism by the energy level bandgap among a host, a delayed fluorescent dopant and a fluorescent material in an EML in accordance with another exemplary embodiment of the present disclosure.

FIG. 5 is a schematic cross-sectional view illustrating an organic light-emitting diode in accordance with another exemplary embodiment of the present disclosure and FIG. 6 is a schematic diagram illustrating luminous mechanism by energy level bandgap among a host, the organic compound having delayed fluorescence properties and a fluorescent material in a single-layered EML in accordance with another exemplary embodiment of the present disclosure.

As illustrated in FIG. 5, an organic light-emitting diode 400 in accordance with another exemplary embodiment includes first and second electrodes 410 and 420 facing each other and an emission layer 430 disposed between the first and second electrodes 410 and 420.

In an exemplary embodiment, the emission layer 430 includes an HIL 440, an HTL 450, an EML 460, an ETL 470 and an EIL 480 each of which is laminated sequentially above the first electrode 410. In addition, the emission layer 430 further includes a first exciton blocking layer, i.e. an EBL 455 disposed between the HTL 450 and the EML 460 and/or a second exciton blocking layer, i.e., a HBL 475 disposed between the EML 460 and the ETL 470.

As described above, the first electrode 410 may be an anode and include a conductive material having a relatively large work function values such as ITO, IZO, SnO, ZnO, ICO, AZO, and the like. The second electrode 420 may be a cathode and include a conductive material having a relatively small work function values such as Al, Mg, Ca, Ag, alloy thereof or combination thereof. As an example, each of the first and second electrodes 410 and 420 may be laminated with a thickness of, but is not limited to, about 30 nm to about 300 nm.

The HL 440 is disposed between the first electrode 410 and the HTL 450. The HIL 440 may include, but is not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HL 440 may be omitted in compliance with the structure of the OLED 400.

The HTL 450 is disposed adjacently to the EML 460 between the first electrode 410 and the EML 460. The HTL 450 may include, but is not limited to, aromatic amine compounds such as TPD, NPD(NPB), CBP, poly-TPD, TFB, TAPC,), N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

In one exemplary embodiment, each of the HIL 440 and the HTL 450 may be laminated with a thickness of, but is not limited to, about 5 nm to about 200 nm, preferably about 5 nm to about 100 nm.

In this embodiment, the EML 460 includes a host (first host), a first dopant and a second dopant. As an example, the organic compound represented by any one of Chemical Formulae 1 to 11 and having delayed fluorescence properties may be used as the first dopant (T dopant), and a fluorescent or a phosphorescent material may be used as the second dopant (F dopant).

The ETL 470 is disposed between the EML 460 and the EIL 480. For example, the ETL 470 may include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like. As an example, the ETL 470 may comprise, but is not limited to, $Alq_3$, PBD, spiro-PBD, Liq, TPBi, BAlq, Bphen, NBphen, BCP, TAZ, NTAZ, TpPyPB, TmPPPyTz, PFNBr and/or TPQ.

The EIL 480 is disposed between the second electrode 420 and the ETL 470. The EIL 480 may include, but is not limited to, an alkali halide such as LiF, CsF, NaF, $BaF_2$ and the like, and/or an organic metal compound such as lithium benzoate, sodium stearate, and the like. For example, each of the ETL 470 and the EIL 480 may be laminated with a thickness of, but is not limited to, about 10 nm to about 200 nm, preferably about 10 nm to about 100 nm.

When holes are transferred to the second electrode 420 via the EML 460 and/or electrons are transferred to the first electrode 410 via the EML 460, the OLED 400 may have a short luminous life span and a reduced luminous efficiency. In order to prevent these phenomena, the OLED 400 in accordance with this embodiment of the present disclosure has at least one exciton blocking layer adjacently to the EML 460.

For example, the OLED 400 of the exemplary embodiment includes the EBL 455 between the HTL 450 and the EML 460 so as to control and prevent electron transfers. In one exemplary embodiment, the EBL 455 may include, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, N,N'-bis[4-(bis(3-methylphenyl)amino)phenyl]-N,N'-diphenyl-[1,1'-biphenyl]-4,4'-diamine (DNTPD) and/or TDAPB.

In addition, the OLED 400 further includes the HBL 475 as a second exciton blocking layer between the EML 460 and the ETL 470 so that holes cannot be transferred from the EML 460 to the ETL 470. In one exemplary embodiment, the HBL 475 may include, but is not limited to, oxadiazole-based compounds, triazole-based compounds, phenanthroline-based compounds, benzoxazole-based compounds, benzothiazole-based compounds, benzimidazole-based compounds, and triazine-based compounds. For example, the HBL 475 may include a compound having a relatively low HOMO energy level compared to the emitting material in EML 460. The HBL 475 may include, but is not limited to, BCP, BAlq, $Alq_3$, PBD, spiro-PBD, Liq, Bis-4,5-(3,5-di-3-pyridylphenyl)-2-methylpyrimidine (B3PYMPM) and combination thereof.

For example, each of the EBL 455 and the HBL 475 may be laminated with a thickness of, but is not limited to, about 5 nm to about 200 nm, preferably about 10 nm to about 100 nm.

In the above embodiment, the EML 360 includes only the first dopant, i.e. the organic compound represented by any one of Chemical Formulae 1 to 11 and having the delayed fluorescence properties. As described above, the delayed fluorescent material may implement internal quantum efficiency as the phosphorescent material including the heavy metals since it can exhibit 100% luminous efficiency maximally in theory.

However, the delayed fluorescent material has various geometries owing to the linkage structures and the conformational twists between the electron donor-acceptor, which causes additional charge transfer transition (CT transition) in the molecule. As a result, the delayed fluorescent material shows emission spectrum having very broad FWHM in emitting lights, which results in poor color purity. In addition, the delayed fluorescent material uses the triplet exciton energy as well as the singlet exciton energy in the luminous process with rotating each moiety within the molecule, which results in Twisted Internal Charge Transfer (TICT). As a result, the molecular bonding force within the delayed fluorescent material lowers so that the OLED including the delayed fluorescent material, to deteriorate luminous life span.

In this embodiment, the EML 460 further includes the second dopant, which is the fluorescent material or the phosphorescent material, so that the OLED 400 may prevent the EML 460 from lowering its color purity and its luminous life span caused by the delayed fluorescent material. Accordingly, The OLED 400 can implement hyper-fluorescence by converting the triplet exciton energy of the first dopant (T dopant) having the delayed fluorescent properties to the singlet exciton energy and then transferring the converted singlet exciton energy of the first dopant to the second dopant within the same EML though Dexter energy transfer mechanism, which depends upon wave function overlaps among adjacent molecules by inter-molecular electron exchanges and exciton diffusions, as illustrated in FIG. 6.

When the EML 460 includes the first host, the first dopant (T dopant), which is the organic compound represented by any one of Chemical Formulae 1 to 11 and having delayed fluorescent properties, and the second dopant (F dopant), which is the fluorescent material or the phosphorescent material, the exciton energy levels among the host and the dopant should be properly adjusted.

As described above, an energy bandgap "$\Delta E_{ST}^{TD}$" between the excited stated singlet energy level $S_1^{TD}$ and the excited stated triplet energy level $T_1^{TD}$ of the first dopant, i.e. the organic compound represented by any one of Chemical Formulae 1 to 11 may be equal to or less than about 0.3 eV so as to implement delayed fluorescence (See, FIG. 3). In addition, as illustrated in FIG. 6, each of an excited state singlet energy level $S_1^H$ and an excited state triplet energy level $T_1^H$ of the host must be higher than each of an excited state singlet energy level $S_1^{TD}$ and an excited state triplet energy level $T_1^{TD}$ of the first dopant, respectively. For example, the excited state triplet energy level $T_1^H$ of the host may be higher than the excited stated triplet energy level $T_1^{TD}$ of the first dopant by at least about 0.2 eV. When the excited state triplet energy level $T_1^H$ of the host is not higher enough than the excited state triplet energy level $T_1^{TD}$ of the first dopant, the excitons of the triplet state level $T_1^{TD}$ of the first dopant may be reversely transferred to the excited state triplet energy level $T_1^H$ of the host. Accordingly, the excitons of the triplet state level $T_1^{TD}$ of the first dopant may be quenched as a non-emission and they cannot be involved in the emission processes.

In addition, it is necessary to implement OLED that enables transfer exciton energies, which has been converted to ICT complex state by RISC, from the delayed fluorescent dopant to the second dopant of the fluorescent or phosphorescent material in EML 460, and that has high luminous efficiency and color purity. In order to implement such an OLED, the excited stated singlet energy level $S_1^{TD}$ of the first dopant may be higher than an excited state singlet energy level $S_1^{FD}$ of the second dopant. In addition, the excited stated triplet energy level $T_1^{TD}$ of the first dopant is higher than an excited state triplet energy level $T_1^{FD}$ of the second dopant.

Moreover, it is necessary to adjust properly Highest Occupied Molecular Orbital (HOMO) energy levels and Lowest Unoccupied Molecular Orbital (LUMO) energy levels of the host and the first dopant. For example, it is preferable that an energy level bandgap ($|HOMO^H$-$HOMO^{TD}|$) between a Highest Occupied Molecular Orbital energy level ($HOMO^H$) of the host and a Highest Occupied Molecular Orbital energy level ($HOMO^{TD}$) of the delayed fluorescent dopant, or an energy level bandgap ($|LUMO^H$-$LUMO^{TD}|$) between a Lowest Unoccupied Molecular Orbital energy level ($LUMO^H$) of the host and a Lowest Unoccupied Molecular Orbital energy level ($LUMO^{TD}$) of the first dopant may be equal to or less than about 0.5 eV, for example, between about 0.1 eV to about 0.5 eV.

In one exemplary embodiment, the host may include, but is not limited to, mCP-CN, CBP, mCBP, mCP, DPEPO, PPT, TmPyPB, PYD-2Cz, DCzDBT, DCzTP, pCzB-2CN, mCzB-2CN, TPSO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole 9-(6-(9H-carbazol-9-yl)pyridin-3-yl)-9H-3,9'-bicarbazole and/or 4-(3-triphenylen-2-yl)phenyl)dibenzo[b,d]thiophene.

Excitons energies must be transferred efficiently form the first dopant, i.e. delayed fluorescent material to the second dopant, i.e. fluorescent or phosphorescent material for implementing hyper-fluorescence. With regard to energy transfer efficiency from the delayed fluorescent material to the fluorescent or phosphorescent material, overlaps between the emission wavelength range of the delayed fluorescent material and the absorption wavelength range of the fluorescent or phosphorescent material receiving the excitons energies may be considered. As an example, a fluorescent or phosphorescent material having an absorption wavelength range having much overlapped area with an emission wavelength range of the first dopant, i.e. the organic compound represented by any one of Chemical Formulae 1 to 11.

In one exemplary embodiment, the fluorescent material as the second dopant may have, but is not limited to, a quinolino-acridine core. As an example, the second dopant having the quinolino-acridine core may include, but is not limited to, 5,12-dimethylquinolino[2,3-b]acridine-7,14(5H, 12H)-dione ($S_1$: 2.3 eV; $T_1$: 2.0 eV; LUMO: −3.0 eV; HOMO: −5.4 eV), 5,12-diethylquinolino[2,3-b]acridine-7,14(5H, 12H)-dione ($S_1$: 2.3 eV; $T_1$: 2.2 eV; LUMO: −3.0 eV; HOMO: −5.4 eV), 5,12-dibutyl-3,10-difluoroquinolino[2,3-b]acridine-7,14(5H, 12H)-dione ($S_1$: 2.2 eV; $T_1$: 2.0 eV; LUMO: −3.1 eV; HOMO: −5.5 eV), 5,12-dibutyl-3,10-bis(trifluoromethyl)quinolino[2,3-b]acridine-7,14(5H, 12H)-dione ($S_1$: 2.2 eV; $T_1$: 2.0 eV; LUMO: −3.1 eV; HOMO: −5.5 eV), 5,12-dibutyl-2,3,9,10-tetrafluoroquinolino[2,3-b]acridine-7,14(5H, 12H)-dione ($S_1$: 2.0 eV; $T_1$: 1.8 eV; LUMO: −3.3 eV; HOMO: −5.5 eV), and the like.

Alternatively, the fluorescent material as the second dopant may include, but is not limited to, 1,1,7,7-tetramethyl-2,3,6,7-tetrahydro-1H,5H-benzo[ij]quinolizin-9-yl)ethenyl]-4H-pyran-4-ylidene}propanedinitrile (DCJTB; $S_1$: 2.3 eV; $T_1$: 1.9 eV; LUMO: −3.1 eV; HOMO: −5.3 eV). Moreover, metal complexes emitting green light as the phosphorecent material may be used as the second dopant.

In an exemplary embodiment, a weight ratio of the host may be larger than weight ratios of the first and second dopants in the EML 460. In this case, the weigh ratio of the first dopant may be larger than the weight ratio of the second dopant. Alternatively, the weight ratio of the host is larger than the weight ratio of the first dopant and the weigh ratio of the first dopant may be larger than the weight ratio of the second dopant. For example, when the weight ratio of the first dopant is larger than the weight ratio of the second dopant, the energy transfer from the first dopant to the second dopant through Dexter mechanism may be done enougly. For example, the EML 460 may comprise the first host of about 60 to about 75% by weight, the first dopant of about 20 to about 40% by weight and the second dopant of about 0.1 to about 5% by weight.

The EML 460 may be laminated with a thickness of, but is not limited to, between about 10 nm and about 200 nm, preferably between about 20 nm and about 100 nm, and more preferably between about 30 nm and about 50 nm.

Figure 7:
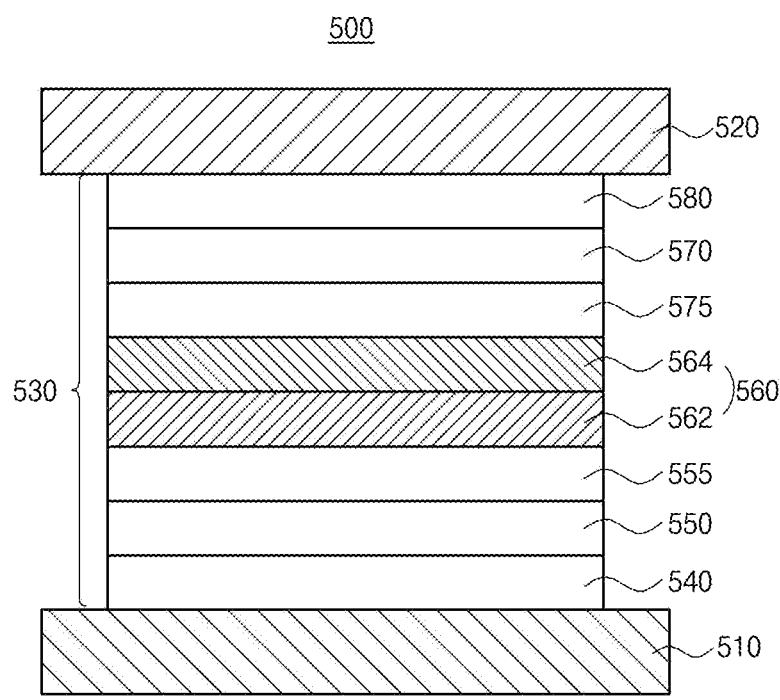
FIG. 7 is a schematic cross-sectional view illustrating an organic light-emitting diode in accordance with another exemplary embodiment of the present disclosure.
Figure 8:
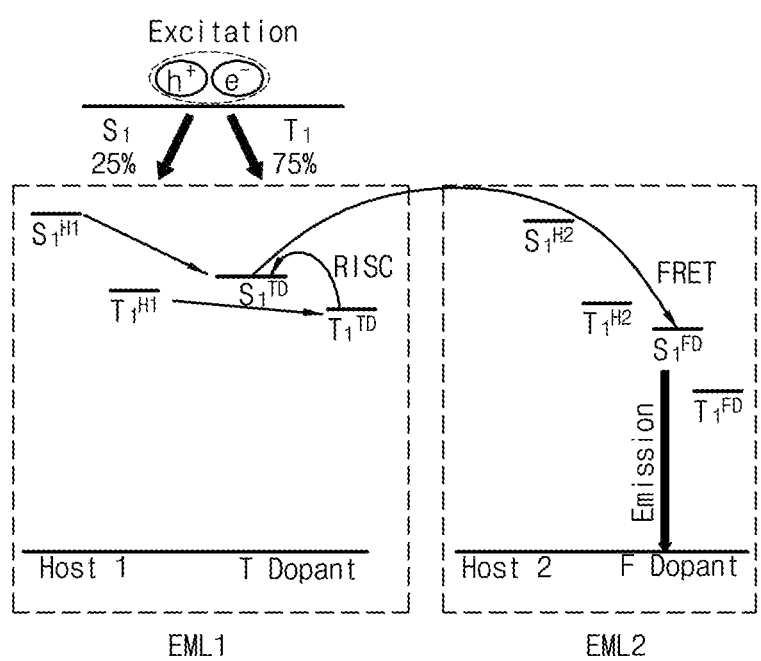
FIG. 8 is a schematic diagram illustrating the luminous mechanism by the energy level bandgap among a host, a delayed fluorescent material and a fluorescent material in a double-layered EML in accordance with another exemplary embodiment of the present disclosure.

In the above embodiment, the OLED 300 or 400 includes a single-layered EML 360 or 460. Unlikely those embodiment, an OLED of the present disclosure may have multiple-layered EML. FIG. 7 is a schematic cross-sectional view illustrating an organic light-emitting diode in accordance with another exemplary embodiment of the present disclosure and FIG. 8 FIG. 8 is a schematic diagram showing luminous mechanism by energy level bandgap among a host, an organic compound having delayed fluorescence properties and a fluorescent material in a double-layered EML in accordance with another exemplary embodiment of the present disclosure.

As illustrated in FIG. 7, the OLED 500 in accordance with another exemplary embodiment of the present disclosure includes first and second electrodes 510 and 520 facing each other and an emission layer 530 disposed between the first and second electrodes 510 and 520, as an emissive unit.

In one exemplary embodiment, the emission layer 530 includes an HIL 540, an HTL 550, and EML 560, an ETL 570 and an EIL 580 each of which is laminated sequentially over the first electrode 510. In addition, the emission layer 530 may include an EBL 555 as a first exciton blocking layer disposed between the HTL 550 and the EML 560, and/or an HBL 575 as a second exciton blocking layer disposed between the EML 560 and the ETL 570.

As described above, the first electrode 510 may be an anode and include a conductive material having a relatively large work function values such as ITO, IZO, SnO, ZnO, ICO, AZO, and the like. The second electrode 520 may be a cathode and include a conductive material having a relatively small work function values such as Al, Mg, Ca, Ag, alloy thereof or combination thereof.

The HL 540 is disposed between the first electrode 510 and the HTL 550. The HIL 540 may include, but is not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HL 540 may be omitted in compliance with the structure of the OLED 500.

The HTL 550 is disposed adjacently to the EML 560 between the first electrode 510 and the EML 560. The HTL 550 may include, but is not limited to, aromatic amine compounds such as TPD, NPD(NPB), CBP, poly-TPD, TFB, TAPC,), N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

In this embodiment, the EML 560 includes a first EML (EML1) 562 disposed between the EBL 555 and the HBL 575 and a second EML (EML2) 564 disposed between the EML1 562 and the HBL 575. One of the EML1 562 and the EML2 564 includes a first dopant (T dopant), i.e. the organic compound represented by any one of Chemical Formulae 1 to 11, and the other of the EML1 562 and the EML2 564 includes a second dopant, i.e. a fluorescent or phosphorescent material. Hereinafter, the EML 560, where the EML1 562 includes the first dopant and the EML2 564 includes the second dopant, will be explained.

The ETL 570 is disposed between the EML 560 and the EIL 580. For example, the ETL 570 may include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like. As an example, the ETL 570 may include, but is not limited to, $Alq_3$, PBD, spiro-PBD, Liq, TPBi, BAlq, Bphen, NBphen, BCP, TAZ, NTAZ, TpPyPB, TmPPPyTz, PFNBr and/or TPQ.

The EIL 580 is disposed between the second electrode 520 and the ETL 570. The EIL 580 may include, but is not limited to, an alkali halide such as LiF, CsF, NaF, $BaF_2$ and the like, and/or an organic metal compound such as lithium benzoate, sodium stearate, and the like.

The OLED 500 in accordance with this embodiment may include the EBL 555 between the HTL 550 and the EML 560 so as to control and prevent electron transfers. In one exemplary embodiment, the EBL 555 may include, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, N,N'-bis[4-(bis(3-methylphenyl)amino)phenyl]-N,N'-diphenyl-[1,1'-biphenyl]-4,4'-diamine (DNTPD) and/or TDAPB.

In addition, the OLED 500 may further include the HBL 575 as a second exciton blocking layer between the EML 560 and the ETL 570 so that holes cannot be transferred from the EML 560 to the ETL 570. In one exemplary embodiment, the HBL 575 may include, but is not limited to, oxadiazole-based compounds, triazole-based compounds, phenanthroline-based compounds, benzoxazole-based compounds, benzothiazole-based compounds, benzimidazole-based compounds, and triazine-based compounds. For example, the HBL 575 may include a compound having a relatively low HOMO energy level compared to the emitting material in EML 560. The HBL 575 may include, but is not limited to, BCP, BAlq, $Alq_3$, PBD, spiro-PBD, Liq, Bis-4, 5-(3,5-di-3-pyridylphenyl)-2-methylpyrimidine (B3PYMPM) and combination thereof.

The EML1 562 may include the first host and the first dopant, i.e. the organic compound represented by any one of Chemical Formulae 1 to 11 as the delayed fluorescent material, as described above. Since the first dopant in the EML1 562 has less energy bandgap between the excited state triplet energy level $T_1^{TD}$ and the excited singlet energy level $S_1^{TD}$ i.e. $\Delta E_{ST}^{TD}$ is equal to or less than about 0.3 eV (See, FIG. 3), the excited state triplet energy of the first dopant is converted to the excited state singlet energy level by RISC, and as a result, the first dopant has a high quantum efficiency. However, the first dopant has poor color purity owing to its wide FWHM.

On the other hand, the EML2 564 includes the second host and the second dopant, i.e. the fluorescent or phosphorescent material. While the second dopant of the fluorescent material has better color purity than the first dopant owing to its narrower FWHM, it has limited quantum efficiency caused by the fact the triplet excitons in the second dopant cannot be involved in the luminescence processes.

However, in this exemplary embodiment, both the singlet energy and the triplet energy of the first dopant having the delayed fluorescence properties in EML1 562 can be transferred to the second dopant in the EML2 564 disposed adjacently to the EML1 562 by FRET (Forster resonance energy transfer) that transfers energy non-radially through electrical fields by dipole-dipole interactions. Accordingly, the ultimate emission is done at the second dopant in the EML2 564.

In other words, the triplet energy of the first dopant in the EML1 562 is converted to the singlet energy of the first dopant by RISC. The singlet energy of the first dopant is transferred to the singlet energy of the second dopant because the excited state singlet energy level $S_1^{TD}$ of the first dopant in the EML1 562 is higher than the excited state singlet energy level $S_1^{FD}$ of the second dopant (See, FIG. 8). The second dopant in the EML2 564 can emit light using both the singlet energy and the triplet energy.

It is possible to implement hyper-fluorescence as the exciton energy produced by the first dopant, i.e. the delayed fluorescent material in the EML1 562 is transferred efficiently to the second dopant in the EML2 564. In this case, the first dopant only acts as transferring energy to the second dopant. The EML1 562 including the first dopant is not involved in the ultimate emission process, while the EML2 564 including the second dopant emits light. Accordingly, the OLED 500 enhances quantum efficiencies and color purity owing to narrow FWHM of the second dopant.

Each of the EML1 562 and the EML2 564 includes the first host and the second host, respectively. The exciton energies produced by the first and second hosts must be transferred to the first dopant of the delayed fluorescent material to emit light in advance.

As illustrated in FIG. 8, each of excited state singlet energy levels $S_1^{H1}$ and $S_1^{H2}$ of the first and second hosts must be higher than an excited state singlet energy level $S_1^{TD}$ of the first dopant. In addition, each of excited state triplet energy levels $T_1^{H1}$ and $T_1^{H2}$ of the first and second hosts must be higher than an excited state triplet energy level $T_1^{TD}$ of the first dopant.

For example, when each of the excited state triplet energy levels $T_1^{H1}$ and $T_1^{H2}$ of the first and second hosts are not higher enough than the excited state triplet energy level $T_1^{TD}$, the excitons of the triplet state $T_1^{TD}$ of the first dopant may be reversely transferred to the excited state triplet energy levels $T_1^{H1}$ and $T_1^{H2}$ of the first and second hosts. Accordingly, the excitons of the triplet state $T_1^{TD}$ of the first dopant cannot be involved in the luminescence process because the triplet excitons transferred to each of the first and second hosts is quenched without luminescence. As an example, the excited stated triplet energy levels $T_1^{H1}$ and $T_1^{H2}$ of the first and second host are higher than the excited state triplet energy level $T_1^{TD}$ of the first dopant by at least of about 0.2 eV.

In addition, each of the excited state singlet energy level $S_1^{H2}$ and the excited state triplet energy level $T_1^{H2}$ of the second host may be higher than each of an excited state singlet energy level $S_1^{FD}$ and an excited state triplet energy level $T_1^{TD}$ of the second dopant. Accordingly, the singlet exciton energy produced in the second host may be transferred to the second dopant.

Moreover, it is necessary to implement OLED having high luminous efficiency and color purity with transferring exciton energy from the first dopant, which is converted to ICT complex state by RISC, in the EML1 562 to the second dopant, which is a fluorescent material or a phosphorescent material, in the EML2 564. For implementing such OLED, the excited state singlet energy level $S_1^{TD}$ of the first dopant, which is a delayed fluorescent material, in the EML1 562 may be higher than the excited state singlet energy level $S_1^{FD}$ of the second dopant, which is a fluorescent or phosphorescent material, in the EML2 564. In addition, the excited state triplet energy level $T_1^{TD}$ of the first dopant in the EML1 562 is higher than the excited state triplet energy level $T_1^{FD}$ of the second dopant in the EML2 564

In addition, an energy level bandgap ($|HOMO^H-HOMO^{TD}|$) between a Highest Occupied Molecular Orbital energy level ($HOMO^H$) of the first and/or second hosts and a Highest Occupied Molecular Orbital energy level ($HOMO^{TD}$) of the first dopant, or an energy level bandgap ($|LUMO^H-LUMO^{TD}|$) between a Lowest Unoccupied Molecular Orbital energy level ($LUMO^H$) of the first and/or second hosts and a Lowest Unoccupied Molecular Orbital energy level ($LUMO^{TD}$) of the first dopant may be equal to or less than about 0.5 eV. Unless satisfying such energy level relationships, the OLED 500 may have reduced quantum efficiency owing to quenching phenomena at the first and second dopants and/or poor exciton energy transfer among the hosts and the dopants.

The first host may be identical to or different from the second host. For example, each of the first and second hosts may include, but is not limited to, mCP-CN, CPB, mCBP, mCP, DPEPO, PPT, TmPyPB, PYD-2Cz, DCzDBT, DCzTPA, pCzB-2CN, mCzB-2CN, TPSO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole 9-(6-(9H-carbazol-9-yl)pyridin-3-yl)-9H-3,9'-bicarbazole and/or 4-(3-triphenylen-2-yl)phenyl)dibenzo[b,d]thiophene, respectively.

The second dopant may have a narrow FWHM and a emission wavelength range having much overlapped area with the absorption wavelength range of the first dopant. For example, the second dopant may include, but is not limited to, an organic compound having a quinolino-acridine core such as 5,12-dimethyl quinolino[2,3-b]acridine-7,14(5H, 12H)-dione, 5,12-diethylquinolino[2,3-b]acridine-7,14(5H, 12H)-dione, 5,12-dibutyl-3,10-difluoroquinolino[2,3-b] acridine-7,14(5H, 12H)-dione, 5,12-dibutyl-3,10-bis(trifluoromethyl)quinolino[2,3-b]acridine-7,14(5H, 12H)-dione and/or 5,12-dibutyl-2,3,9,10-tetrafluoroquinolino[2,3-b] acridine-7,14(5H, 12H)-dione; DCJTB; or metal complexes emitting green light.

In an exemplary embodiment, each of the first and second hosts may have a weight ratio equal to or higher than each of the first and second dopants in the same EML. In addition, the weigh ratio of the first dopant in the EML1 562 may be larger than the weight ratio of the second dopant in the EML2 564. Accordingly, exciton energy may be transferred efficiently form the first dopant in the EML1 562 to the second dopant in the EML2 564.

Alternatively, the weight ratio of the first host is larger than the weight ratio of the first dopant in the EML1 562. For example, the EML1 562 may comprise the first host of about 50 to about 99% by weight, preferably about 60 to about 90% by weight, and more preferably about 60 to about 80% by weight, and the first dopant of about 1 to about 50% by weight, preferably about 10 to about 40% by weight, and more preferably about 20 to about 40% by weight.

In addition, the weight ratio of the second host is larger than the weight ratio of the second dopant in the EML2 564. For example, the EML2 564 may comprise the second host of about 90 to about 99% by weight, preferably about 95 to about 99% by weight, and the second dopant of about 1 to about 10% by weight, preferably about 1 to about 5% by weight.

In an exemplary embodiment, each of the EML1 562 and the EML2 564 may be laminated with a thickness of, but is not limited to, about 5 nm to about 100 nm, preferably about 10 nm to about 30 nm, and more preferably about 10 nm to about 20 nm.

In case the EML2 564 is located adjacently to the HBL 575 in accordance with an exemplary embodiment, the second host in the EML2 564 may be the same material as the HBL 575. In this case, the EML2 564 may have a hole blocking function as well as an emission function. In other words, the EML2 564 can act as a buffer layer for blocking holes. In one embodiment, the HBL 575 may be omitted where the EML2 564 may be a hole blocking layer as well as an emitting material layer.

In case the EML2 564 is located adjacently to the EBL 555 in accordance with another exemplary embodiment, the second host in the EML2 564 may be the same material as the EBL 555. In this case, the EML2 564 may have an electron blocking function as well as an emission function. In other words, the EML2 564 can act as a buffer layer for blocking electrons. In one embodiment, the EBL 555 may be omitted where the EML2 564 may be an electron blocking layer as well as an emitting material layer.

Figure 9:
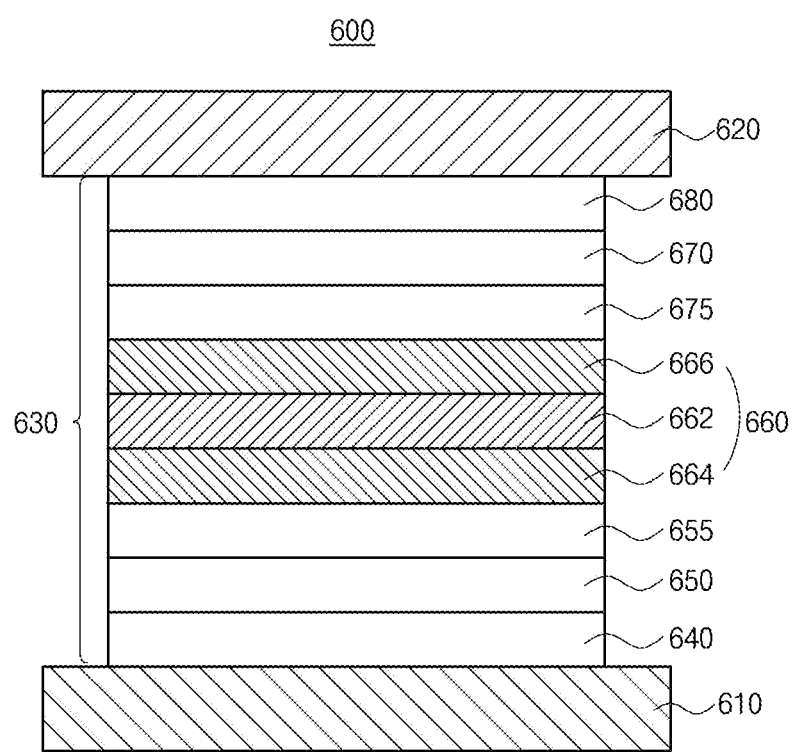
FIG. 9 is a schematic cross-sectional view illustrating an organic light-emitting diode in accordance with another exemplary embodiment of the present disclosure.
Figure 10:
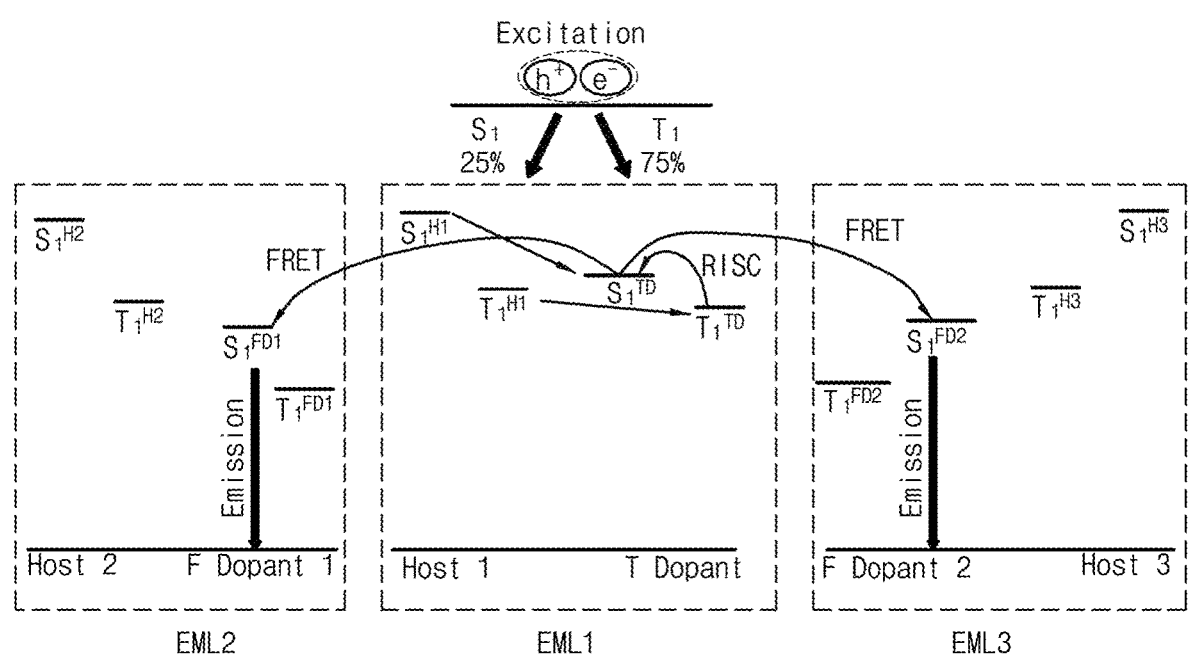
FIG. 10 is a schematic diagram illustrating the luminous mechanism by the energy level bandgap among a host, a delayed fluorescent material and a fluorescent material in a triple-layered EML in accordance with another exemplary embodiment of the present disclosure.

An OLED having three-layered EML will be exampled. FIG. 9 is a schematic cross-sectional view illustrating an organic light-emitting diode in accordance with still another exemplary embodiment of the present disclosure and FIG. 10 is a schematic diagram showing luminous mechanism by energy level bandgap among a host, an organic compound having delayed fluorescence properties and a fluorescent material in a triple-layered EML in accordance with still another exemplary embodiment of the present disclosure.

As illustrated in FIG. 9, the OLED 600 in accordance with still another exemplary embodiment of the present disclosure includes first and second electrodes 610 and 620 facing each other and an emission layer 630 disposed between the first and second electrodes 610 and 620, as an emitting unit.

In one exemplary embodiment, the emission layer 630 includes an HL 640, an HTL 650, and EML 660, an ETL 670 and an EIL 680 each of which is laminated sequentially over the first electrode 610. In addition, the emission layer 630 may include an EBL 655 as a first exciton blocking layer disposed between the HTL 650 and the EML 660, and/or an HBL 675 as a second exciton blocking layer disposed between the EML 660 and the ETL 670.

As described above, the first electrode 610 may be an anode and include a conductive material having a relatively large work function values such as ITO, IZO, SnO, ZnO, ICO, AZO, and the like. The second electrode 620 may be a cathode and include a conductive material having a relatively small work function values such as Al, Mg, Ca, Ag, alloy thereof or combination thereof.

The HL 640 is disposed between the first electrode 610 and the HTL 650. The HIL 640 may include, but is not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 640 may be omitted in compliance with the structure of the OLED 600.

The HTL 650 is disposed adjacently to the EML 660 between the first electrode 610 and the EML 660. The HTL 650 may include, but is not limited to, aromatic amine compounds such as TPD, NPD(NPB), CBP, poly-TPD, TFB, TAPC,), N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

In this embodiment, the EML 660 includes a first EML (EML1) 662 disposed between the EBL 655 and the HBL 675, a second EML (EML2) 664 disposed between the EBL 655 and the EML1 662 and a third EML (EML3) 666 disposed between the EML1 662 and the HBL 675.

The ETL 670 is disposed between the EML 660 and the EIL 680. For example, the ETL 670 may include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like. As an example, the ETL 670 may include, but is not limited to, Alq$_3$, PBD, spiro-PBD, Liq, TPBi, BAlq, Bphen, NBphen, BCP, TAZ, NTAZ, TpPyPB, TmPPPyTz, PFNBr and/or TPQ.

The EIL 680 is disposed between the second electrode 620 and the ETL 670. The EIL 680 may include, but is not limited to, an alkali halide such as LiF, CsF, NaF, BaF$_2$ and the like, and/or an organic metal compound such as lithium benzoate, sodium stearate, and the like.

The OLED 600 in accordance with this embodiment may include the EBL 655 between the HTL 650 and the EML 660 so as to control and prevent electron transfers. In one exemplary embodiment, the EBL 655 may include, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, N,N'-bis[4-(bis(3-methylphenyl)amino)phenyl]-N,N'-diphenyl-[1,1'-biphenyl]-4,4'-diamine (DNTPD) and/or TDAPB.

In addition, the OLED 600 may further include the HBL 675 as a second exciton blocking layer between the EML 660 and the ETL 670 so that holes cannot be transferred from the EML 660 to the ETL 670. In one exemplary embodiment, the HBL 675 may include, but is not limited to, oxadiazole-based compounds, triazole-based compounds, phenanthroline-based compounds, benzoxazole-based compounds, benzothiazole-based compounds, benzimidazole-based compounds, and triazine-based compounds. For example, the HBL 675 may include a compound having a relatively low HOMO energy level compared to the emitting material in EML 660. The HBL 675 may include, but is not limited to, BCP, BAlq, Alq$_3$, PBD, spiro-PBD, Liq, Bis-4,5-(3,5-di-3-pyridylphenyl)-2-methylpyrimidine (B3PYMPM) and combination thereof.

The EML1 662 include a first dopant (T dopant), i.e. the organic compound represented by any one of Chemical Formulae 1 to 11 as the delayed fluorescent material. Each of the EML2 664 and the EML3 666 includes a first dopant and second dopant, respectively, i.e. the fluorescent or phosphorescent material. In addition, each of the EML1 662, the EML2 664 and the EML3 666 includes a first host, a second host and a third host, respectively.

In accordance with this embodiment, both the singlet energy and the triplet energy of the first dopant (T dopant), i.e. the organic compound represented by any one of Chemical Formulae 1 to 11 as the delayed fluorescent material in the EML1 662 can be transferred to the second and third dopants, i.e. the fluorescent or phosphorescent material, in the EML2 664 and the EML3 666 disposed adjacently to the EML1 662 by FRET (Foster resonance energy transfer). Accordingly, the ultimate emission is done at the second and third dopants in the EML2 664 and the EML3 666.

In other words, the triplet energy of the first dopant in the EML1 662 is converted to the singlet energy of the first dopant by RISC. The singlet energy level of the first dopant, i.e. the delayed fluorescent material in the EML1 662 is higher than singlet energy levels of the second and third dopants, i.e. the fluorescent or phosphorescent material in the EML2 664 and the EML3 666. The singlet energy of the first dopant in the EML1 662 is transferred to the singlet energies of the second and third dopant in the EML2 664 and the EML3 666, each of which is adjacently located to the EML1 662, through FRET mechanism.

Accordingly, the second and third dopant in the EML2 664 and the EML3 666 emit lights using triplet energy as well as singlet energy. Since the second and third dopants have narrower FWHM compared to the first dopant, the OLED 600 has enhanced luminous efficiencies and color purity owing to the narrower FWHM. Particularly, in case the second and third dopant have luminescence spectra with a large overlapped area with the absorption spectrum of the first dopant, the exciton energy can be transferred efficiently to the second and third dopant from the first dopant. In this case, ultimate emission is done in the EML2 664 and the EML666 each of which includes the second dopant and the third dopant, respectively. It is necessary to adjust properly energy levels among the hosts and the dopants in the EML1 662, the EML2 664 and the EML3 666 for implementing efficient luminescence in the EML 660.

As illustrated in FIG. 10, each of excited state singlet energy levels $S_1^{H1}$, $S_1^{H2}$ and $S_1^{H3}$ of the first, second and third hosts and excited state triplet energy levels $T_1^{H1}$, $T_1^{H2}$ and $T_1^{H3}$ of the first, second and third hosts must be higher than each of the excited state singlet energy level $S_1^{TD}$ and the excited state triplet energy level $T_1^{TD}$ of the first dopant that is a delayed fluorescent material.

For example, when the excited state triplet energy levels $T_1^{H1}$, $T_1^{H2}$ and $T_1^{H3}$ of the first, second and third hosts are not higher enough than the excited state triplet energy level $T_1^{TD}$, the excitons of the triplet state $T_1^{TD}$ of the first dopant may be reversely transferred to the excited state triplet energy levels $T_1^{H1}$, $T_1^{H2}$ and $T_1^{H3}$ of the first, second and third hosts. Accordingly, the excitons of the triplet state $T_1^{TD}$ of the first dopant cannot be involved in the luminescence process because the triplet excitons transferred to the hosts is quenched without luminescence.

In addition, it is necessary to implement OLED having high luminous efficiency and color purity with transferring exciton energy from the first dopant, which is converted to ICT complex state by RISC, in the EML1 662 to the second and third dopants, each of which is a fluorescent material or a phosphorescent material, in the EML2 664 and the EML3 666. For implementing such OLED, the excited state singlet energy level $S_1^{TD}$ of the first dopant, which is delayed fluorescent material, in the EML1 662 may be higher than each of excited stated singlet energy levels $S_1^{FD1}$ and $S_1^{FD2}$ of the second and third dopants, each of which is a fluorescent or phosphorescent material, in the EML2 664 and EML3 666, respectively. Moreover, the excited state triplet energy level $T_1^{TD}$ of the first dopant in the EML1 662 is higher than each of excited stated triplet energy levels $T_1^{FD1}$ and $T_1^{FD2}$ of the second and third dopant in the EML2 664 and EML3 666, respectively.

Moreover, the energy transferred from the first dopant, i.e. the delayed fluorescent material to the second and third dopants, i.e. fluorescent material or phosphorescent material should not be transferred reversely to the second and third hosts so as to implement efficient luminescence. With regard to efficient luminescence, each of the excited state singlet energy level $S_1^{H2}$ and $S_1^{H3}$ of the second and third host must be higher than each of the excited state singlet energy level $S_1^{FD1}$ and $S_1^{D2}$ of the second and third dopants, respectively. The first dopant may have an energy bandgap $\Delta E_{ST}^{TD}$ equal to or less than about 0.3 eV, for example, from about 0.05 to about 0.3 eV, between the singlet energy level $S_1^{TD}$ and the triplet energy level $T_1^{TD}$ so as to implement delayed fluorescence.

In addition, an energy level bandgap ($|HOMO^H$-$HOMO^{TD}|$) between a Highest Occupied Molecular Orbital energy level ($HOMO^H$) of the first, second and/or third hosts and a Highest Occupied Molecular Orbital energy level ($HOMO^{TD}$) of the first dopant, or an energy level bandgap ($|LUMO^H$-$LUMO^{TD}|$) between a Lowest Unoccupied Molecular Orbital energy level ($LUMO^H$) of the first, second and/or third hosts and a Lowest Unoccupied Molecular Orbital energy level ($LUMO^{TD}$) of the first dopant may be equal to or less than about 0.5 eV.

Each of the EML1 662, the EML2 664 and the EML3 666 may include the first host, the second host and the third host, respectively. Each of the first, second and third hosts may be identical to or different from each other. For example, each of the first, second and third hosts may include, but is not limited to, mCP-CN, CPB, mCBP, mCP, DPEPO, PPT, TmPyPB, PYD-2Cz, DCzDBT, DCzTPA, pCzB-2CN, mCzB-2CN, TPSO1, CCP, 4-(3-(triphenylen-2-yl)phenyl) dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole 9-(6-(9H-carbazol-9-yl)pyridin-3-yl)-9H-3,9'-bicarbazole and/or 4-(3-triphenylen-2-yl)phenyl)dibenzo[b, d]thiophene, respectively.

Each of the second and third dopants may have a narrow FWHM and an emission wavelength range having much overlapped area with the absorption wavelength range of the first dopant. For example, each of the second and third dopants may include, but is not limited to, an organic compound having a quinolino-acridine core such as 5,12-dimethylquinolino[2,3-b]acridine-7,14(5H, 12H)-dione, 5,12-diethylquinolino[2,3-b]acridine-7,14(5H, 12H)-dione, 5,12-dibutyl-3,10-difluoroquinolino[2,3-b]acridine-7,14 (5H, 12H)-dione, 5,12-dibutyl-3,10-bis(trifluoromethyl)quinolino[2,3-b]acridine-7,14(5H, 12H)-dione and/or 5,12-dibutyl-2,3,9,10-tetrafluoroquinolino[2,3-b]acridine-7,14 (5H, 12H)-dione; DCJTB; or metal complexes emitting green light, respectively.

In an exemplary embodiment, each of the first, second and third hosts may have a weight ratio equal to or higher than each of the first, second and third dopants in the same EML. In addition, the weigh ratio of the first dopant in the EML1 662 may be larger than the weight ratios of the second and third dopants in the EML2 664 and the EML3 666, respectively. Accordingly, exciton energy may be transferred efficiently form the first dopant in the EML1 662 to the second and third dopants in the EML2 664 and the EML3 666.

Alternatively, the weight ratio of the first host is larger than the weight ratio of the first dopant in the EML1 662. For example, the EML1 662 may comprise the first host of about 50 to about 99% by weight, preferably about 60 to about 90% by weight, and more preferably about 60 to about 80% by weight, and the first dopant of about 1 to about 50% by weight, preferably about 10 to about 40% by weight, and more preferably about 20 to about 40% by weight.

In addition, the weight ratio of each of the second and third hosts is larger than the weight ratio of the second and third dopants in the EML2 664 and the EML3 666, respectively. For example, each of the EML2 664 and the EML3 666 may comprise the second or third host of about 90 to about 99% by weight, preferably about 95 to about 99% by weight, and the second or third dopant of about 1 to about 10% by weight, preferably about 1 to about 5% by weight.

In an exemplary embodiment, the EML1 662 may be laminated with a thickness of, but is not limited to, about 2 nm to about 30 nm, preferably about 2 nm to about 20 nm. In another exemplary embodiment, each of the EML2 664 and the EML3 666 may be laminated with a thickness of, but is not limited to, about 5 nm to about 100 nm, preferably about 10 nm to about 30 nm, and more preferably about 10 nm to about 20 nm.

In case the EML2 664 is located adjacently to the EBL 655 in accordance with another exemplary embodiment, the second host in the EML2 664 may be the same material as the EBL 655. In this case, the EML2 664 may have an electron blocking function as well as an emission function. In other words, the EML2 664 can act as a buffer layer for blocking electrons. In one embodiment, the EBL 655 may be omitted where the EML2 664 may be an electron blocking layer as well as an emitting material layer.

In case the EML3 666 is located adjacently to the HBL 675 in accordance with another exemplary embodiment, the third host in the EML3 666 may be the same material as the HBL 675. In this case, the EML3 666 may have a hole blocking function as well as an emission function. In other words, the EML3 666 can act as a buffer layer for blocking holes. In one embodiment, the HBL 675 may be omitted where the EML3 666 may be a hole blocking layer as well as an emitting material layer.

In still another exemplary embodiment, the second host in the EML2 664 may be the same material as the EBL 655 and the third host in the EML3 666 may be the same material as the HBL 675. In this embodiment, the EML2 664 may have an electron blocking function as well as an emission function, and the EML3 666 may have a hole blocking function as well as an emission function. In other words, each of the EML2 664 and the EML3 666 can act as a buffer layer for blocking electrons or hole, respectively. In one embodiment, the EBL 655 and the HBL 675 may be omitted where the EML2 664 may be an electron blocking layer as well as an emitting layer and the EML3 666 may be a hole blocking layer as well as an emitting material layer.

Synthesis Example 1: Synthesis of Compound 1-1

(1) Synthesis of Intermediate a

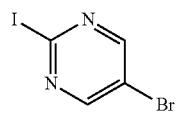

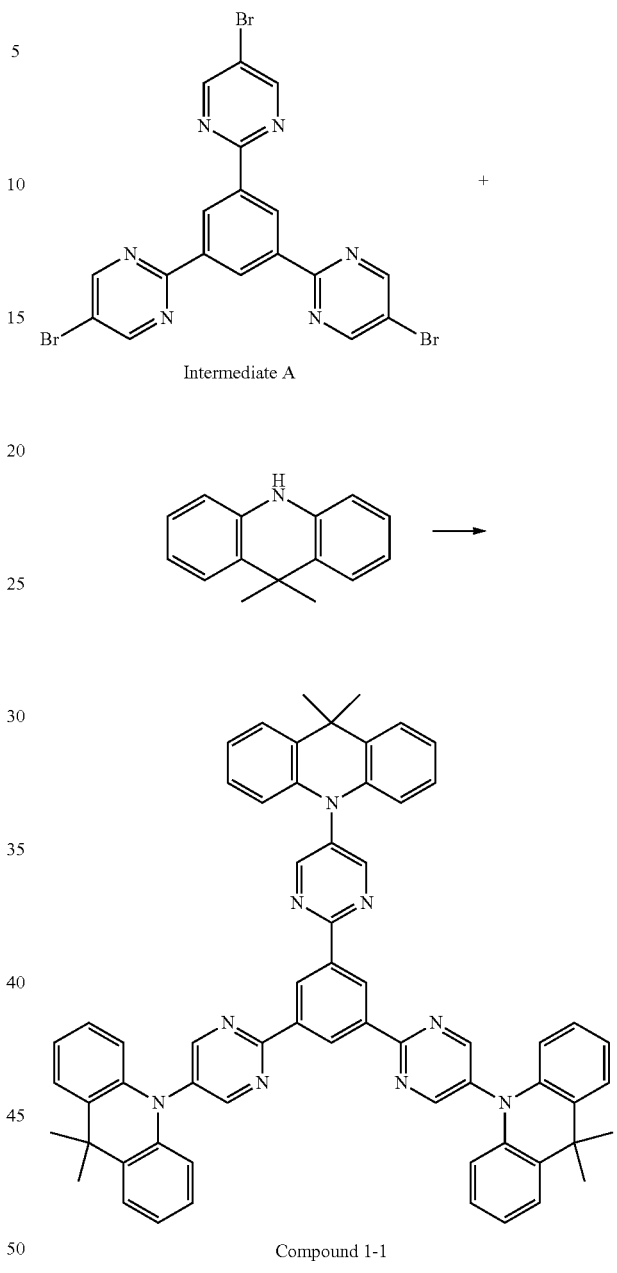

2.73 g (6 equivalents) of K$_2$CO$_3$ was dissolved in 30 mL of H$_2$O and stirred under nitrogen atmosphere. 3.75 g (4 equivalents) of 5-bromo-2-iodopyrimidine, 1.5 g (1 equivalent) of tris (pincaol) ester of 1,3,5-phenyltriboronic acid, 0.19 g (0.05 equivalents) of tetrakis(triphenylphosphine) palladium (0) (Pd(PPh$_3$)$_4$) and 90 mL of THF was added into the solution, and then the reaction mixture was refluxed and stirred over 96 hours to proceed a reaction. After the reaction was completed, the solution was cooled to room temperature, and extracted with ethyl acetate/H$_2$O, and the solvent was removed with MgSO$_4$. The solid was purified with column chromatography using hexane/methylene chloride (2:3) as a developing solvent and was recrystallized to give while solid intermediate A (yield=20%).

(2) Synthesis of Compound 1-1

0.3 g (1 equivalent) of Intermediate A and 0.46 g (4 equivalents) of 9,9-dimethyl-9,10-dihydroacridine was dissolved in 40 mL of toluene and stirred under nitrogen atmosphere. 0.15 g (0.3 equivalents) of tris(dibenzylideneacetone)dipalladium (0) (Pd$_2$(dba)$_3$), 0.33 g (0.3 equivalents) of tri-tert-butylphosphine and 0.79 g (15 equivalents) of sodium tert-butoxide was added into the solution, and then the reaction mixture was heated and stirred until being refluxed for 24 hours. After the reaction was completed, the solution was cooled to room temperature, and then was washed with distilled water and acetone. After washing the extract enough, the extract was purified with column chromatography using hexane/methylene chloride (2:3) as a developing solvent and was recrystallized to give yellow solid Compound 1-1 (yield=37%).

Synthesis Example 2: Synthesis of Compound 1-8

(1) Synthesis of Intermediate B

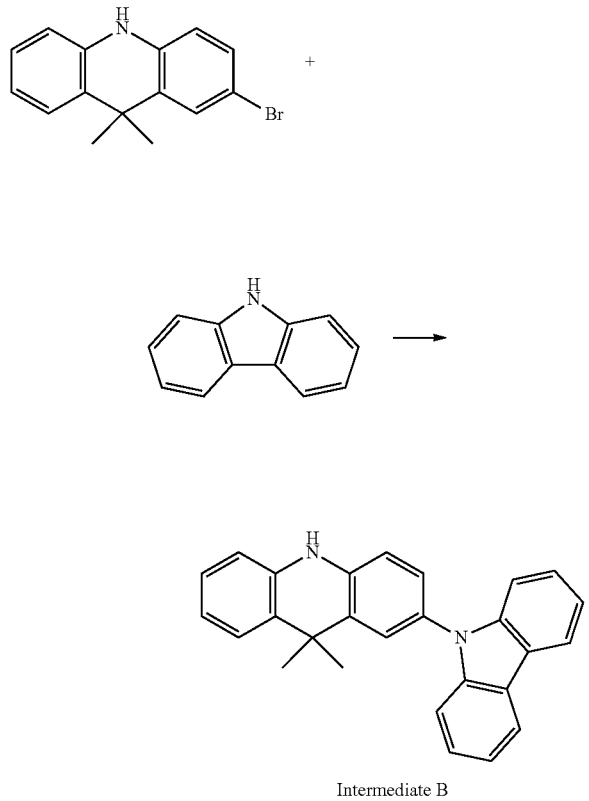

Intermediate B 2 g (1 equivalent) of 2-bromo-9,9-dimethyl-9,10-dihydroacrdine and 1.39 g (1.2 equivalents) of carbazole was dissolved in 50 mL of toluene and stirred under nitrogen atmosphere. 0.32 g (0.05 equivalents) of $Pd_2(dba)_3$, 0.14 g (0.1 equivalents) of tri-tert-butylphosphine and 2.00 g (3 equivalents) of sodium tert-butoxide was added into the solution, and then the reaction mixture was heated and stirred until being refluxed for 24 hours. After the reaction was completed, the solution was extracted with methylene chloride and distilled water. After removing the solvent, the solid was purified with column chromatography using hexane/methylene chloride (2:3) as a developing solvent and was recrystallized to give beige solid Intermediate B (yield=65%).

(2) Synthesis of Compound 1-8

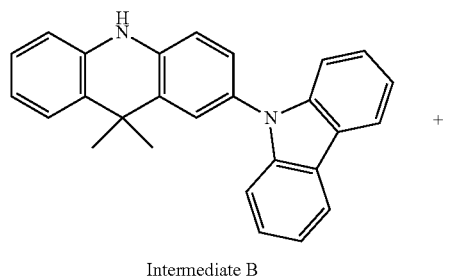

Intermediate B

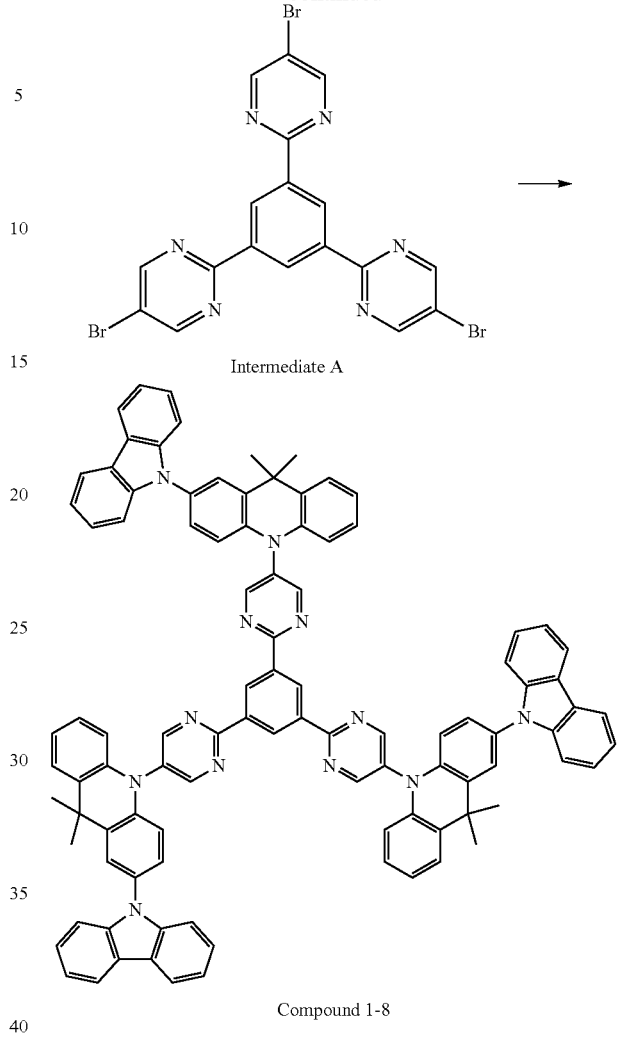

Intermediate A

Compound 1-8

1 g (1 equivalent) of Intermediate A and 2.73 g (4 equivalents) of Intermediate B was dissolved in 80 mL of toluene and stirred under nitrogen atmosphere. 0.15 g (0.3 equivalents) of $Pd_2(dba)_3$, 0.33 g (0.3 equivalents) of tri-tert-butylphosphine and 0.79 g (15 equivalents) of sodium tert-butoxide was added into the solution, and then the reaction mixture was heated and stirred until being refluxed for 24 hours. After the reaction was completed, the solution was cooled to room temperature, and then was washed with distilled water and acetone. After washing the extract enough, the extract was purified with column chromatography using hexane/methylene chloride (2:3) as a developing solvent and was recrystallized to give yellow solid Compound 1-8 (yield=37%).

Synthesis Example 3: Synthesis of Compound 1-10

(1) Synthesis of Intermediate C

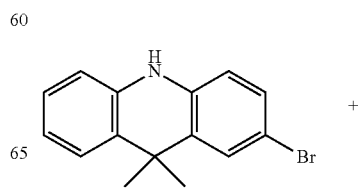

-continued

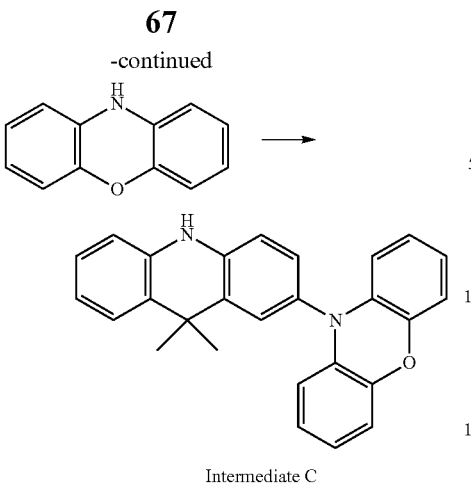

Intermediate C 2 g (1 equivalent) of 2-bromo-9,9-dimethyl-9,10-dihydroacrdine and 4.55 g (1.2 equivalents) of phenoxazine was dissolved in 50 mL of toluene and stirred under nitrogen atmosphere. 0.32 g (0.05 equivalents) of $Pd_2(dba)_3$, 0.14 g (0.1 equivalents) of tri-tert-butylphosphine and 2.00 g (3 equivalents) of sodium tert-butoxide was added into the solution, and then the reaction mixture was heated and stirred until being refluxed for 24 hours. After the reaction was completed, the solution was extracted with methylene chloride and distilled water. After removing the solvent, the solid was purified with column chromatography using hexane/methylene chloride (2:3) as a developing solvent and was recrystallized to give beige solid Intermediate C (yield=65%).

(2) Synthesis of Compound 1-10

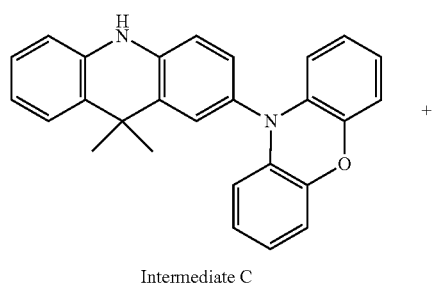

Intermediate C

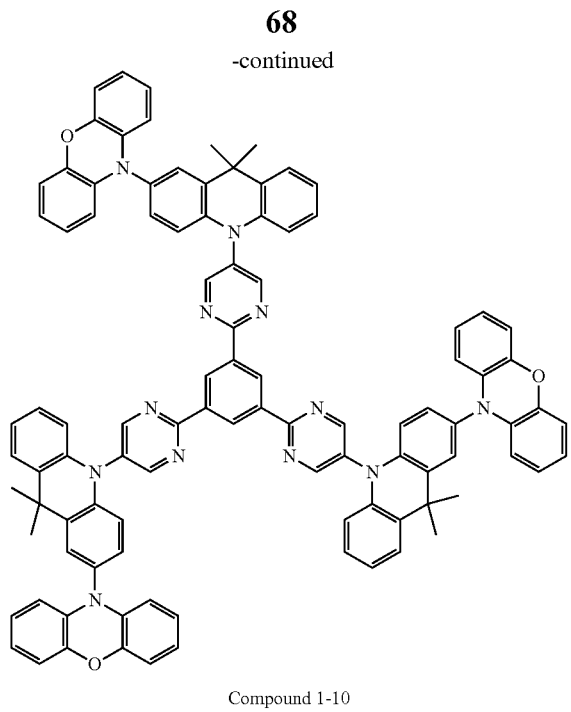

Compound 1-10

1 g (1 equivalent) of Intermediate A and 2.84 g (4 equivalents) of Intermediate C was dissolved in 80 mL of toluene and stirred under nitrogen atmosphere. 0.17 g (0.1 equivalents) of $Pd_2(dba)_3$, 0.04 g (0.3 equivalents) of tri-tert-butylphosphine and 1.58 g (9 equivalents) of sodium tert-butoxide was added into the solution, and then the reaction mixture was heated and stirred until being refluxed for 48 hours. After the reaction was completed, the solution was cooled to room temperature, and then was washed with distilled water and acetone. After washing the extract enough, the extract was purified with column chromatography using hexane/toluene (3:1→1:1→2:1) as a developing solvent and was recrystallized to give yellow solid Compound 1-10 (yield=49%).

Synthesis Example 4: Synthesis of Compound 2-1

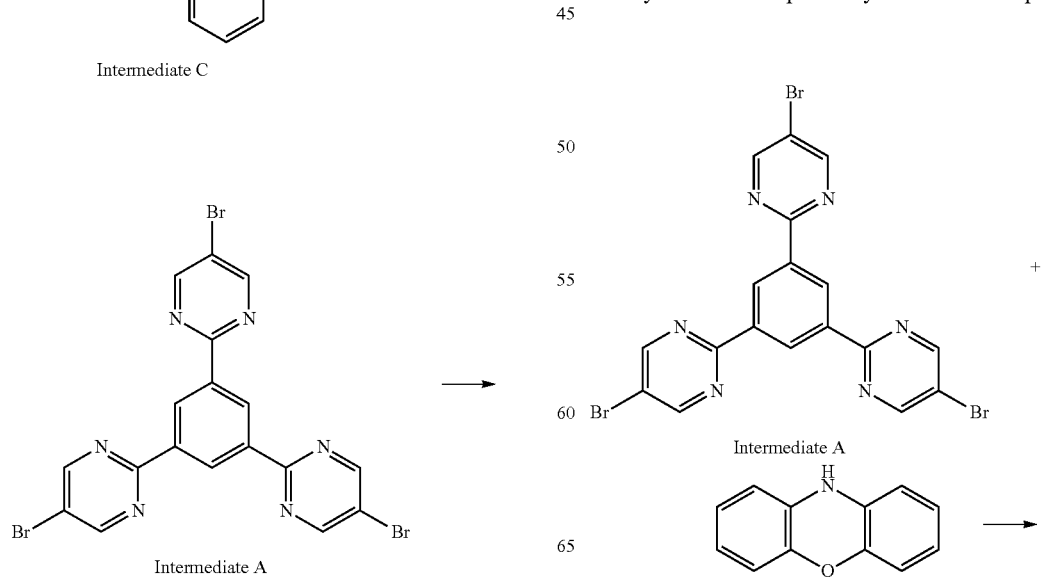

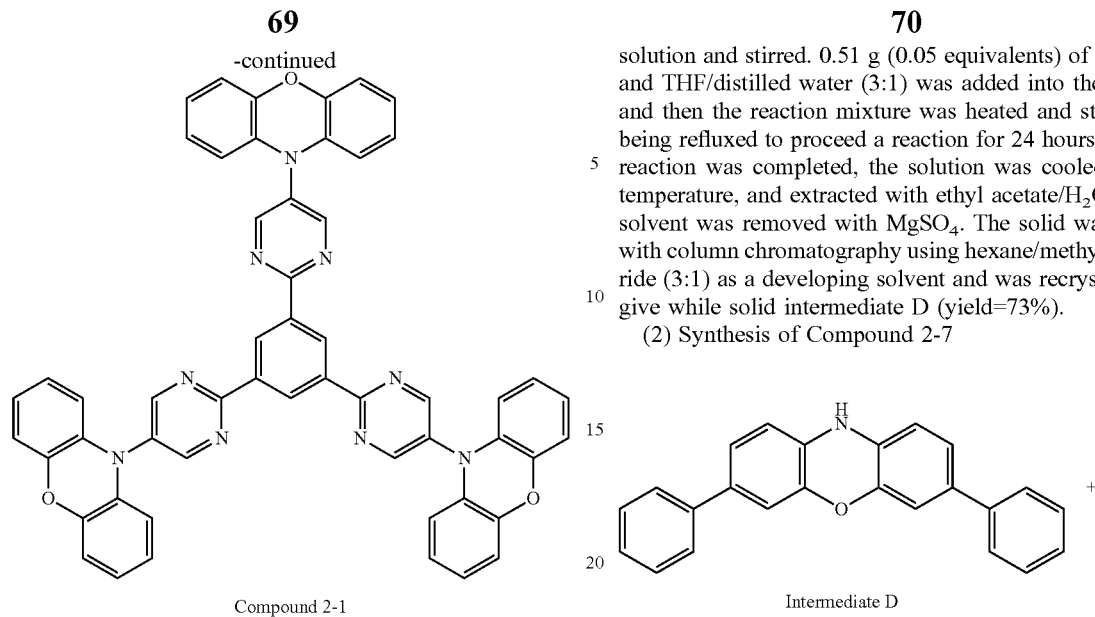

Compound 2-1

0.7 g (1 equivalent) of Intermediated A and 0.93 g (4 equivalent) of 2-bromo-9,9-dimethyl-9,10-dihydroacrdine was dissolved in 50 mL of toluene and stirred under nitrogen atmosphere. 0.35 g (0.3 equivalents) of $Pd_2(dba)_3$, 0.077 g (0.3 equivalents) of tri-tert-butylphosphine and 1.84 g (15 equivalents) of sodium tert-butoxide was added into the solution, and then the reaction mixture was heated and stirred until being refluxed for 24 hours. After the reaction was completed, the solution was cooled to room temperature, and then was washed with distilled water and acetone. After washing the extract enough, the extract was purified with column chromatography using hexane/methylene chloride (2:3) as a developing solvent and was recrystallized to give yellow solid Compound 2-1 (yield=46%).

Synthesis Example 5: Synthesis of Compound 2-7

(1) Synthesis of Intermediate D

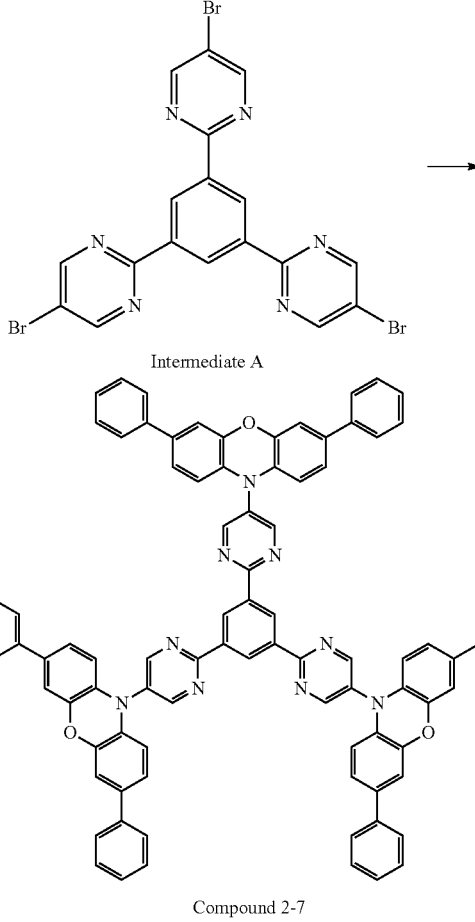

Intermediate D 3.65 g (3 equivalents) of $K_2CO_3$ was dissolved in $H_2O$ and stirred under nitrogen atmosphere. 3 g (1 equivalent) of 3,7-dibromo-10H-phenoxazine, 2.25 g (2.1 equivalents) of phenylboronic acid and 90 mL of THF was added into the solution and stirred. 0.51 g (0.05 equivalents) of $Pd(PPh_3)_4$ and THF/distilled water (3:1) was added into the solution, and then the reaction mixture was heated and stirred until being refluxed to proceed a reaction for 24 hours. After the reaction was completed, the solution was cooled to room temperature, and extracted with ethyl acetate/$H_2O$, and the solvent was removed with $MgSO_4$. The solid was purified with column chromatography using hexane/methylene chloride (3:1) as a developing solvent and was recrystallized to give while solid intermediate D (yield=73%).

(2) Synthesis of Compound 2-7

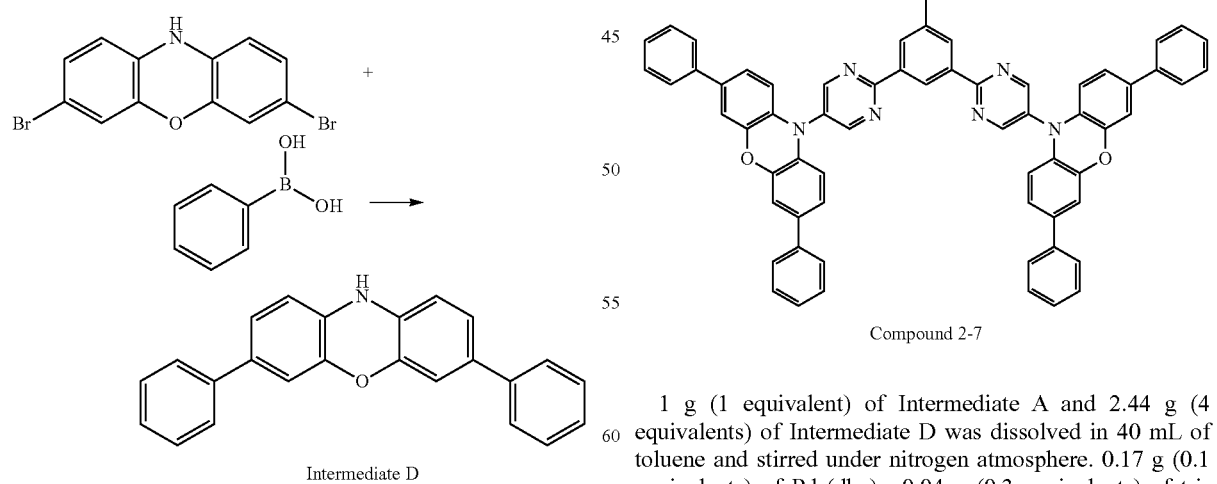

Compound 2-7

1 g (1 equivalent) of Intermediate A and 2.44 g (4 equivalents) of Intermediate D was dissolved in 40 mL of toluene and stirred under nitrogen atmosphere. 0.17 g (0.1 equivalents) of $Pd_2(dba)_3$, 0.04 g (0.3 equivalents) of tri-tert-butylphosphine and 1.58 g (9 equivalents) of sodium tert-butoxide was added into the solution, and then the reaction mixture was heated and stirred until being refluxed for 48 hours. After the reaction was completed, the solution was cooled to room temperature, and then was washed with distilled water and acetone. After washing the extract enough, the extract was purified with column chromatography using hexane/Toluene (3:1→1:1→2:1) as a developing solvent and was recrystallized to give yellow solid Compound 2-7 (yield=50%).

Synthesis Example 6: Synthesis of Compound 2-8

(1) Synthesis of Intermediate E

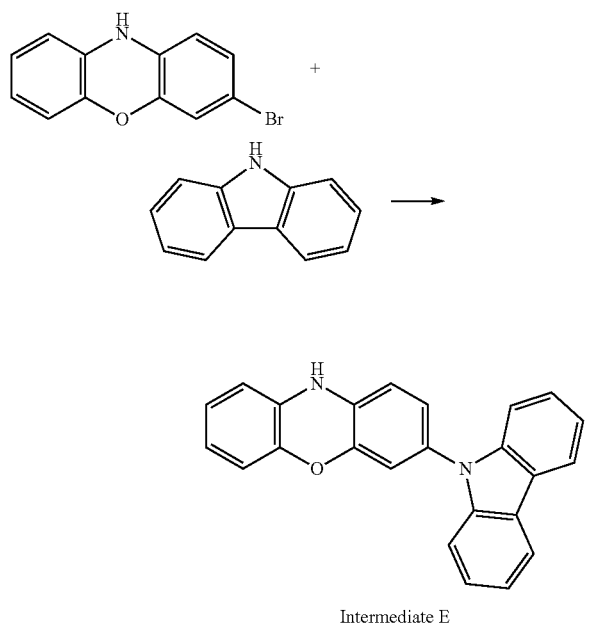

Intermediate E 2 g (1 equivalent) of 3-bromo-10H-phenoxazine and 1.53 g (1.2 equivalents) of carbazole was dissolved in 50 mL of toluene and stirred under nitrogen atmosphere. 0.32 g (0.05 equivalents) of Pd$_2$(dba)$_3$, 0.14 g (0.1 equivalents) of tri-tert-butylphosphine and 2.00 g (3 equivalents) of sodium-tert-butoxide was added into the solution, and then the reaction mixture was heated and stirred until being refluxed to proceed a reaction for 24 hours. After the reaction was completed, the solution was cooled to room temperature, and extracted with methylene chloride and distilled water. After removing the solvent, the extract was purified with column chromatography using hexane/methylene chloride (2:3) as a developing solvent and was recrystallized to give beige solid intermediate E (yield=60%).

(2) Synthesis of Compound 2-8

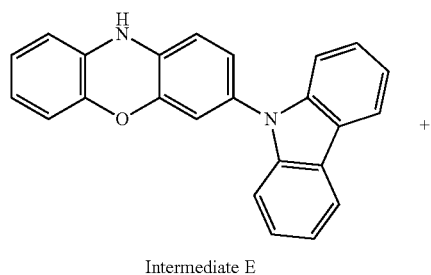

Intermediate E

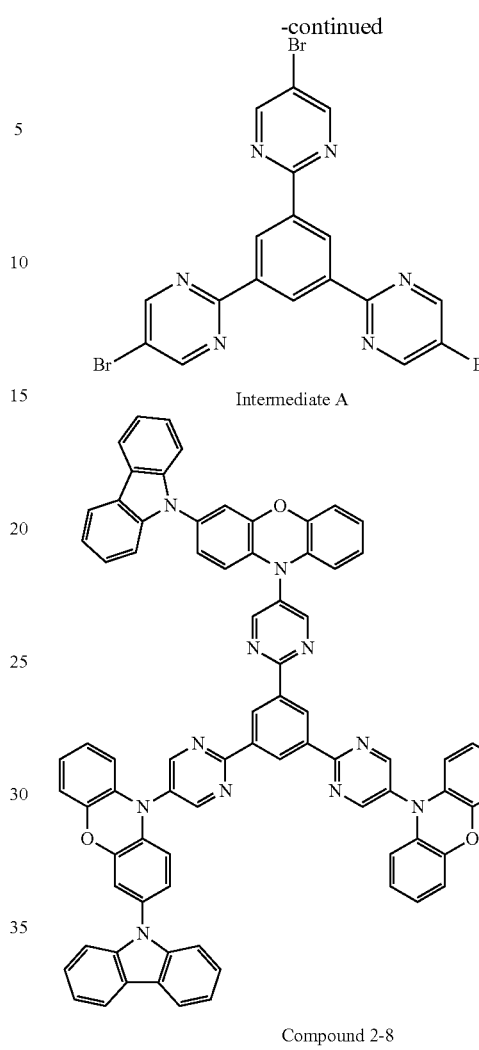

Intermediate A

Compound 2-8

1 g (1 equivalent) of Intermediate A and 2.54 g (4 equivalents) of Intermediate E was dissolved in 100 mL of toluene and stirred under nitrogen atmosphere. 0.17 g (0.1 equivalents) of Pd$_2$(dba)$_3$, 0.04 g (0.3 equivalents) of tri-tert-butylphosphine and 1.58 g (9 equivalents) of sodium tert-butoxide was added into the solution, and then the reaction mixture was heated and stirred until being refluxed for 48 hours. After the reaction was completed, the solution was cooled to room temperature, and then was washed with distilled water and acetone. After washing the extract enough, the extract was purified with column chromatography using hexane/toluene (3:1→1:1→2:1) as a developing solvent and was recrystallized to give yellow solid Compound 2-8 (yield=43%).

Synthesis Example 7: Synthesis of Compound 2-10

(1) Synthesis of Intermediate F

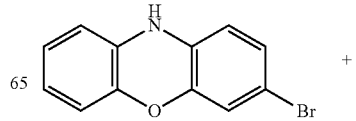

-continued

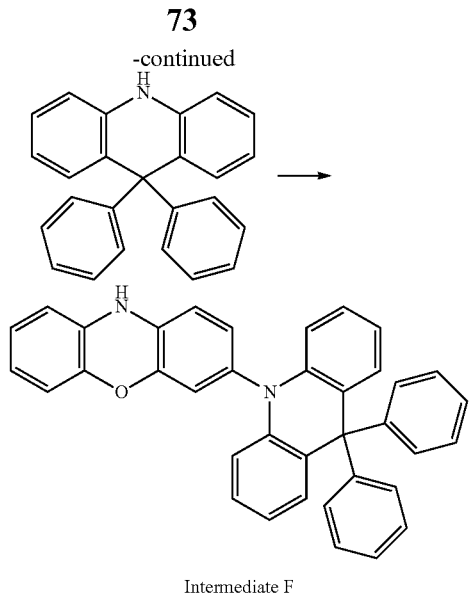

Intermediate F 2 g (1 equivalent) of 3-bromo-10H-phenoxazine and 3.05 g (1.2 equivalents) of 9,9-diphenyl-9,10-didhydroacridine was dissolved in 50 mL of toluene and stirred under nitrogen atmosphere. 0.32 g (0.05 equivalents) of $Pd_2(dba)_3$, 0.14 g (0.1 equivalents) of tri-tert-butylphosphine and 2.00 g (3 equivalents) of sodium-tert-butoxide was added into the solution, and then the reaction mixture was heated and stirred until being refluxed to proceed a reaction for 24 hours. After the reaction was completed, the solution was cooled to room temperature, and extracted with methylene chloride and distilled water. After removing the solvent, the extract was purified with column chromatography using hexane/methylene chloride (2:3) as a developing solvent and was recrystallized to give beige solid intermediate E (yield=70%).

(2) Synthesis of Compound 2-10

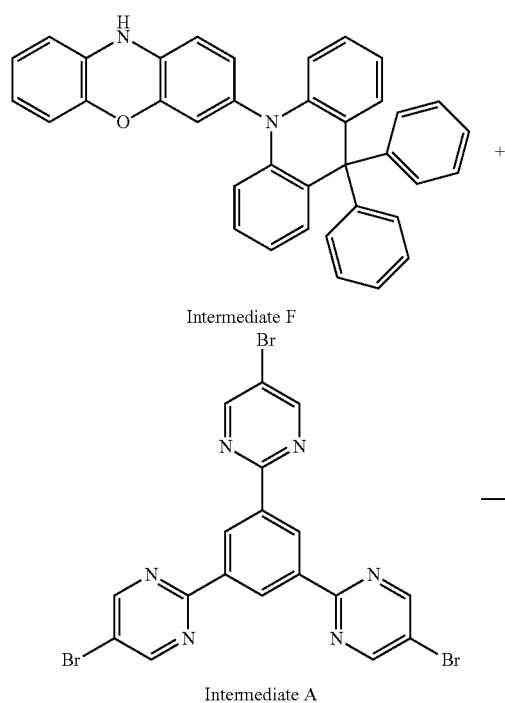

Intermediate F

Intermediate A

-continued

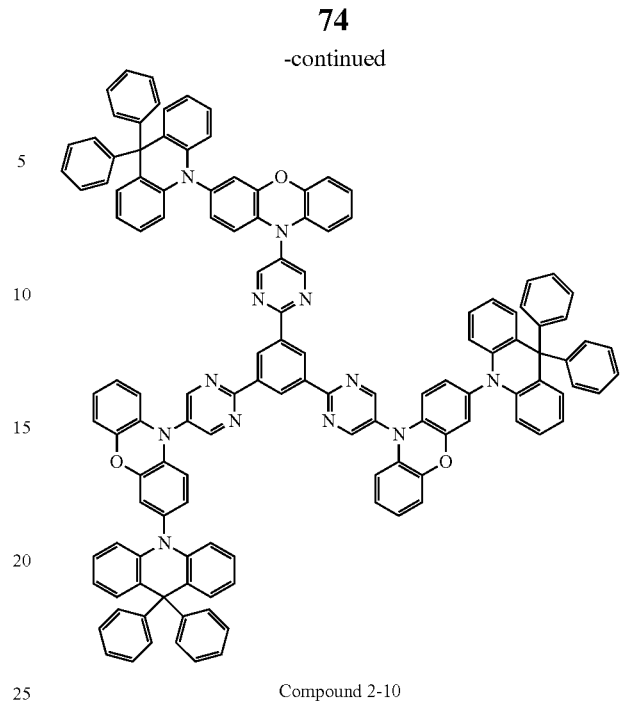

Compound 2-10

1 g (1 equivalent) of Intermediate A and 3.75 g (4 equivalents) of Intermediate F was dissolved in 100 mL of toluene and stirred under nitrogen atmosphere. 0.17 g (0.1 equivalents) of $Pd_2(dba)_3$, 0.04 g (0.3 equivalents) of tri-tert-butylphosphine and 1.58 g (9 equivalents) of sodium tert-butoxide was added into the solution, and then the reaction mixture was heated and stirred until being refluxed for 48 hours. After the reaction was completed, the solution was cooled to room temperature, and then was washed with distilled water and acetone. After washing the extract enough, the extract was purified with column chromatography using hexane/holuene (3:1→1:1→2:1) as a developing solvent and was recrystallized to give yellow solid Compound 2-10 (yield=20%).

Synthesis Example 8: Synthesis of Compound 2-11

(1) Synthesis of Intermediate G

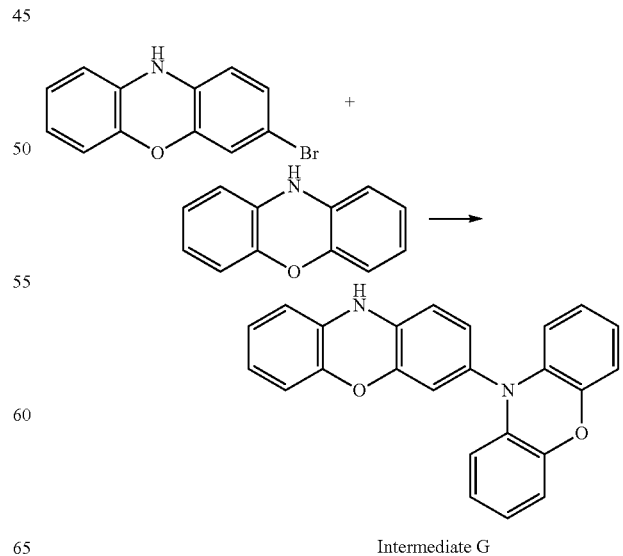

Intermediate G 2 g (1 equivalent) of 3-bromo-10OH-phenoxazine and 1.68 g (1.2 equivalents) of phenoxazine was dissolved in 50 mL of toluene and stirred under nitrogen atmosphere. 0.32 g (0.05 equivalents) of Pd$_2$(dba)$_3$, 0.14 g (0.1 equivalents) of tri-tert-butylphosphine and 2.00 g (3 equivalents) of sodium-tert-butoxide was added into the solution, and then the reaction mixture was heated and stirred until being refluxed to proceed a reaction for 24 hours. After the reaction was completed, the solution was cooled to room temperature, and extracted with methylene chloride and distilled water. After removing the solvent, the extract was purified with column chromatography using hexane/methylene chloride (2:3) as a developing solvent and was recrystallized to give beige solid intermediate G (yield=68%).

(2) Synthesis of Compound 2-11

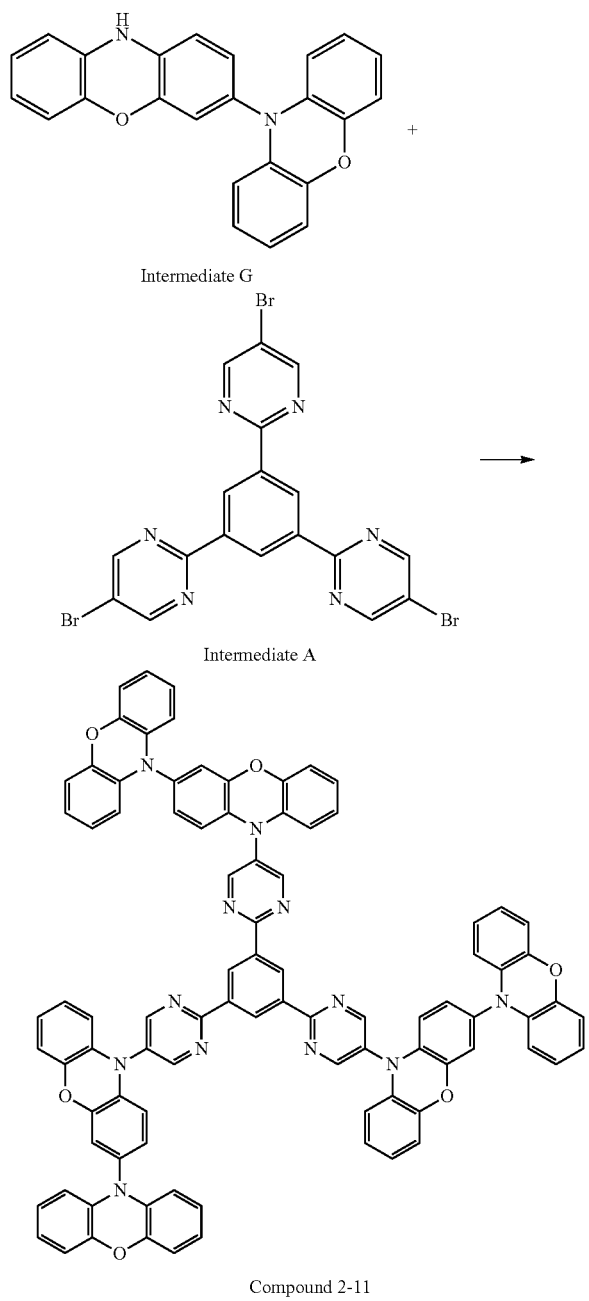

Intermediate G

Intermediate A

Compound 2-11

1 g (1 equivalent) of Intermediate A and 2.65 g (4 equivalents) of Intermediate G was dissolved in 100 mL of toluene and stirred under nitrogen atmosphere. 0.17 g (0.1 equivalents) of Pd$_2$(dba)$_3$, 0.04 g (0.3 equivalents) of tri-tert-butylphosphine and 1.58 g (9 equivalents) of sodium tert-butoxide was added into the solution, and then the reaction mixture was heated and stirred until being refluxed for 48 hours. After the reaction was completed, the solution was cooled to room temperature, and then was washed with distilled water and acetone. After washing the extract enough, the extract was purified with column chromatography using hexane/toluene (3:1→1:1→2:1) as a developing solvent and was recrystallized to give yellow solid Compound 2-11 (yield=37%).

Experimental Example 1: Measurement of Energy Level

HOMO energy levels and LUMO energy levels for the Compounds synthesized in the Synthesis Examples 1 to 8 were measured. The measurement results are indicated in the following Table 1. As indicated by Table 1, it was confirmed that each of the compounds synthesized in the Synthesis Examples 1 to 8 has a proper HOMO energy level and a LUMO energy level for a dopant of an emitting material layer in an organic light-emitting diode.

TABLE 1

Energy Level of Organic Compounds

| Compound | HOMO (eV) | LUMO (eV) | Eg (eV) |
| --- | --- | --- | --- |
| 1-1 | −5.6 | −2.8 | 2.8 |
| 1-8 | −5.5 | −2.8 | 2.7 |
| 1-10 | −5.4 | −2.7 | 2.7 |
| 2-1 | −5.5 | −2.8 | 2.7 |
| 2-7 | −5.5 | −2.8 | 2.7 |
| 2-8 | −5.4 | −2.8 | 2.6 |
| 2-10 | −5.3 | −2.8 | 2.5 |
| 2-11 | −5.3 | −2.9 | 2.4 |

HOMO: Film (100 nm/ITO), by AC3;
LUMO: Calculated from Film Absorbance edge;
Eg: LUMO − HOMO Example 1: Manufacture of Organic Light-Emitting Diode (OLED)

An organic light-emitting diode was manufacture using Compound 1-1 synthesized in the Synthesis Example 1 as a dopant in an emitting material layer (EML). A glass substrate was washed by UV-Ozone treatment before using, and was transferred to a vacuum chamber for depositing emission layer. Subsequently, an anode, an emission layer and a cathode were deposited under 10$^{-6}$ Torr as the following order: an anode (ITO); a hole injection layer (HIL) (HAT-CN; 7 nm); a hole transport layer (HTL) (NPB, 55 nm); a electron blocking layer (EBL) (mCBP; 10 nm); an emitting material layer (EML) (4-(3-tirphenyl-2-yl)phenyl)dibenzo[b,d]thiophene (host): Compound 1 (dopant)=70:30 by weight; 35 nm); a hole blocking layer (HBL) (B3PYMPM; 10 nm); an electron transport layer (ETL) (TPBi; 20 nm); an electron injection layer (EIL) (LiF; 35 nm); and a cathode (Al).

And then, capping layer (CPL) was deposited over the cathode and the device was encapsulated by glass. After deposition of emissive layer and the cathode, the OLED was transferred from the deposition chamber to a dry box for film formation, followed by encapsulation using UV-curable epoxy and moisture getter. The manufacture organic light-emitting diode had an emission area of 9 mm².

Examples 2 to 8: Manufacture of OLED

An organic light-emitting diode was manufactured as the same process and the same materials as in Example 1, except that Compound 1-8 (Example 2) synthesized in the Synthesis Example 2, Compound 1-10 (Example 3) synthesized in the Synthesis Example 3, Compound 2-1 (Example 4) synthesized in the Synthesis Example 4, Compound 2-7 (Example 5) synthesized in the Synthesis Example 5, Compound 2-8 (Example 6) synthesized in the Synthesis Example 6, Compound 2-10 (Example 7) synthesized in the Synthesis Example 7 and Compound 2-11 (Example 8) synthesized in the Synthesis Example 8 as the dopant in the EML instead of the Compound 1.

Comparative Example: Manufacture of OLED

An organic light-emitting diode was manufactured as the same process and the same materials as in Example 1, except that following Reference Compound as the fluorescent dopant in the EML instead of the Compound 1.

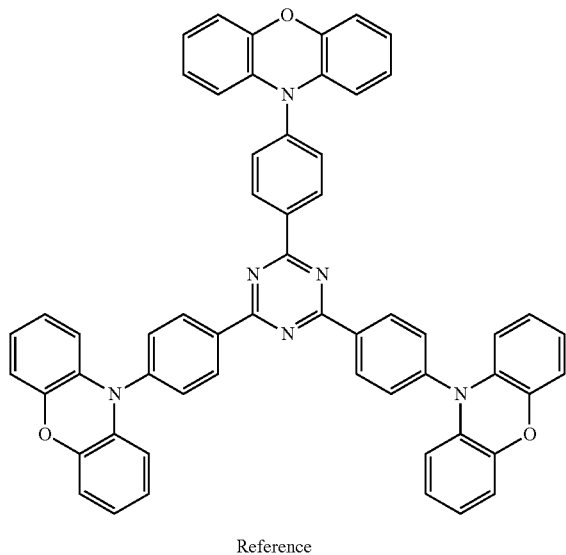 [SMILES: c1ccc2c(c1)Oc1ccccc1N2c1ccc(-c2nc(-c3ccc(N4c5ccccc5Oc5ccccc54)cc3)nc(-c3ccc(N4c5ccccc5Oc5ccccc54)cc3)n2)cc1]

Reference

Experimental Example 2: Measurement of Luminous Properties of OLED

Each of the organic light-emitting diode with manufactured by Examples 1 to 8 and Comparative Example was connected to an external power source, and luminous properties for all the diodes were evaluated using a constant current source (KEITHLEY) and a photometer PR650 at room temperature. In particular, driving voltage (V), current efficiency (Cd/A), power efficiency (lm/W), external quantum efficiency (EQE; %), color coordinates and maximum electroluminescent wavelength (EL $\lambda_{max}$; nm) at a current density of 10 mA/cm² of the light-emitting diodes of Examples 1 to 8 and Comparative Example were measured. The measurement results are indicated in the following Table 2.

TABLE 2

Luminous Properties of OLED

| Sample | V | cd/A | lm/W | EQE (%) | $\lambda_{max}$ (nm) | CIE |
|---|---|---|---|---|---|---|
| Comparative Example 1 | 3.82 | 45.69 | 37.57 | 14.88 | 568 | (0.434, 0.535) |
| Example 1 | 3.97 | 54.63 | 43.18 | 17.46 | 526 | (0.320, 0.563) |
| Example 2 | 3.53 | 54.88 | 48.91 | 17.18 | 536 | (0.357, 0.569) |
| Example 3 | 4.20 | 48.30 | 36.10 | 15.00 | 538 | (0.367, 0.568) |
| Example 4 | 3.87 | 58.99 | 47.89 | 18.23 | 536 | (0.341, 0.569) |
| Example 5 | 3.74 | 55.12 | 46.33 | 17.25 | 538 | (0.356, 0.567) |
| Example 6 | 3.84 | 50.79 | 41.57 | 15.93 | 540 | (0.369, 0.563) |
| Example 7 | 3.56 | 46.85 | 41.33 | 13.75 | 544 | (0.399, 0.563) |
| Example 8 | 3.56 | 34.15 | 30.16 | 9.83 | 546 | (0.427, 0.554) |

As indicated in Table 2, compared to the OLED using Reference Compound as the dopant in the EML according to the Comparative Example, the OLED using the organic compounds as the dopant in the EML according to the Examples 1 to 8 lowered driving voltage maximally by 6.8%, and enhanced current efficiency maximally by 29.1%, power efficiency maximally by 30.2% and EQE maximally by 22.5%. Particularly, Compared to the OLED using the Reference Compound as the dopant, the OLED using the organic compounds as the dopant emitted green light with deeper color sensitivity.

From these results, it was confirmed that an organic light-emitting diode and an organic light-emitting device such as an organic light-emitting display device and an organic light-emitting illumination device using the organic compounds can enhance luminous efficiency and implement hyper-fluorescence with high color purity.

Examples 9 to 11: Manufacture of OLED

An organic light-emitting diode was manufactured as the same process and the same materials as in Example 1, except that Compound 1-1 doped 10% by weight (Example 9), Compound 1-1 doped 20% by weight (Example 10) and Compound 1-1 doped 50% by weigh as the dopant in the EML in place the compound 1-1 doped 30% by weight.

Experimental Example 3: Measurement of Luminous Properties of OLED

Luminous properties for each of the organic light-emitting diode with manufactured by Examples 9 to 11 were evaluated as the same process as Experimental Example 2. The measurement results are indicated in the following Table 3:

TABLE 3

Luminous Properties of OLED

| Sample | V | cd/A | lm/W | EQE (%) | $\lambda_{max}$ (nm) | CIE |
|---|---|---|---|---|---|---|
| Comparative Example | 3.82 | 45.69 | 37.57 | 14.88 | 568 | (0.434, 0.535) |
| Example 1 | 3.97 | 54.63 | 43.18 | 17.46 | 526 | (0.320, 0.563) |
| Example 9 | 3.86 | 50.02 | 40.68 | 16.24 | 520 | (0.309, 0.559) |
| Example 10 | 3.93 | 52.87 | 42.29 | 17.05 | 522 | (0.311, 0.560) |
| Example 11 | 3.82 | 52.93 | 43.55 | 16.68 | 526 | (0.327, 0.569) |

Comparative Example and Example 1: doping concentration 30% by weight;
Example 9: doping concentration 10% by weight;
Example 10: doping concentration 20% by weight;
Example 11: doping concentration 50% by weight As indicated in Table 3, compared to the OLED using Reference Compound as the dopant in the EML according to the Comparative Example, each of the OLEDs using the organic compound as the dopant in the EML according to Examples 9-11 enhances current efficiency, power efficiency and EQE in spite of changing doping concentration of 10-50% by weight. In particular, the OLEDs using the organic compound doped 20-50% by weight as the dopant in the EML in accordance with Example 1 and Examples 10-11 exhibited relatively enhanced luminous efficiencies. While the EL $\lambda_{max}$ was moved toward somewhat longer wavelengths as the doping concentration increases, the OLEDs still emitted green light with deeper color sensitivity compared to the OLED in the Comparative Example.

While the present disclosure has been described with reference to exemplary embodiments and examples, these embodiments and examples are not intended to limit the scope of the present disclosure. Rather, it will be apparent to those skilled in the art that various modifications and variations can be made in the present disclosure without departing from the spirit or scope of the invention. Thus, it is intended that the present disclosure cover the modifications and variations of the present disclosure provided they come within the scope of the appended claims and their equivalents.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An organic compound represented by the following Chemical Formula 4:

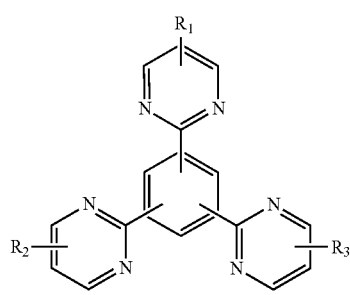

Chemical Formula 4 wherein each of $R_1$ to $R_3$ is independently the following Chemical Formula 6 or 8,

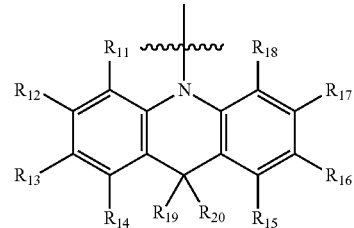

Chemical Formula 6 wherein each of $R_{11}$ to $R_{18}$ is independently hydrogen, a silyl group, a $C_1$-$C_{20}$ alkyl group, a $C_1$-$C_{20}$ alkoxy group, a $C_1$-$C_{20}$ alkyl-amino group, a $C_5$-$C_{30}$ aryl group, a $C_4$-$C_{30}$ heteroaryl group, a $C_5$-$C_{30}$ aryloxyl group, a $C_4$-$C_{30}$ heteroaryloxyl group, a $C_5$-$C_{30}$ arylamino group or a $C_4$-$C_{30}$ heteroaryl amino group, or two adjacent groups among Ru to $R_{18}$ form a $C_4$-$C_{30}$ fused aromatic or heteroaromatic ring unsubstituted or substituted with a $C_4$-$C_{30}$ aromatic or heteroaromatic group,; each of $R_{19}$ and $R_{20}$ is independently hydrogen, a $C_1$-$C_{20}$ alkyl group, a $C_1$-$C_{20}$ alkoxy group, a $C_1$-$C_{20}$ alkylamino group, a $C_5$-$C_{30}$ aryl group, a $C_4$-$C_{30}$ heteroaryl group, a $C_5$-$C_{30}$ aryloxyl group, a $C_4$-$C_{30}$ heteroaryloxyl group, a $C_5$-$C_{30}$ arylamino group or a $C_4$-$C_{30}$ heteroaryl amino group, or $R_{19}$ and $R_{20}$ form a $C_4$-$C_{30}$ Spiro aromatic or heteroaromatic ring, wherein at least one of $R_{11}$ to $R_{18}$ is a silyl group, a $C_1$-$C_{20}$ alkyl group, a $C_1$-$C_{20}$ alkoxy group, a $C_1$-$C_{20}$ alkyl-amino group, a $C_5$-$C_{30}$ aryl group, a $C_4$-$C_{30}$ heteroaryl group, a $C_5$-$C_{30}$ aryloxyl group, a $C_4$-$C_{30}$ heteroaryloxyl group, a $C_5$-$C_{30}$ arylamino group or a $C_4$-$C_{30}$ heteroaryl amino group, or two adjacent groups among $R_{11}$ to $R_{18}$ form a $C_4$-$C_{30}$ fused aromatic or heteroaromatic ring unsubstituted or substituted with a $C_4$-$C_{30}$ aromatic or heteroaromatic group when each of $R_{19}$ and $R_{20}$ is independently the $C_1$-$C_{20}$ alkyl group,

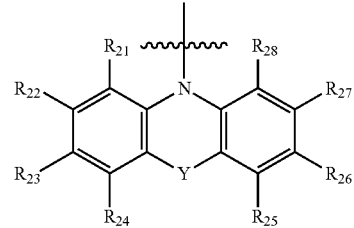

Chemical Formula 8 wherein each of $R_{21}$ to $R_{28}$ is independently hydrogen, a silyl group, a $C_1$-$C_{20}$ alkyl group, a $C_1$-$C_{20}$ alkoxy group, a $C_1$-$C_{20}$ alkylamino group, a $C_5$-$C_{30}$ aryl group, a $C_4$-$C_{30}$ heteroaryl group, a $C_5$-$C_{30}$ aryloxyl group, a $C_4$-$C_{30}$ heteroaryloxyl group, a $C_5$-$C_{30}$ arylamino group or a $C_4$-$C_{30}$ heteroaryl amino group, or two adjacent groups among $R_{21}$ to $R_{28}$ form a $C_4$-$C_{30}$ fused aromatic or heteroaromatic ring unsubstituted or substituted with a $C_4$-$C_{30}$ aromatic or heteroaromatic group; Y is $NR_{29}$, O or S, wherein $R_{29}$ is hydrogen, a silyl group, a $C_1$-$C_{20}$ alkyl group, a $C_1$-$C_{20}$ alkoxy group, a $C_1$-$C_{20}$ alkylamino group, a $C_5$-$C_{30}$ aryl group, a $C_4$-$C_{30}$ heteroaryl group, a $C_5$-$C_{30}$ aryloxyl group, a $C_4$-$C_{30}$ heteroaryloxyl group, a $C_5$-$C_{30}$ arylamino group or a $C_4$-$C_{30}$ heteroaryl amino group, wherein at least one of $R_{21}$ to $R_{28}$ is a silyl group, a $C_1$-$C_{20}$ alkyl group, a $C_1$-$C_{20}$ alkoxy group, a $C_1$-$C_{20}$ alkylamino group, a $C_5$-$C_{30}$ aryl group, a $C_4$-$C_{30}$ heteroaryl group, a $C_5$-$C_{30}$ aryloxyl group, a $C_4$-$C_{30}$ heteroaryloxyl group, a $C_5$-$C_{30}$ arylamino group or a $C_4$-$C_{30}$ heteroaryl amino group, or two adjacent groups among $R_{21}$ to $R_{28}$ form a $C_4$-$C_{30}$ fused aromatic or heteroaromatic ring unsubstituted or substituted with a $C_4$-$C_{30}$ aromatic or heteroaromatic group when Y is O or S.

2. The organic compound of claim 1, wherein the organic compound has the following structure of Chemical Formula 5:

Chemical Formula 5

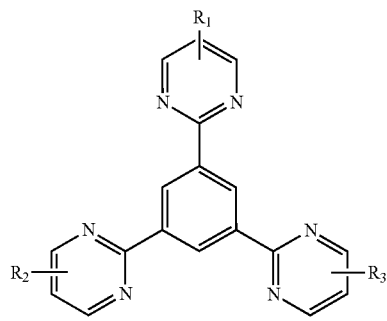

wherein each of $R_1$ to $R_3$ is independently the same as defined in Chemical Formula 1.

3. The organic compound of claim 1, wherein the organic compound has any one of the following structures of Chemical Formula 7:

Compound 1-7

Compound 1-8

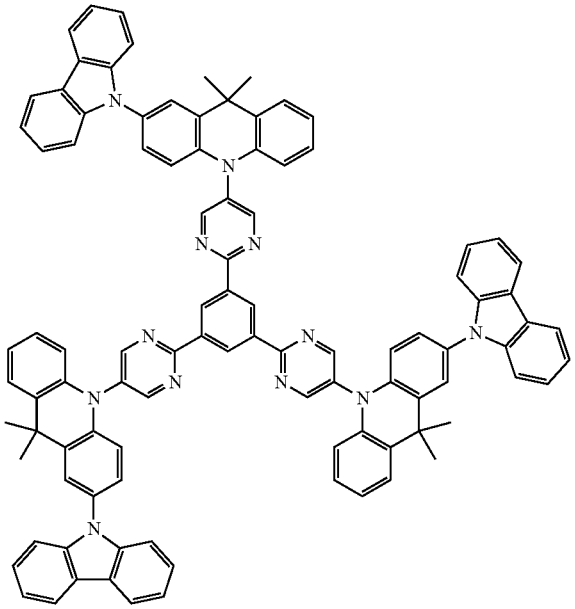

Compound 1-9

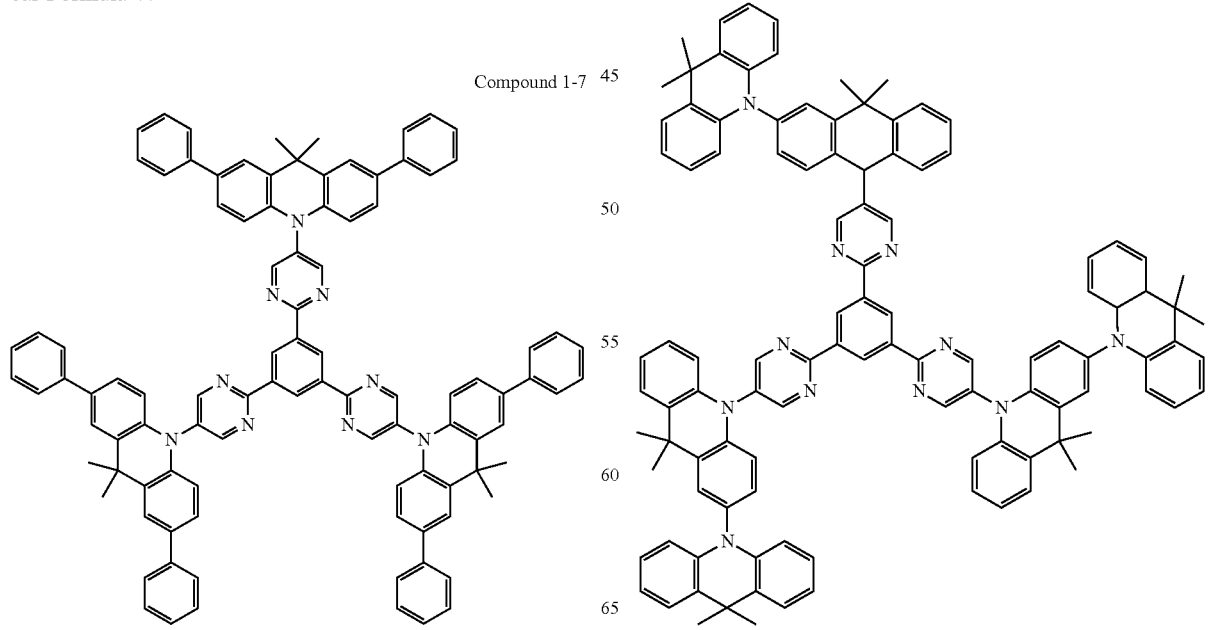

Compound 1-10
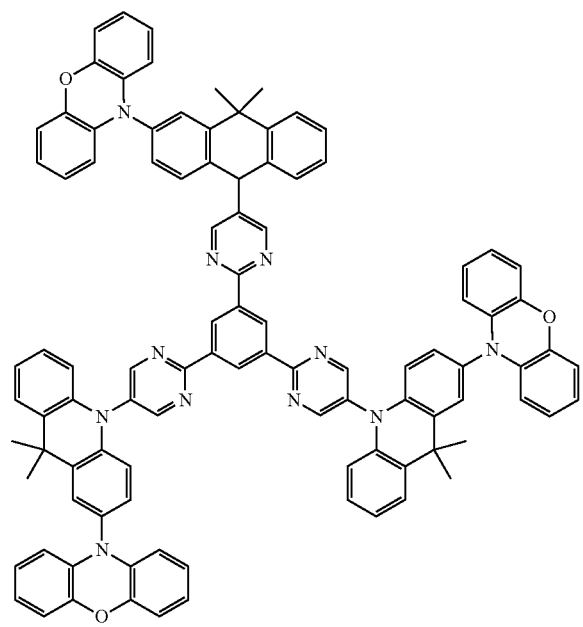
Compound 1-11
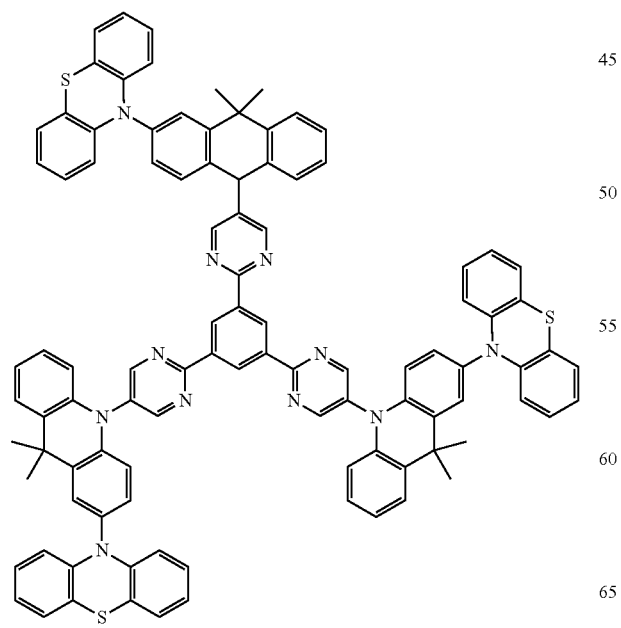
Compound 1-12
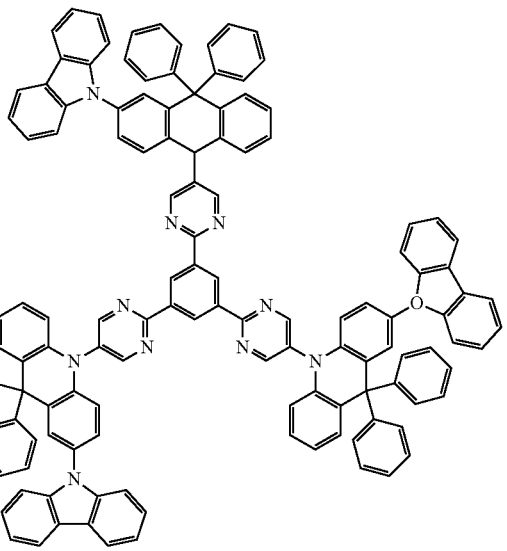
Compound 1-13
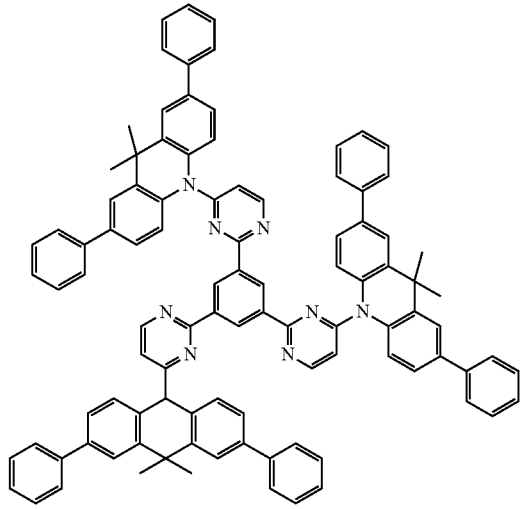

Compound 1-14
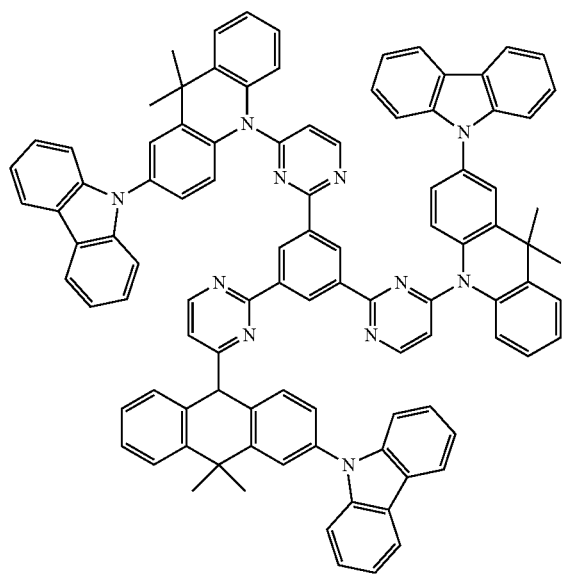
Compound 1-15
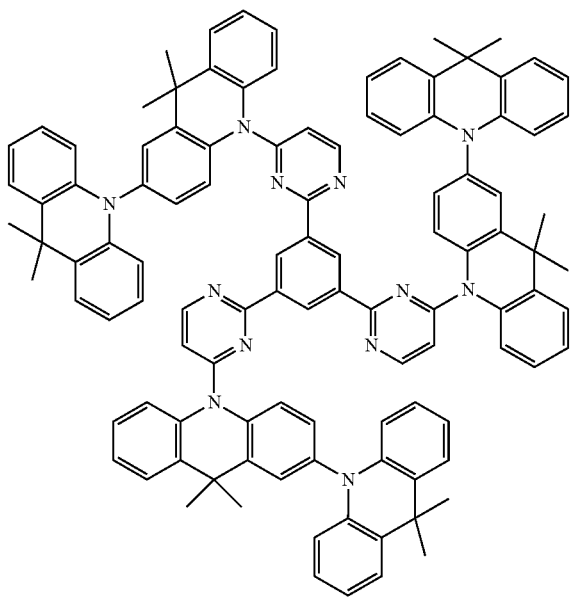
Compound 1-16
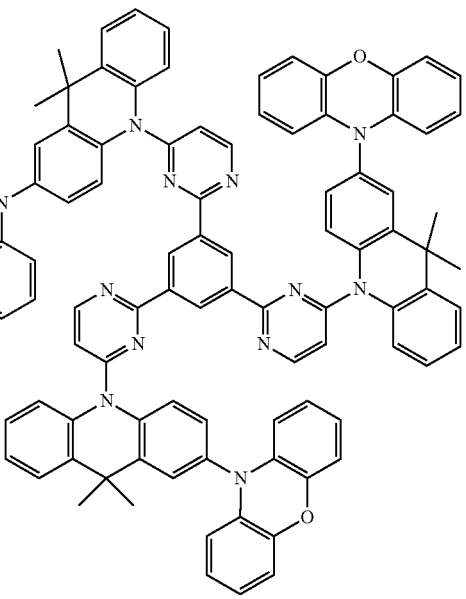
Compound 1-17
4. The organic compound of claim 1, wherein the organic compound has any one of the following structures of Chemical Formula 9:

Chemical Formula 9
Compound 2-5
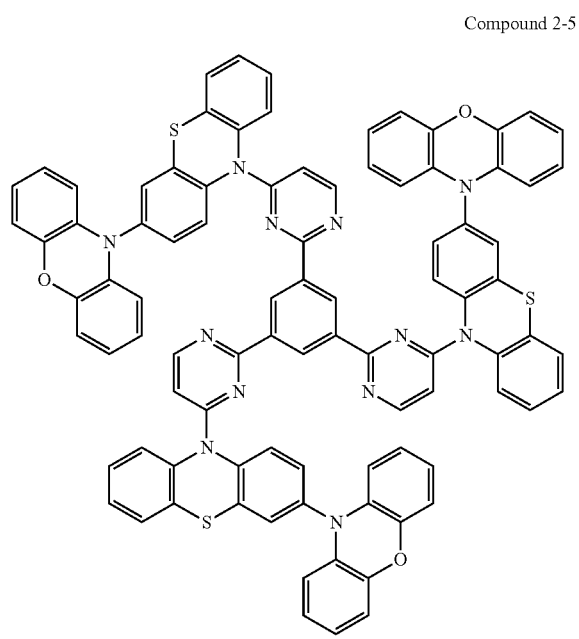
Compound 2-7
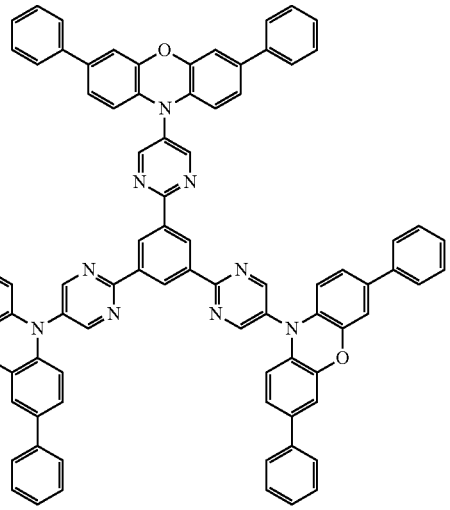
Compound 2-6
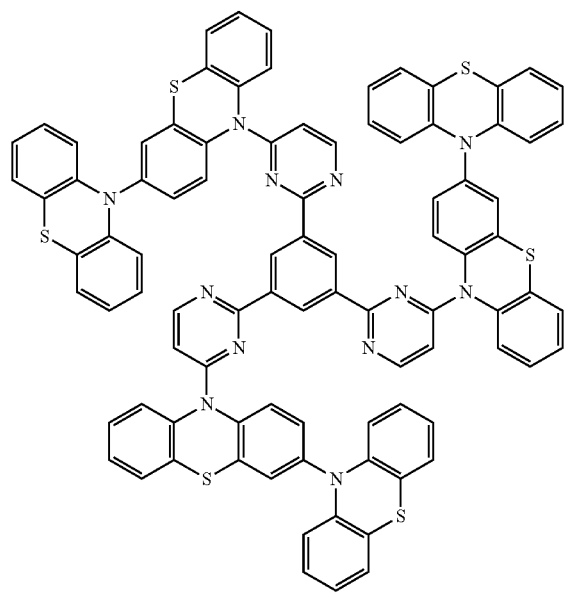
Compound 2-8
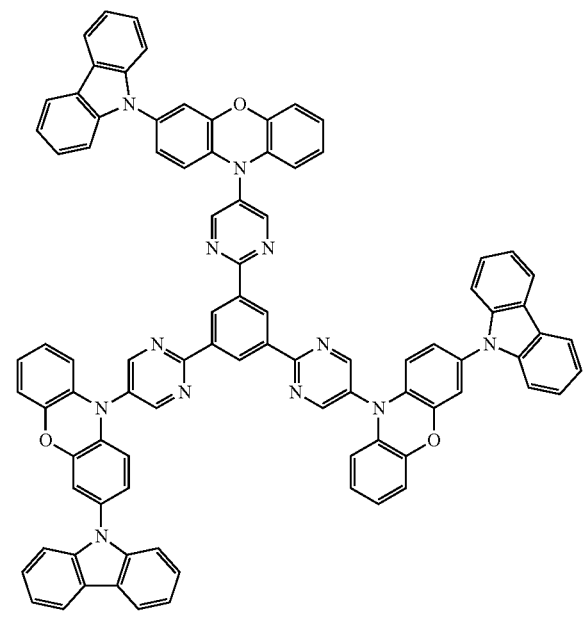

Compound 2-9
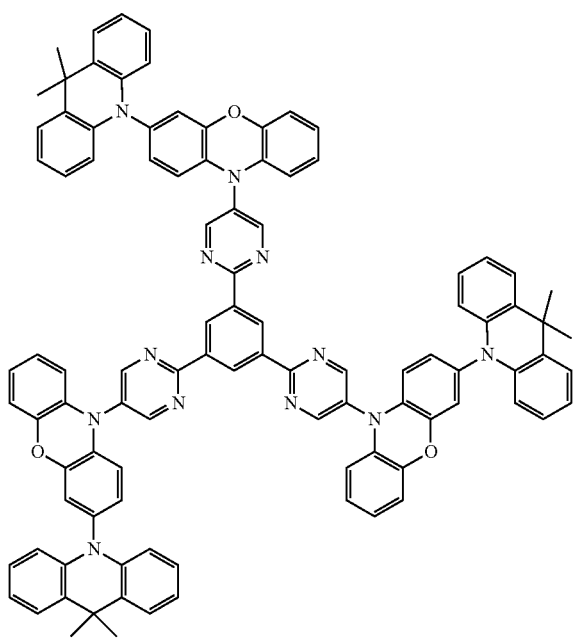
Compound 2-10
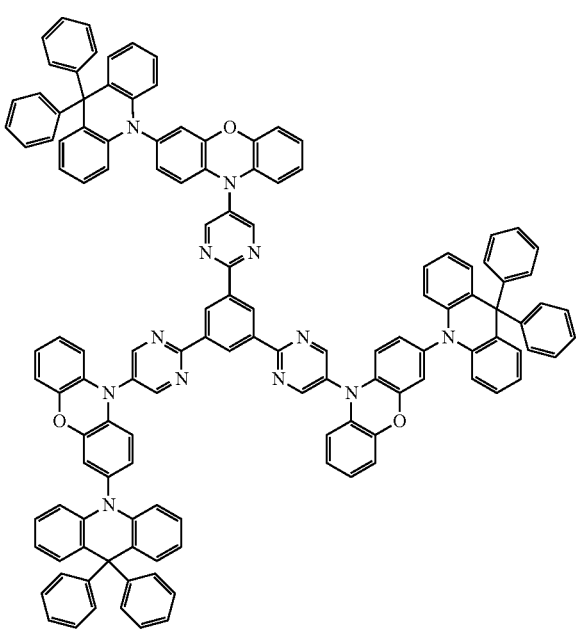
Compound 2-11
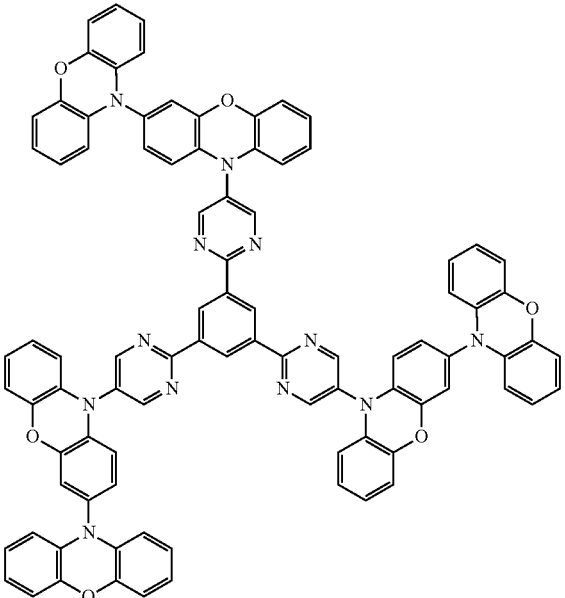
Compound 2-12
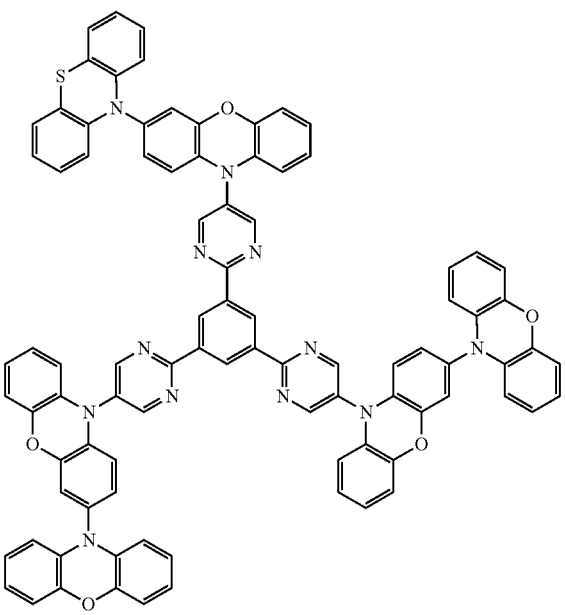

Compound 2-13
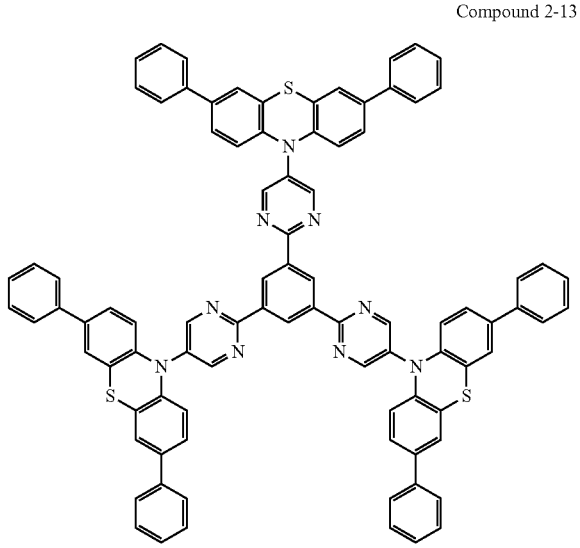
Compound 2-14
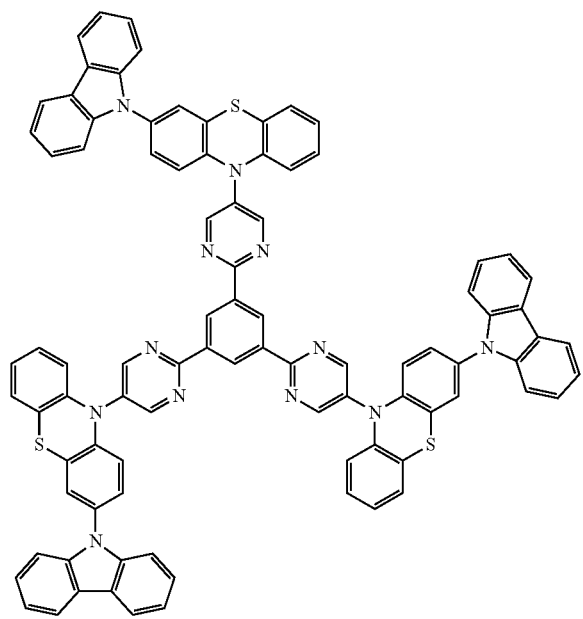
Compound 2-15
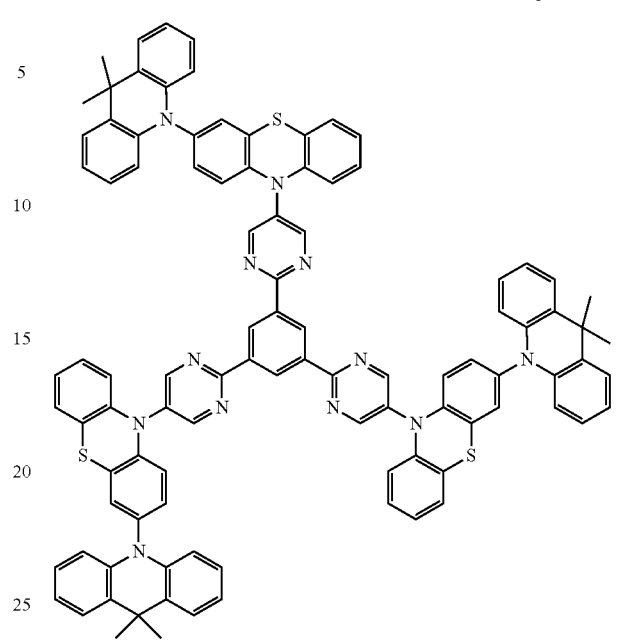
Compound 2-16
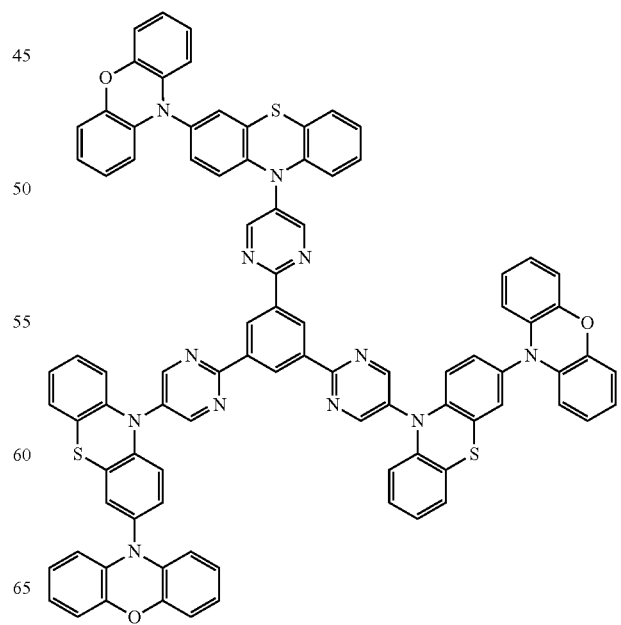

Compound 2-17
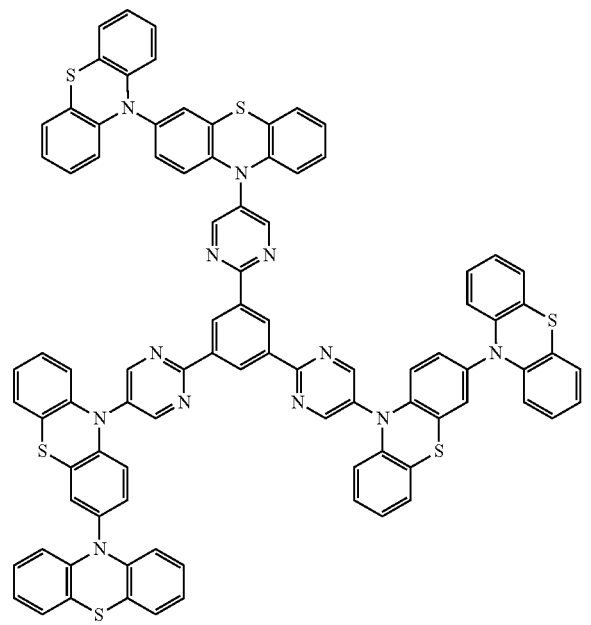
Compound 2-19
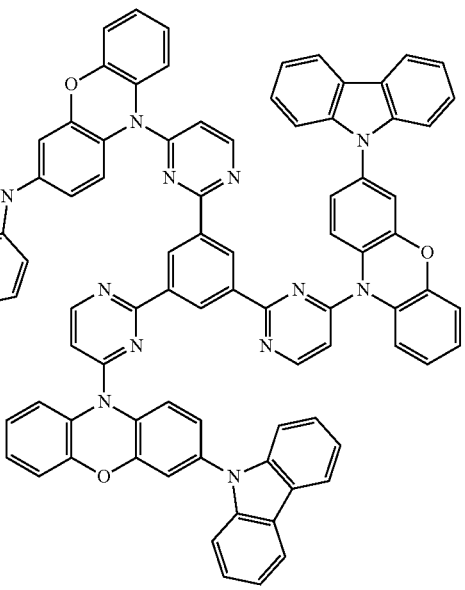
Compound 2-18
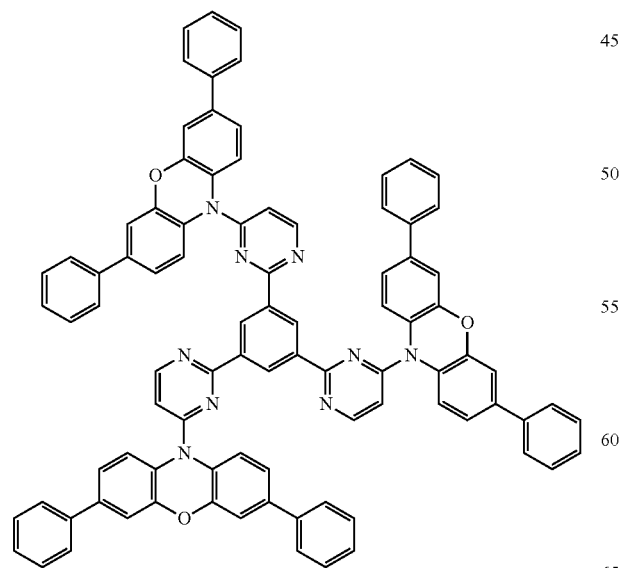
Compound 2-20

Compound 2-21
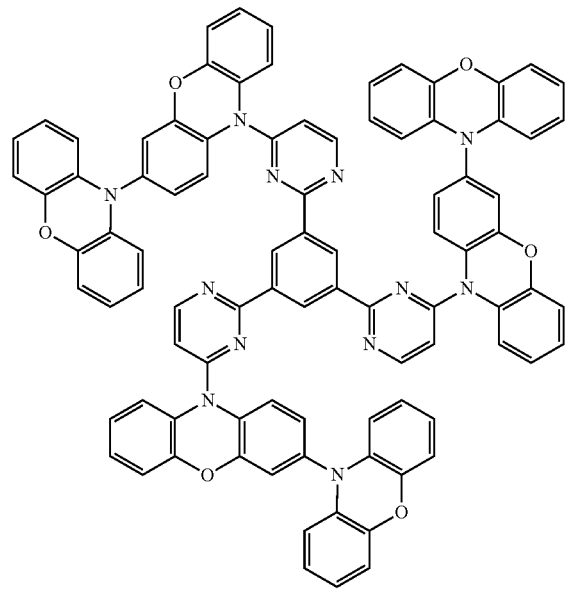
Compound 2-23
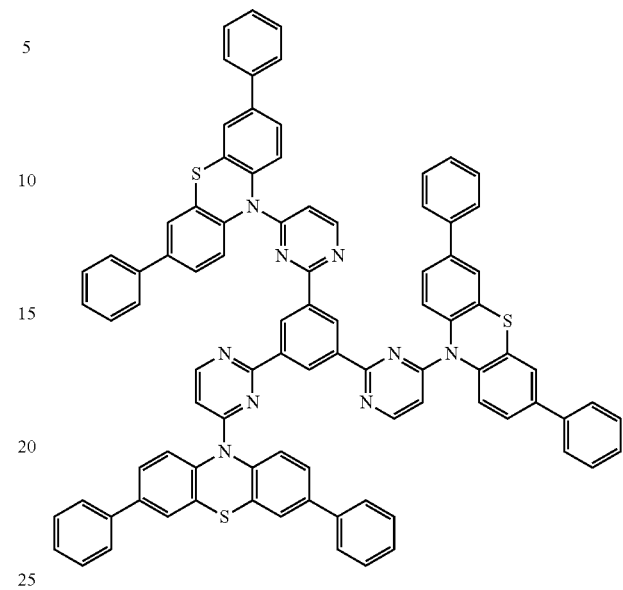
Compound 2-22
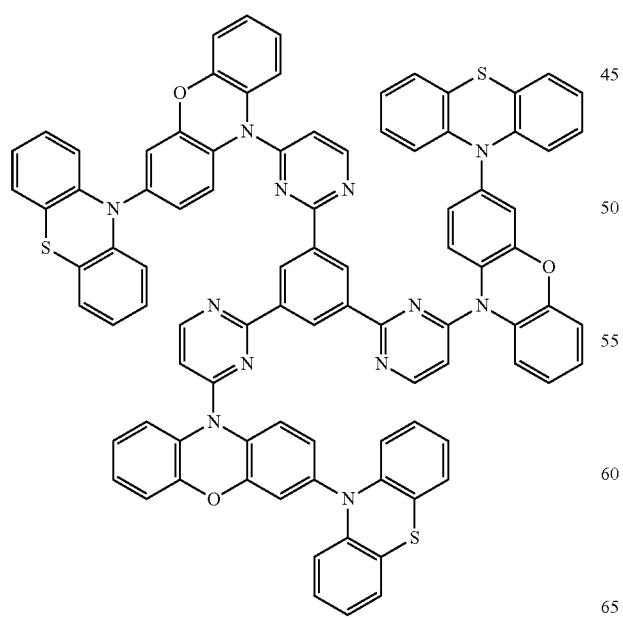
Compound 2-24
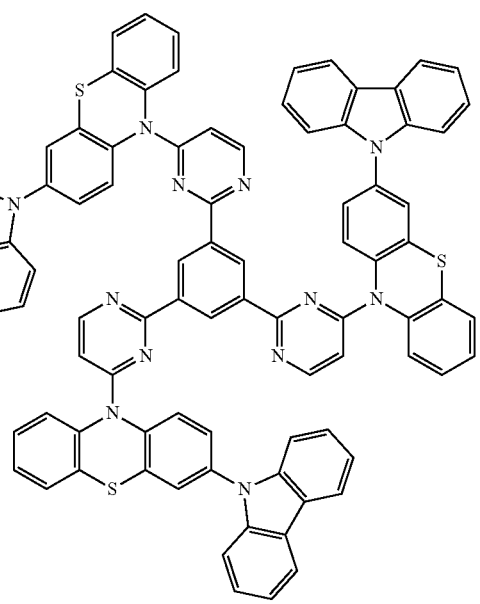

Compound 2-25
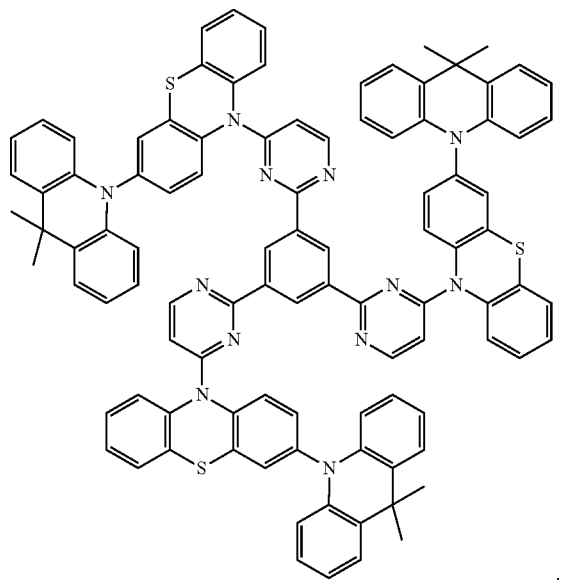
Compound 3-3
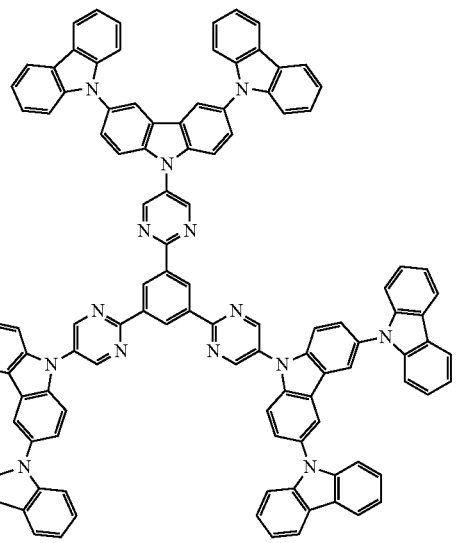
5. An organic compound selected from any one of the following structures of Chemical Formula 11:
Chemical Formula 11
Compound 3-2
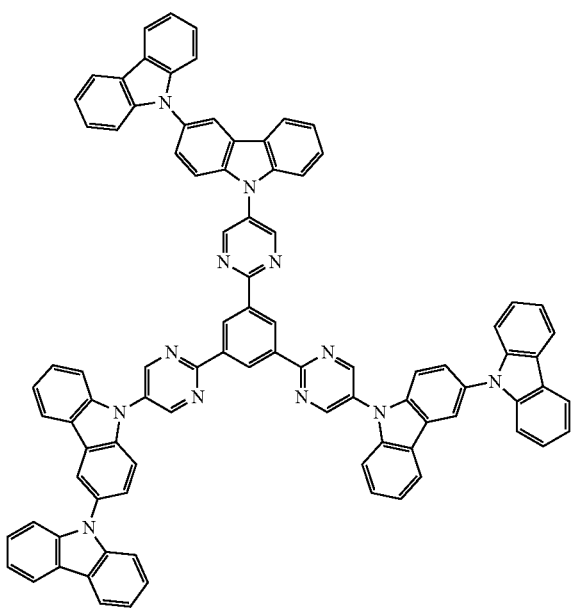
Compound 3-4
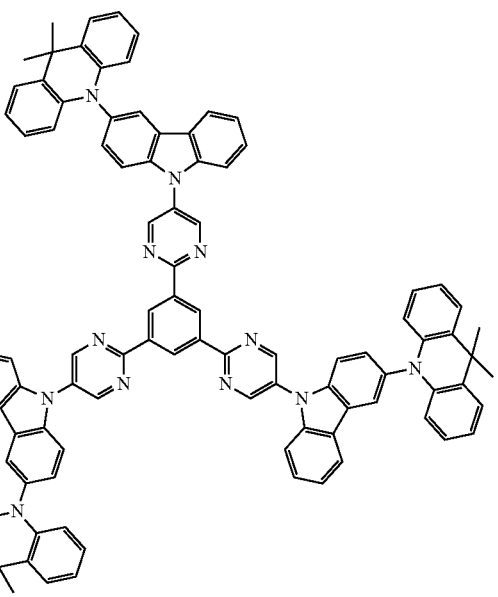

Compound 3-5
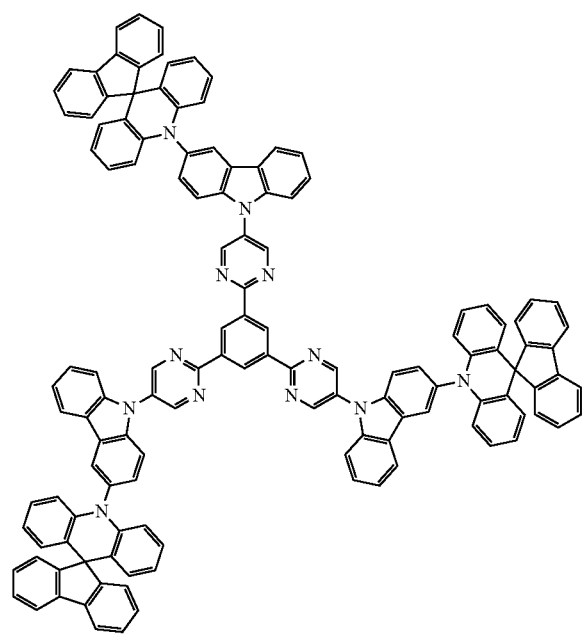
Compound 3-7
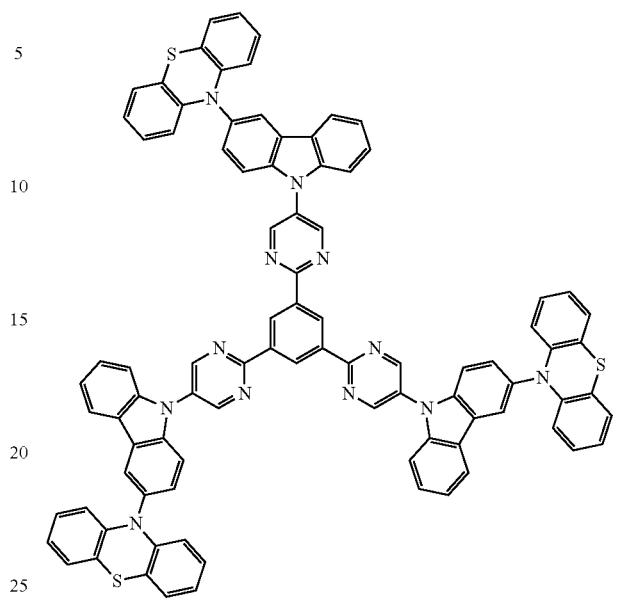
Compound 3-6
Compound 3-8
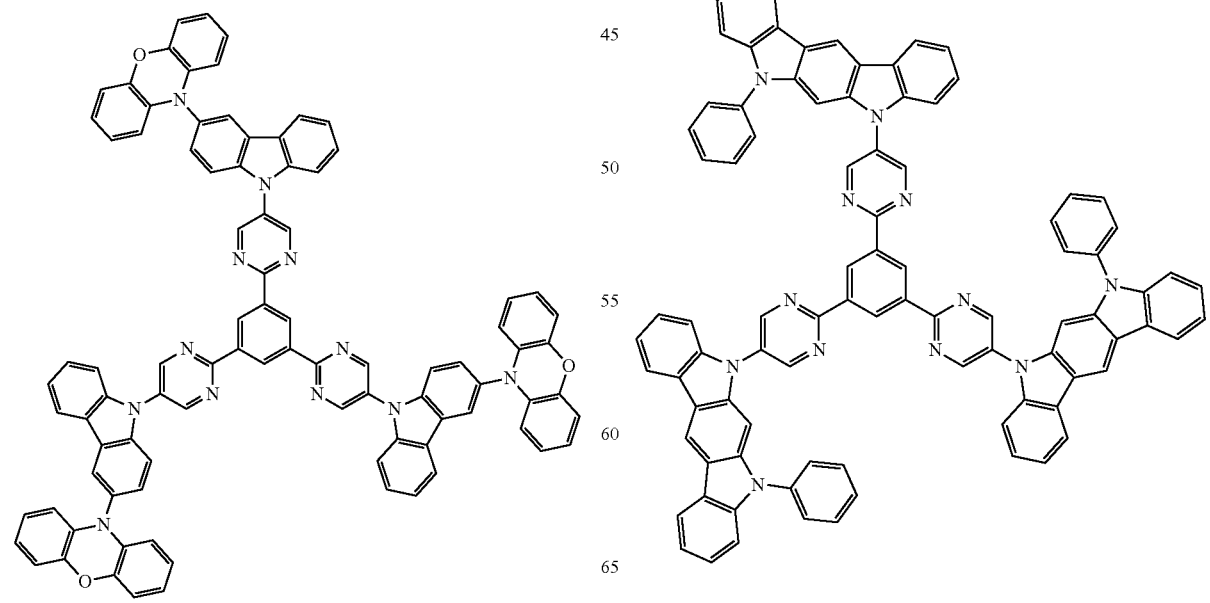

Compound 3-9
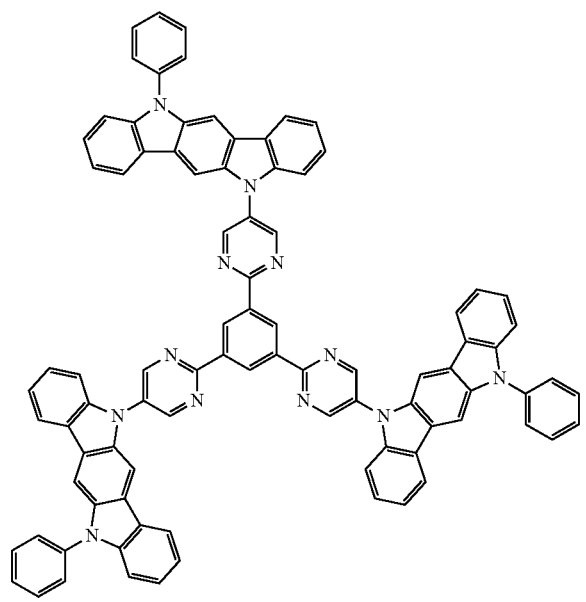
Compound 3-11
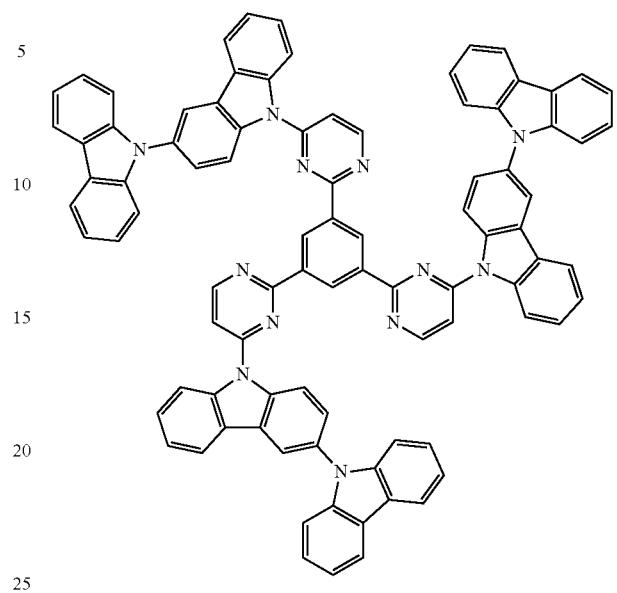
Compound 3-10
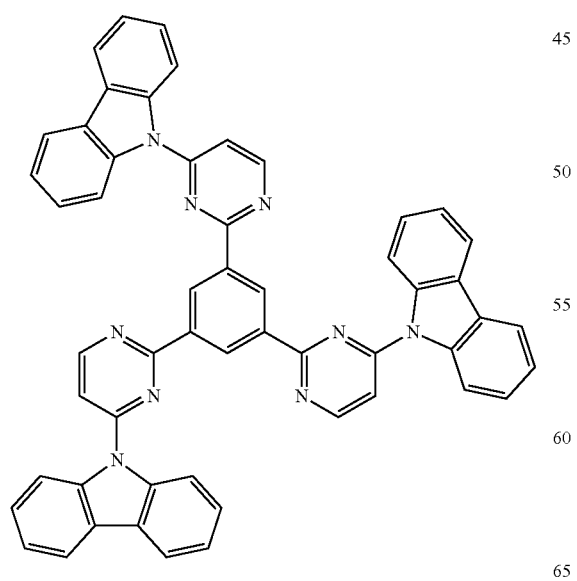
Compound 3-12
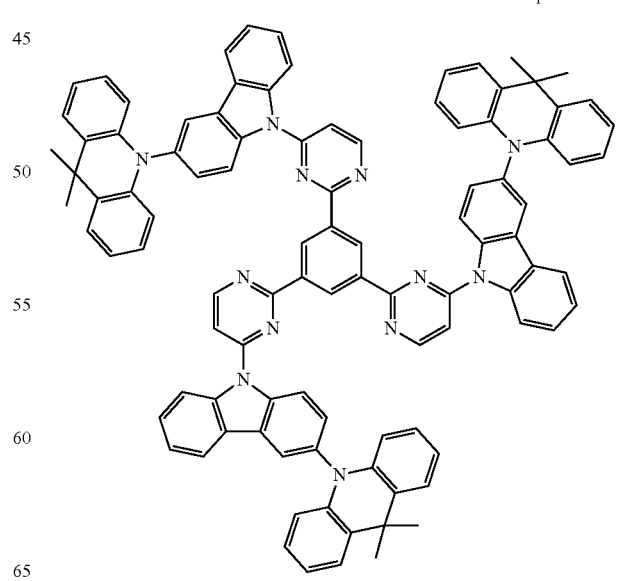

Compound 3-13
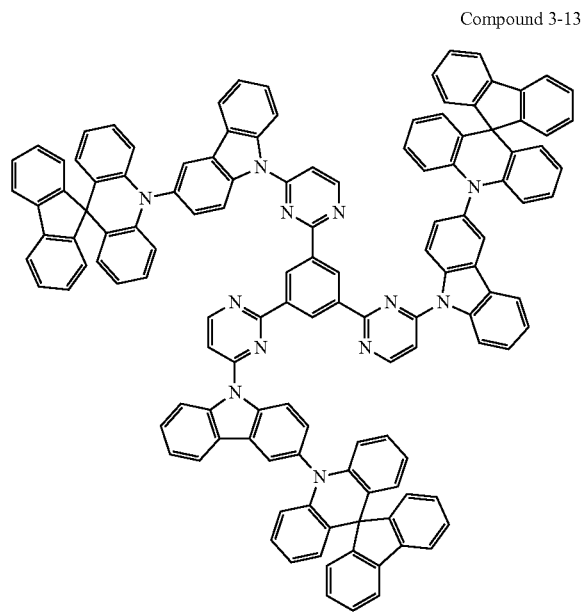
Compound 3-15
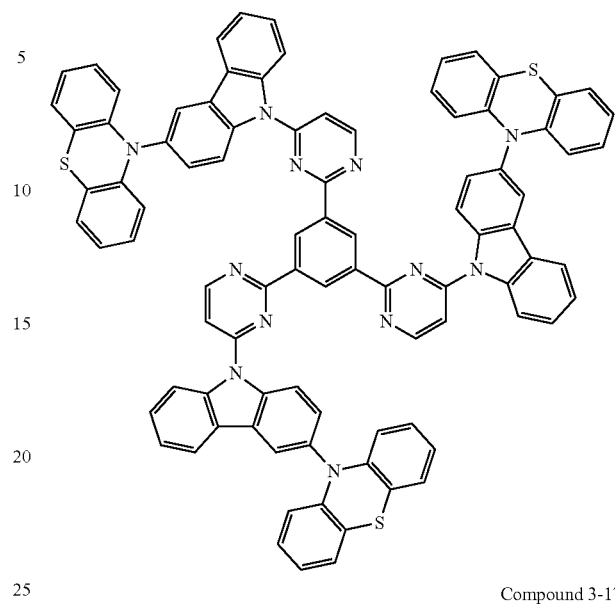
Compound 3-17
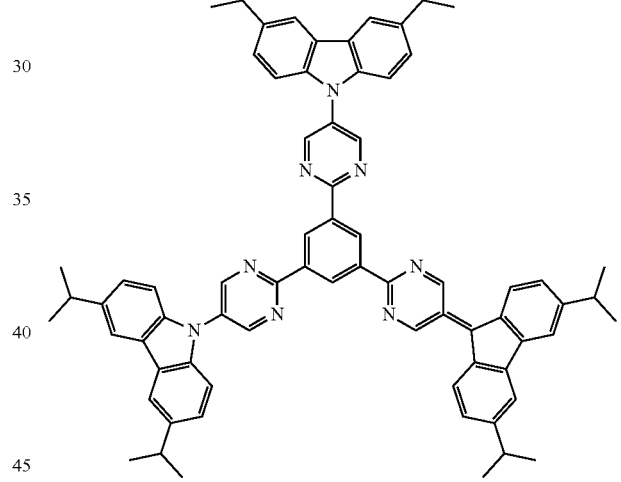
Compound 3-14
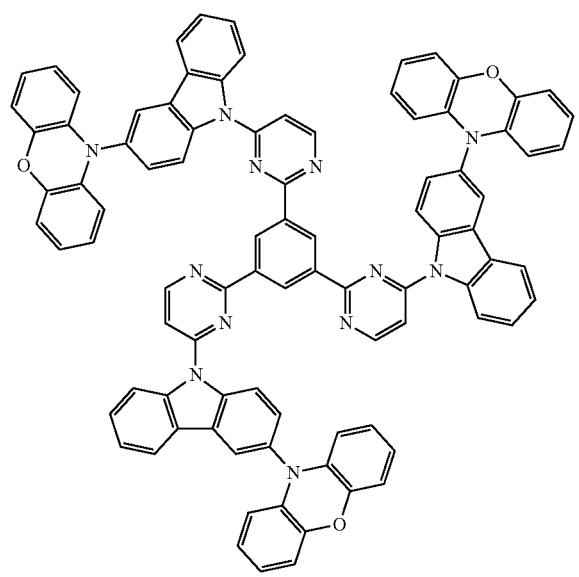
Compound 3-18
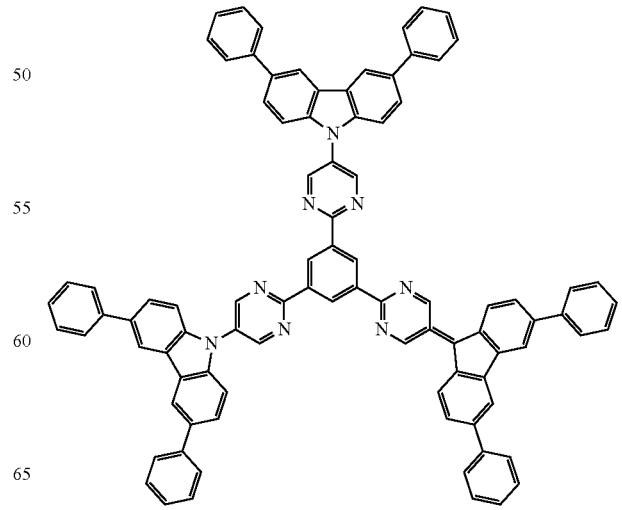

Compound 3-19

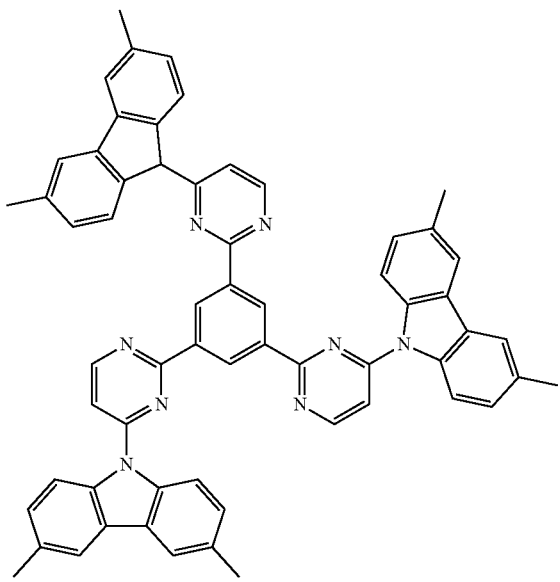

Compound 2-20

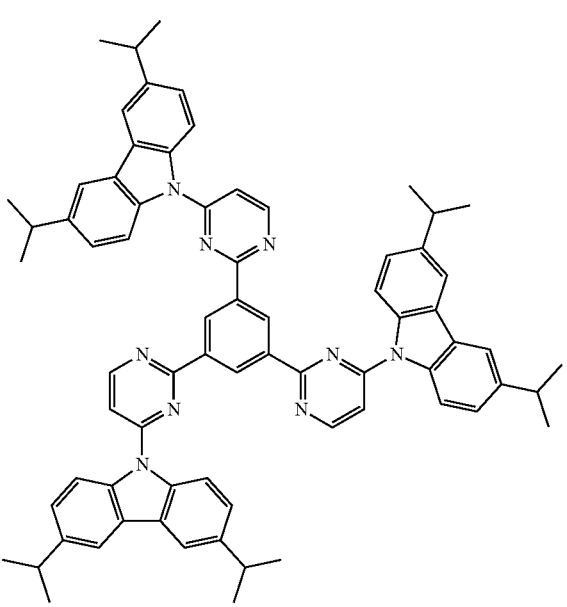

Compound 2-21

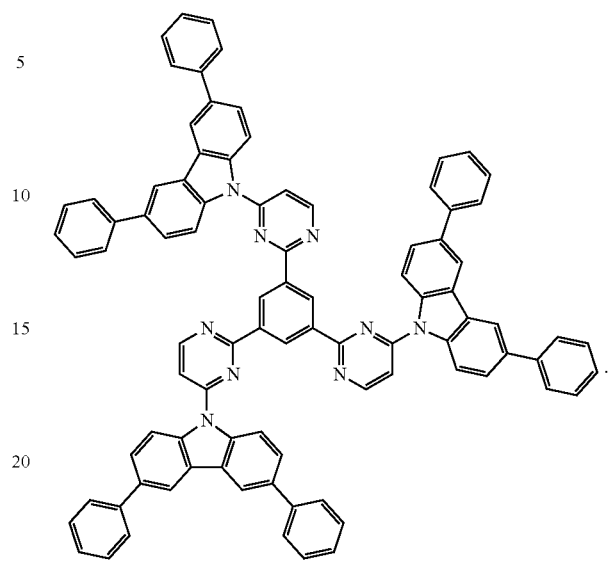

6. An organic light-emitting diode, comprising:
a first electrode;
a second electrode facing the first electrode; and
an emitting material layer between the first and second electrodes,
wherein the emitting material layer comprises an organic compound according to claim 1.

7. The organic light-emitting diode of claim 6, wherein the emitting material layer further includes a first host, wherein the organic compound is used as a first dopant.

8. The organic light-emitting diode of claim 7, wherein an energy bandgap between a Highest Occupied Molecular Orbital energy level of the first host and a Highest Occupied Molecular Orbital energy level of the first dopant or an energy bandgap between a Lowest Unoccupied Molecular Orbital energy level of the first host and a Lowest Unoccupied Molecular Orbital energy level of the first dopant is equal to or less than about 0.5 eV.

9. The organic light-emitting diode of claim 7, wherein each of an excited state singlet energy level and an excited state triplet energy level of the first host is higher than an excited state singlet energy level and an excited state triplet energy level of the first dopant, respectively.

10. The organic light-emitting diode of claim 7, wherein an energy bandgap between an excited state single energy level and an excited state triplet energy level of the first dopant is equal to or less than about 0.3 eV.

11. The organic light-emitting diode of claim 7, wherein the emitting material layer further comprises a second dopant.

12. The organic light-emitting diode of claim 11, wherein an excited state triplet energy level of the first dopant is lower than an excited state triplet energy level of the first host and an excited state singlet energy level of the first dopant is higher than an excited state singlet energy level of the second dopant.

13. The organic light-emitting diode of claim 6, wherein the emitting material layer includes a first emitting material layer between the first and second electrode and a second emitting material layer between the first electrode and the first emitting material layer or between the first emitting material layer and the second electrode.

14. The organic light-emitting diode of claim 13, wherein the first emitting material layer includes a first host and a first dopant, wherein the first dopant comprises the organic compound.

15. The organic light-emitting diode of claim 14, wherein the second emitting material layer includes a second host and a second dopant.

16. The organic light-emitting diode of claim 15, wherein an excited state singlet energy level of the first dopant is higher than an excited state singlet energy level of the second dopant.

17. The organic light-emitting diode of claim 15, wherein each of an excited state singlet energy level and an excited state triplet energy level of the first host is higher than an excited state singlet energy level and an excited state triplet energy level of the first dopant, respectively, and an excited state singlet energy level of the second host is higher than an excited state singlet energy level of the second dopant.

18. The organic light-emitting diode of claim 15, wherein the second emitting material layer is disposed between the first electrode and the first emitting material layer, and further comprising an electron blocking layer disposed between the first electrode and the second emitting material layer.

19. The organic light-emitting diode of claim 18, wherein the second host is formed as the same material as the electron blocking layer.

20. The organic light-emitting diode of claim 15, wherein the second emitting material layer is disposed between the first emitting material layer and the second electrode, and further comprising a hole blocking layer between the second emitting material layer and the second electrode.

21. The organic light-emitting diode of claim 20, wherein the second host is formed as the same material as the hole blocking layer.

22. The organic light-emitting diode of claim 13, the emitting material layer further comprises a third emitting material layer disposed oppositely to the second emitting material layer with respect to the first emitting material layer.

23. The organic light-emitting diode of claim 22, wherein the first emitting material layer comprises a first host and a first dopant, wherein the first dopant comprises the organic compound.

24. The organic light-emitting diode of claim 23, wherein the second emitting material layer comprise a second host and a second dopant and the third emitting material layer comprises a third host and a third dopant.

25. The organic light-emitting diode of claim 24, wherein an excited state singlet energy level of the first dopant is higher than excited state singlet energy levels of the second and third dopants.

26. The organic light-emitting diode of claim 24, wherein each of an excited state singlet energy level and an excited state triplet energy level of the first host is higher than an excited state singlet energy level and an excited state triplet energy level of the first dopant, respectively, an excited state singlet energy level of the second host is higher than an excited state singlet energy level of the second dopant, and an excited state singlet energy level of the third host is higher than an excited state singlet energy level of the third dopant.

27. The organic light-emitting diode of claim 24, wherein the second emitting material layer is disposed between the first electrode and the first emitting material layer and the third emitting material layer is disposed between the first emitting material layer and the second electrode, and further comprising an electron blocking layer disposed between the first electrode and the second emitting material layer.

28. The organic light-emitting diode of claim 27, wherein the second host is formed as the same material as the electron blocking layer.

29. The organic light-emitting diode of claim 24, wherein the second emitting material layer is disposed between the first electrode and the first emitting material layer and the third emitting material layer is disposed between the first emitting material layer and the second electrode, and further comprising a hole blocking layer disposed between the second electrode and the third emitting material layer.

30. The organic light-emitting diode of claim 29, wherein the third host is formed as the same material as the hole blocking layer.

31. The organic light-emitting diode of claim 30, further comprising an electron blocking layer disposed between the first electrode and the second emitting material layer.

32. The organic light-emitting diode of claim 31, wherein the second host is formed as the same material as the electron blocking layer.

33. An organic light-emitting device, comprising:
a substrate; and
an organic light-emitting diode according to claim 10 over the substrate.

34. The organic light-emitting device of claim 33, wherein the organic light-emitting device comprises an organic light-emitting display device.

* * * * *